US006638977B1

(12) United States Patent
Madison et al.

(10) Patent No.: US 6,638,977 B1

(45) Date of Patent: Oct. 28, 2003

(54) PLASMINOGEN ACTIVATOR INHIBITOR ANTAGONISTS

(75) Inventors: Edwin L. Madison, Del Mar, CA (US); Terence K. Brunck, Santa Fe, NM (US); Joseph Edward Semple, San Diego, CA (US); Marguerita Lim-Wilby, La Jolla, CA (US); Kent E. Pryor, San Diego, CA (US)

(73) Assignee: Corvas International, Inc., San Diego, CA (US)

(*) Notice: Subject to any disclaimer, the term of this patent is extended or adjusted under 35 U.S.C. 154(b) by 0 days.

(21) Appl. No.: 09/444,172

(22) Filed: Nov. 19, 1999

(51) Int. Cl.$^7$ ........................ A01N 37/12; C07C 321/00

(52) U.S. Cl. ........................ 514/538; 514/532; 514/543; 514/570; 514/571; 514/544; 560/9; 560/15; 560/18; 560/24; 560/30; 560/55; 560/64; 562/426; 562/452

(58) Field of Search ................................ 514/532, 538, 514/543, 570, 571, 544; 560/15, 18, 24, 30, 9, 55, 64; 562/426, 452

(56) References Cited

U.S. PATENT DOCUMENTS

| | | | | |
|---|---|---|---|---|
| 3,710,795 A | | 1/1973 | Higuchi et al. | 128/260 |
| 3,882,230 A | | 5/1975 | Holland | 424/317 |
| RE28,819 E | | 5/1976 | Thompson | 424/243 |
| 3,983,164 A | | 9/1976 | Thorne et al. | 260/473 |
| 4,044,126 A | | 8/1977 | Cook et al. | 424/243 |
| 4,221,919 A | | 9/1980 | Grimova et al. | 562/465 |
| 4,323,691 A | | 4/1982 | Ours et al. | 560/36 |
| 4,328,245 A | | 5/1982 | Yu et al. | 424/305 |
| 4,358,603 A | | 11/1982 | Yu | 560/2 |
| 4,364,923 A | | 12/1982 | Cook et al. | 424/46 |
| 4,409,239 A | | 10/1983 | Yu | 424/305 |
| 4,410,545 A | | 10/1983 | Yu et al. | 424/305 |
| 4,414,209 A | | 11/1983 | Cook et al. | 424/243 |
| 4,522,811 A | | 6/1985 | Eppstein et al. | 514/2 |
| 4,764,359 A | | 8/1988 | Lemelson | 424/1.1 |
| 4,847,195 A | * | 7/1989 | Khanna et al. | |
| 5,026,558 A | | 6/1991 | Hwang | 424/400 |
| 5,033,252 A | | 7/1991 | Carter | 53/425 |
| 5,052,558 A | | 10/1991 | Carter | 206/439 |
| 5,323,907 A | | 6/1994 | Kalvelage | 206/531 |
| 5,456,663 A | | 10/1995 | Lemelson | 604/50 |
| 5,543,391 A | | 8/1996 | Yatvin et al. | 514/2 |
| 5,585,404 A | | 12/1996 | Norinder et al. | 514/643 |
| 5,736,576 A | | 4/1998 | Kun et al. | 514/570 |
| 5,750,530 A | | 5/1998 | Bryans et al. | 514/255 |
| 5,820,879 A | | 10/1998 | Fernandez et al. | 424/450 |
| 5,866,610 A | | 2/1999 | Lang et al. | 514/617 |
| 5,891,877 A | | 4/1999 | Brocchini et al. | 514/235.8 |
| 5,902,812 A | | 5/1999 | Brocchini et al. | 514/253 |
| 5,922,775 A | | 7/1999 | Kun et al. | 514/685 |
| 6,017,958 A | | 1/2000 | Kun et al. | 514/531 |
| 2002/0037857 A1 | | 3/2002 | Semple et al. | 514/19 |

FOREIGN PATENT DOCUMENTS

| | | | |
|---|---|---|---|
| DE | 2239136 | * | 3/1973 |
| EP | 0257352 | * | 8/1987 |
| EP | 0548711 | | 12/1992 |
| EP | 0612723 | | 2/1994 |
| FR | 0008005 | | 5/1967 |
| GB | 1209945 | | 10/1970 |
| GB | 1400851 | * | 7/1975 |
| GB | 2065121 | | 12/1980 |
| WO | 9220331 | | 11/1992 |
| WO | 9324442 | | 12/1993 |
| WO | 9405153 | | 3/1994 |
| WO | 9407492 | | 4/1994 |
| WO | 9611904 | | 4/1996 |
| WO | 9640048 | | 12/1996 |
| WO | 9746228 | | 12/1997 |
| WO | 9911255 | | 3/1999 |
| WO | 9920263 | | 4/1999 |

OTHER PUBLICATIONS

Ansel, *Introduction to Pharmaceutical Dosage Forms, Fourth Edition*, 126 (1985).

Bajou et al., Absence of host plasminogen activator inhibitor 1 prevents cancer invasion and vascularization, *Nat. Med.* 4(8): 923–928 (1998).

Bell et al., Synthesis of thyroxine: biomimetic studies, *Can, J. Chem.* 75:873–883 (1997).

Björquist et al., Identification of the Binding Site for a Low–Molecular–Weight Inhibitor of Plasminogen Activator Inhibitor Type 1 by Site–Directed Mutagenesis, *Biochemistry* 37:1227–1234 (1998).

Bonvino et al., Nitro Compounds as Alkylating Reagents in Friedel–crafts Conditions, *Tetrahedron* 37:615–620 (1981).

Charlton et al., XR5118, a novel modulator of plasminogen activator inhibitor–1 (PAI–1), increases endogenous tPA activity in the rat, *Fibrinolysis and Proteolysis* 11(1):51–56 (1997).

Charlton et al., Evaluation of a Low Molecular Weight Modulator of Human Plasminogen Activator Inhibitor–1 Activity, *Thrombosis and Haemostasis* 75(5):808–815 (1996).

Evans et al., Synthesis of Diaryl Ethers through the Copper–Promoted Arylation of Phenols with Arylboronic Acids. An Expedient Synthesis of Thyroxine, *Tetrahedron Letters* 39:2937–2940 (1998).

(List continued on next page.)

*Primary Examiner*—Paul J. Killos
(74) *Attorney, Agent, or Firm*—Heller Ehrman White & McAuliffe LLP; Stephanie Seidman; Dale Rieger

(57) ABSTRACT

Compounds and pharmaceutical compositions useful as plasminogen activator inhibitor (PAI) antagonists are provided. In particular, methods of antagonizing PAI with substituted and unsubstituted aryl and heteroaryl ethers and thioethers are provided.

71 Claims, No Drawings

OTHER PUBLICATIONS

Gilbert, Sulfonation and Related Reactions, *Interscience Publishers, New York* pp. 62–83 and 87–124 (1965).

Greene et al., Protective Groups in Organic Synthesis, *John Wiley & Sons, Inc., New York* (1981).

IUPAC–IUB Commission on Biochemical Nomenclature, Abbreviated Nomenclature of Synthetic Polypeptides (Polymerized Amino Acids), *Biochemistry* 11(5):942–944 (1972).

Madison et al., Serpin–resistant mutants of human tissue–type plasminogen activator, *Nature* 339:721–724 (1989).

Madison et al., Converting Tissue Plasminogen Activator to a Zymogen: A Regulatory Triad of Asp–His–Ser, *Science* 262:419–421 (1993).

Madison et al., Amino acid residues that affect interaction of tissue–type plaminogen activator with plasminogen activator inhibitor 1, *Proc. Natl. Acad. Sci. USA* 87:3530–3533 (1990).

March, Advanced Organic Chemistry, *John Wiley & Sons, Inc., New York* p. 804 (1985).

Nilsson et al., A New Kit for the Determination of Tissue Plasminogen Activator and its Inhibitor in Blood, *Fibrinolysis* 1:163–168 (1987).

Nogrady, Medicinal Chemistry: A Biochemical Approach, *Oxford University Press, New York* pp. 388–392 (1985).

Olah, Friedel–Crafts and Related Reactions, *Interscience Publishers, New York* 3:1355–1392 (1964).

Remington's Pharmaceutical Sciences, *Mark Publishing Company, Pennsylvania* (1975).

Salamonczyk et al., A Concise Synthesis of Thyroxine ($T_4$) and 3,5,3'–Triiodo–L–thyronine ($T_3$), *Tetrahedron Letters* 38(40):6965–6968 (1997).

Kuchar et al., "Use of Qsar in design of antiinflammatory fluorinated arylalkanoic acids," *Collect. Czech. Chem. Commun.* 55:296–306 (1990).

Kuchar et al., "Benzyloxyarylaliphatic acids; sythesis and quantitative relations between structure and antiinflammatory activity," *Collect. Czech. Chem. Commun.* 47:2514–2524 (1982).

Perrier and Labelle, "Liquid–phase synthesis with solid–phase workup: application to multistep and combinatorial synthesis," *J. Org. Chem.* 64:2100–2113 (1999); supporting info pp. 1–18.

Chem Abs 121: 280 387 1993.*

Derwent #000925695, WPI Acc No.: 12973–02913U/197303 (citing French Patent No. FR 8005 M).

Derwent #009512849, WPI Acc No.: 1993–206385/199326 (citing European Patent No. 0548711).

Derwwnt #012398862, WPI Acc No.: 1999–204969/199917 (citing International PCT application No. WO 99/11255).

* cited by examiner

PLASMINOGEN ACTIVATOR INHIBITOR ANTAGONISTS

FIELD OF THE INVENTION

Provided herein are compounds and pharmaceutical compositions useful as plasminogen activator inhibitor (PAI) antagonists, particularly PAI type 1 (PAI-1) antagonists. In particular, methods of antagonizing PAI, particularly PAI-1, with substituted and unsubstituted biaryl and benzyl ethers and thioethers are provided.

BACKGROUND OF THE INVENTION

Plasminogen activators (PA's), such as tissue type plasminogen activator (tPA) and urokinase plasminogen activator (uPA), are serine proteases that control the activation of the zymogen, plasminogen, to the active enzyme plasmin. Plasmin is important in a number of (patho)physiological processes which include fibrinolysis, tissue remodelling, tumor growth and metastasis.

The glycoprotein, plasminogen activator inhibitor type 1 (PAI-1), is an endogenous fast-acting inhibitor of PA activity. PAI-1 is a member of the serpin (serine protease inhibitor) family of protease inhibitors and is synthesized by a variety of cells including endothelial cells. An imbalance between PAs and PAI-1 contributes to several pathological conditions including thrombosis, inflammation, tumor growth and metastasis.

Thrombosis

Elevated circulating levels of PAI-1 can result in a downregulation of fibrinolysis. This condition can contribute to the pathogenesis of various thrombotic disorders, including myocardial infarction, reocclusion following thrombolytic therapy, deep vein thrombosis and disseminated intravascular coagulation. Compounds and pharmaceutical compositions that antagonize PAI-1 can be used in the treatment of certain thrombotic disorders by enhancing the extent of endogenous fibrinolysis by PAs. In addition, PAI-1 antagonists, in this context, may enhance the efficacy of thrombolytic therapy where exogenous PAs such as recombinant tPA (r-tPA) is administered to a patient to reperfuse blood vessels occluded by thrombus as is commonly observed in myocardial infarction (see, eq., U.S. Pat. Nos. 5,750,530, 5,902,812 and 5,891,877).

Cancer

Current therapies for cancer are generally characterized by limited efficacy, or significant and/or debilitating side effects. In certain solid tumor cancers, malignant tumors invade and disrupt nearby tissues and can also metastasize or spread to other organs and tissues. The impact of these secondary metastatic tumors on vital organs such as the lungs and the liver frequently leads to death. Surgery is used to remove solid tumors that are accessible to the surgeon and can be effective if the cancer has not metastasized. Radiation therapy also can be employed to irradiate a solid tumor and surrounding tissues and is a firstline therapy for inoperable tumors, but side effects are a limiting factor in treatment. Radiation therapy is used frequently in conjunction with surgery either to reduce the tumor mass prior to surgery or to destroy tumor cells that may remain at the tumor site after surgery. However, radiation therapy cannot assure that all tumor cells will be destroyed and has only limited utility for treating widespread metastases. While surgery and radiation therapy are the primary treatments for solid tumors, chemotherapy and hormonal treatments often are used as adjunctive therapies and also are used as primary therapies for inoperable or metastatic cancers. However, the side effects of these therapies can often limit their effectiveness due to patient tolerance and compliance.

Plasminogen Activator Inhibitor (PAI) and its Role in Solid Tumor Cancer

The role of PAI, particularly PAI-1, in the natural progression of certain solid tumor cancers has been suggested based on the strong correlation of increased levels of this protein and a poor patient survival rates in certain types of cancer, including breast cancer. In addition, recent evidence in animals genetically lacking PAI (PAI knockouts) has demonstrated that the growth and metastasis of certain human tumors is significantly impaired, suggesting that PAI may play a pivotal role in the growth and metastatic migration of certain solid tumors Bajou et al. (1998) *Nat. Med.* 4(8):923–928).

PAI antagonists that have been reported to date include the anthranilic acid derivative AR-H029953XX (Björquist et al. (1998) *Biochemistry* 37:1 227–1 234) and several diketopiperazines (piperazinediones)(see, e.g., Charlton et al. (1997) *Fibrinolysis & Proteolysis* 11 (1):51–56; Charlton et al. (1996) *Thrombosis and Haemostasis* 75(5):808–815; and U.S. Pat. Nos. 5,750,530; 5,902,812; and 5,891,877).

Thus, it is an object herein to provide compositions and methods for antagonizing the effects of PAI, particularly PAI-1. It is also an object herein to provide methods of treating, preventing, or ameliorating one or more symptoms of disease states, including, but not limited to, thrombotic disorders, such as myocardial infarction, reocclusion following thrombolytic therapy, deep vein thrombosis and disseminated intravascular coagulation, and cancer, particularly solid tumors, that are modulated or otherwise affected by the activity of PAI, particularly PAI-1. A further object herein is to provide methods of attenuating tumor or other cancer metastasis. Finally, it is an object herein to provide methods of modulating the interaction of PAs, particularly tPA and uPA, with PAI, particularly PAI-1.

SUMMARY OF THE INVENTION

Compounds and compositions useful as plasminogen activator inhibitor (PAI) antagonists are provided. The compounds and compositions are useful in the treatment, prevention, or amelioration of one or more symptoms of thrombotic disorders, such as myocardial infarction, reocclusion following thrombolytic therapy, deep vein thrombosis and disseminated intravascular coagulation, and cancer, particularly tumors, solid tumors, metastatic solid tumors and breast cancer. The compositions contain compounds that are active in assays that measure PAI-1 antagonist activity. The compounds are substituted aryl or heteroaryl ethers and thioethers that possess at least one acidic moiety, including, but not limited to, a carboxylic acid, sulfonic acid, sulfinic acid, phosphonic acid, phosphinic acid or boronic acid group.

The compounds provided herein are ethers and thioethers that have the formula $Ar^1—X'—Ar^2$, wherein X' is O, S, $(CH_2)_dO$ or $(CH_2)_dS$ where d is an integer from 1 to 6; and $Ar^1$ and $Ar^2$ are each independently selected from monocyclic or fused bicyclic aryl and heteroaryl, preferably aryl, more preferably phenyl, and are substituted with at least one acidic group selected from a carboxylic acid, sulfonic acid, sulfinic acid, phosphonic acid, phosphinic acid or boronic acid group. Preferred acidic groups are carboxylic acid and sulfonic acid groups, more preferably $(CH_2)_aCOOH$, $(CH_2)_bCH(NRR')COOH$ and $(CH_2)_cSO_3H$ where R and R' are each independently hydrogen or an amino acid blocking or protecting group (see, e.g., Greene, T. W. *Protective Groups*

*in Organic Synthesis* (1981) John Wiley & Sons, New York) including, but not limited to, tert-butoxycarbonyl (BOC), benzyloxycarbonyl (Cbz), 9-fluorenylmethoxycarbonyl (Fmoc), para-toluenesulfonyl (tosyl), 2,2,2-trichloroethoxycarbonyl, 2-trimethylsilylethoxycarbonyl, formyl, acetyl, benzyloxymethyl, benzyloxymethoxycarbonyl, unsubstituted or substituted benzoyl, unsubstituted or substituted benzyl, unsubstituted or substituted triphenylmethyl (trityl), or unsubstituted or substituted benzylidene; or R and R' together form phthaloyl, succinimidyl or maleimidyl; a is an integer from 0 to 6, b is an integer from 1 to 4, preferably 1 or 2; and c is an integer from 0 to 4, preferably 0.

$Ar^1$ and $Ar^2$ may be substituted further with one or more groups such as halide, pseudohalide, nitro, hydroxy, alkoxy, aryloxy, cycloalkoxy, haloalkyl, haloalkoxy, aryl, heteroaryl, heterocyclyl, alkyl or cycloalkyl. The aryl, heteroaryl, heterocyclyl and cycloalkyl substituents may be further substituted with $C_{1-20}$alkyl-L-, $C_{2-20}$alkenyl-L-, or $C_{2-20}$alkynyl-L-, where L is a direct link, amido, carboxy, carbonyl, carbamoyl, sulfonyl, carbamide, ureido, sulfonainide, hydrazinyl, hydrazide, semicarbazide, carbazate, thiocarbazate, isothiocarbazate or sulfonyl hydrazide.

Also of interest are any pharmaceutically-acceptable derivatives, including salts, esters, acids, enol ethers and esters, bases, solvates, hydrates and prodrugs of the compounds described herein. Pharmaceutically-acceptable salts, include, but are not limited to, amine salts, such as but not limited to N,N'-dibenzylethylenediamine, chloroprocaine, choline, ammonia, diethanolamine and other hydroxyalkylamines, ethylenediamine, N-methylglucamine, procaine, N-benzylphenethylamine, 1-para-chlorobenzyl-2-pyrrolidin-1'-ylmethylbenzimidazole, diethylamine and other alkylamines, piperazine and tris(hydroxymethyl) aminomethane; alkali metal salts, such as but not limited to lithium, potassium and sodium; alkali earth metal salts, such as but not limited to barium, calcium and magnesium; transition metal salts, such as but not limited to zinc; and other metal salts, such as but not limited to sodium hydrogen phosphate and disodium phosphate; and also including, but not limited to, salts of mineral acids, such as but not limited to hydrochlorides and sulfates; and salts of organic acids, such as but not limited to acetates, lactates, malates, tartrates, citrates, ascorbates, succinates, butyrates, valerates and fumarates.

Pharmaceutical compositions formulated ,for administration by an appropriate route and means containing effective concentrations of one or more of the compounds provided herein, or pharmaceutically acceptable derivatives thereof, that deliver amounts effective for the treatment, prevention, or amelioration of one or more symptoms of thrombotic disorders, including, but not limited to, myocardial infarction, reocclusion following thrombolytic therapy, deep vein thrombosis and disseminated intravascular coagulation, and cancer, including, but not limited to, tumors, solid tumors, metastatic solid tumors and breast cancer, are also provided. The effective amounts and concentrations are effective for ameliorating any of the symptoms of any of the disorders.

Methods for treatment, prevention, or amelioration of one or more symptoms of thrombotic disorders, including, but not limited to, myocardial infarction, reocclusion following thrombolytic therapy, deep vein thrombosis and disseminated intravascular coagulation, and cancer, including, but not limited to, tumors, solid tumors, metastatic solid tumors and breast cancer, using one or more of the compounds provided herein, or pharmaceutically acceptable derivatives thereof, are provided.

Methods of modulating the activity of PAI, particularly PAI-1, using the compounds and compositions provided herein are also provided. The compounds and compositions provided herein are active in assays that measure the activity of PAI, specifically PAI-1. Preferred are methods of inhibiting the activity of PAI, in particular PAI-1.

Methods of modulating the interaction of PAs, particularly tPA and uPA, with PAI, particularly PAI-1, by administering one or more of the compounds provided herein, or pharmaceutically acceptable derivatives thereof, are provided.

Methods of attenuating metastasis by administration of one or more of the compounds and compositions provided herein are also provided.

Methods of modulating angiogenesis, preferably inhibiting angiogenesis, by administration of one or more of the compounds and compositions provided herein are provided.

In practicing the methods, effective amounts of the compounds or compositions containing therapeutically effective concentrations of the compounds formulated for oral, intravenous, local or topical application for the treatment of thrombotic disorders, including, but not limited to, myocardial infarction, reocclusion following thrombolytic therapy, deep vein thrombosis and disseminated intravascular coagulation, and cancer, including, but not limited to, tumors, solid tumors, metastatic solid tumors and breast cancer, are administered to an individual exhibiting the symptoms of these disorders. The amounts are effective to ameliorate or eliminate one or more symptoms of the disorders.

Articles of manufacture containing packaging material, a compound or composition, or pharmaceutically acceptable derivative thereof, provided herein, which is effective for antagonizing PAI, particularly PAI-1, or for treatment, prevention or amelioration of one or more symptoms of thrombotic disorders, including, but not limited to, myocardial infarction, reocclusion following thrombolytic therapy, deep vein thrombosis and disseminated intravascular coagulation, and cancer, including, but not limited to, tumors, solid tumors, metastatic solid tumors and breast cancer, within the packaging material, and a label that indicates that the compound or composition, or pharmaceutically acceptable derivative thereof, is used for antagonizing PAI, particularly PAI-1, or for treatment, prevention or amelioration of one or more symptoms of thrombotic disorders, including, but not limited to, myocardial infarction, reocclusion following thrombolytic therapy, deep vein thrombosis and disseminated intravascular coagulation, and cancer, including, but not limited to, tumors, solid tumors, metastatic solid tumors and breast cancer, are provided.

DETAILED DESCRIPTION OF PREFERRED EMBODIMENTS

A. Definitions

Unless defined otherwise, all technical and scientific terms used herein have the same meaning as is commonly understood by one of skill in the art to which this invention belongs. All patents, patent applications and publications referred to herein are incorporated by reference in their entirety.

As used herein, "plasmin" refers to the trypsin-like serine protease that is responsible for digesting fibrin in blood clots. Plasmin is generated from plasminogen by the action of another protease, plasminogen activator.

As used herein, "plasminogen" refers to the zymogen of plasmin.

As used herein, "plasminogen activator" or "PA" refers to a serine protease that acts on plasminogen to generate plasmin. PA is produced by many normal and invasive cells. Examples of PAs include, but are not limited to, uPA (urokinase, 70 kDa), tissue plasminogen activator (tPA, 55 kDa), and streptokinase.

As used herein, "plasminogen activator inhibitor" or "PAI" refers to an endogenous substance that inhibits the action of plasminogen activator. In particular, "PAI-1" refers to plasminogen activator inhibitor type 1, which is the fast acting from of PAI.

As used herein, the $IC_{50}$ refers to an amount, concentration or dosage of a particular test compound that achieves a 50% inhibition of a maximal response, such as antagonism of PAI.

As used herein, $EC_{50}$ refers to a dosage, concentration or amount of a particular test compound that elicits a dose-dependent response at 50% of maximal expression of a particular response that is induced, provoked or potentiated by the particular test compound.

As used herein, pharmaceutically acceptable derivatives of a compound include salts, esters, enol ethers, enol esters, acids, bases, solvates, hydrates or prodrugs thereof that may be readily prepared by those of skill in this art using known methods for such derivatization and that produce compounds that may be administered to animals or humans without substantial toxic effects and that either are pharmaceutically active or are prodrugs. For example, acidic groups can be esterified or neutralized.

As used herein, treatment means any manner in which one or more of the symptoms of a condition, disorder or disease are ameliorated or otherwise beneficially altered. Treatment also encompasses any pharmaceutical use of the compositions herein, such as use as contraceptive agents.

As used herein, amelioration of the symptoms of a particular disorder by administration of a particular pharmaceutical composition refers to any lessening, whether permanent or temporary, lasting or transient that can be attributed to or associated with administration of the composition.

As used herein, biological activity refers to the in vivo activities of a compound or physiological responses that result upon in vivo administration of a compound, composition or other mixture. Biological activity, thus, encompasses therapeutic effects and pharmaceutical activity of such compounds, compositions and mixtures.

As used herein, a prodrug is a compound that, upon in vivo administration, is metabolized or otherwise converted to the biologically, pharmaceutically or therapeutically active form of the compound. To produce a prodrug, the pharmaceutically active compound is modified such that the active compound will be regenerated by metabolic processes. The prodrug may be designed to alter the metabolic stability or the transport characteristics of a drug, to mask side effects or toxicity, to improve the flavor of a drug or to alter other characteristics or properties of a drug. By virtue of knowledge of pharmacodynamic processes and drug metabolism in vivo, those of skill in this art, once a pharmaceutically active compound is known, can design prodrugs of the compound (see, e.g., Nogrady (1985) *Medicinal Chemistry A Biochemical Approach*, Oxford University Press, New York, pages 388–392).

It is to be understood that the compounds, provided herein may contain chiral centers. Such chiral centers may be of either the (R) or (S) configuration, or may be a mixture thereof. Thus, the compounds provided herein may be enantiomerically pure, or be stereoisomeric or diastereomeric mixtures. In the case of amino acid residues, such residues may be of either the L- or D-form. The preferred configuration for naturally occurring amino acid residues is L. It is to be understood that the chiral centers of the compounds provided herein may undergo epimerization in vivo. As such, one of skill in the art will recognize that administration of a compound in its (R) form is equivalent, for compounds that undergo epimerization in vivo, to administration of the compound in its (S) form.

As used herein, substantially pure means sufficiently homogeneous to appear free of readily detectable impurities as determined by standard methods of analysis, such as thin layer chromatography (TLC), gel electrophoresis, high performance liquid chromatography (HPLC) and mass spectrometry (MS), used by those of skill in the art to assess such purity, or sufficiently pure such that further purification would not detectably alter the physical and chemical properties, such as enzymatic and biological activities, of the substance. Methods for purification of the compounds to produce substantially chemically, pure compounds are known to those of skill in the art. A substantially chemically pure compound may, however, be a mixture of stereoisomers. In such instances, further purification might increase the specific activity of the compound.

As used herein, alkyl, alkenyl and alkynyl carbon chains, if not specified, contain from 1 to 20 carbons, preferably 1 to 16 carbons, and are straight or branched. Alkenyl carbon chains of from 2 to 20 carbons preferably contain 1 to 8 double bonds, and the alkenyl carbon chains of 1 to 16 carbons preferably contain 1 to 5 double bonds. Alkynyl carbon chains of from 2 to 20 carbons preferably contain 1 to 8 triple bonds, and the alkynyl carbon chains of 2 to 16 carbons preferably contain 1 to 5 triple bonds. Exemplary alkyl, alkenyl and alkynyl groups herein include, but are not limited to, methyl, ethyl, propyl, isopropyl, isobutyl, n-butyl, sec-butyl, tert-butyl, isopentyl, neopentyl, tert-penytyl and isohexyl. The alkyl, alkenyl and alkynyl groups, unless otherwise specified, may be optionally substituted, with one or more groups, preferably alkyl group substituents that may be the same or different. As used herein, lower alkyl, lower alkenyl, and lower alkynyl refer to carbon chains having less than about 6 carbons. As used herein, "alk(en)(yn)yl" refers to an alkyl group containing at least one double bond and at least one triple bond.

As used herein, an "alkyl group substituent" includes halo, haloalkyl, preferably halo lower alkyl, aryl, hydroxy, alkoxy, aryloxy, alkyloxy, alkylthio, arylthio, aralkyloxy, aralkylthio, carboxy alkoxycarbonyl, oxo and cycloalkyl.

As used herein, "aryl" refers to cyclic groups containing from 5 to 19 carbon atoms. Aryl groups include, but are not limited to groups, such as fluorenyl, substituted fluorenyl, phenyl, substituted phenyl, naphthyl and substituted naphthyl, in which the substituent is lower alkyl, halogen, or lower alkoxy.

As used herein, an "aryl group substituent" includes alkyl, cycloalkyl, cycloalkylalkyl, aryl, heteroaryl optionally substituted with 1 or more, preferably 1 to 3, substituents selected from halo, halo alkyl and alkyl, aralkyl, heteroaralkyl, alkenyl containing 1 to 2 double bonds, alkynyl containing 1 to 2 triple bonds, alk(en)(yn)yl groups, halo, pseudohalo, cyano, hydroxy, haloalkyl and polyhaloalkyl, preferably halo lower alkyl, especially trifluoromethyl, formyl, alkylcarbonyl, arylcarbonyl that is optionally substituted with 1 or more, preferably 1 to 3, substituents selected from halo, halo alkyl and alkyl, heteroarylcarbonyl, carboxy, alkoxycarbonyl, aryloxycarbonyl, aminocarbonyl, alkylaminocarbonyl, dialkylaminocarbonyl, arylaminocarbonyl, diarylaminocarbonyl, aralkylaminocarbonyl, alkoxy, aryloxy, perfluoroalkoxy, alkenyloxy, alkynyloxy, arylalkoxy, aminoalkyl, alkylaminoalkyl, dialkylaminoalkyl, arylaminoalkyl, amino, alkylamino, dialkylamino, arylamino, alkylarylamino, alkylcarbonylamino, arylcarbonylamino, azido, nitro, mercapto, alkylthio, arylthio, perfluoroalkylthio, thiocyano, isothiocyano, alkylsulfinyl, alkylsulfonyl, arylsulfinyl, arylsulfonyl, aminosulfonyl, alkylaminosulfonyl, dialkylaminosulfonyl and arylaminosulfonyl.

As used herein, "aralkyl" refers to an alkyl group in which one of the hydrogen atoms of the alkyl is replaced by an aryl group.

As used herein, "heteroaralkyl" refers to an alkyl group in which one of the hydrogen atoms of the alkyl is replaced by a heteroaryl group.

As used herein, "cycloalkyl" refers to a saturated mono- or multicyclic ring system, preferably of 3 to 10 carbon atoms, more preferably 3 to 6 carbon atoms; cycloalkenyl and cycloalkynyl refer to mono- or multicyclic ring systems that respectively include at least one double bond and at least one triple bond. Cycloalkenyl and cycloalkynyl groups may preferably contain 3 to 10 carbon atoms, with cycloalkenyl groups more preferably containing 4 to 7 carbon atoms and cycloalkynyl groups more preferably containing 8 to 10 carbon atoms. The ring systems of the cycloalkyl, cycloalkenyl and cycloalkynyl groups may be composed of one ring or two or more rings which may be joined together in a fused, bridged or spiro-connected fashion, and may be optionally substituted with one or more alkyl group substituents. "Cycloalk(en)(yn)yl" refers to a cylcoalkyl group containing at least one double bond and at least one triple bond.

As used herein, "heteroaryl" refers to a monocyclic or multicyclic ring system, preferably of about 5 to about 15 members where one or more, more preferably 1 to 3 of the atoms in the ring system is a heteroatom, that is, an element other than carbon, for example, nitrogen, oxygen and sulfur atoms. The heteroaryl may be optionally substituted with one or more, preferably 1 to 3, aryl group substituents. The heteroaryl group may be optionally fused to a benzene ring. Exemplary heteroaryl groups include, for example, furyl, imidazinyl, pyrrolidinyl, pyrimidinyl, tetrazolyl, thienyl, pyridyl, pyrrolyl, N-methylpyrrolyl, quinolinyl and isoquinolinyl, with pyridyl and quinolinyl being preferred.

As used herein, "heterocyclic" refers to a monocyclic or multicyclic ring system, preferably of 3 to 10 members, more preferably 4 to 7 members, even more preferably 5 to 6 members, where one or more, preferably 1 to 3 of the atoms in the ring system is a heteroatom, that is, an element other than carbon, for example, nitrogen, oxygen and sulfur atoms. The heterocycle may be optionally substituted with one or more, preferably 1 to 3 aryl group substituents. Preferred substituents of the heterocyclic group include hydroxy, amino, alkoxy containing 1 to 4 carbon atoms, halo lower alkyl, including trihalomethyl, such as trifluoromethyl, and halogen. As used herein, the term heterocycle may include reference to heteroaryl.

As used herein, the nomenclature alkyl, alkoxy, carbonyl, etc. are used as is generally understood by those of skill in this art. For example, as used herein alkyl refers to saturated carbon chains that contain one or more carbons; the chains may be straight or branched or include cyclic portions or be cyclic. As used herein, alicyclic refers to aryl groups that are cyclic.

Where the number of any given substituent is not specified (e.g., "haloalkyl"), there may be one or more substituents present. For example, "haloalkyl" may include one or more of the same or different halogens. As another example, "$C_{1-3}$alkoxyphenyl" may include one or more of the same or different alkoxy groups containing one, two or three carbons.

Where named substituents such as carboxy or substituents represented by variables such as W are separately enclosed in parentheses, yet possess no subscript outside the parentheses indicating numerical value and which follow substituents not in parentheses, e.g., "$C_{1-4}$alkyl(W)(carboxy)", "W" and "carboxy" are each directly attached to $C_{1-4}$alkyl.

As used herein, "halogen" or "halide" refers to F, Cl, Br or I.

As used herein, pseudohalides are compounds that behave substantially similar to halides. Such compounds can be used in the same manner and treated in the same manner as halides ($X^-$, in which X is a halogen, such as Cl or Br). Pseudohalides include, but are not limited to, cyanide, cyanate, thiocyanate, selenocyanate, trifluoromethoxy, trifluoromethyl and azide.

As used herein, "haloalkyl" refers to a lower alkyl radical in which one or more of the hydrogen atoms are replaced by halogen including, but not limited to, chloromethyl, trifluoromethyl, 1-chloro-2-fluoroethyl and the like.

As used herein, "haloalkoxy" refers to RO— in which R is a haloalkyl group.

As used herein, "sulfinyl" or "thionyl" refers to —S(O)—. As used herein, "sulfonyl" or "sulfuryl" refers to —$S(O)_2$—. As used herein, "sulfo" refers to —$S(O)_3$—.

As used herein, "carboxy" refers to a divalent radical, —C(O)O—.

As used herein, "aminocarbonyl" refers to —$C(O)NH_2$.

As used herein, "alkylaminocarbonyl" refers to —C(O)NHR in which R is hydrogen or alkyl, preferably lower alkyl. As used herein "dialkylaminocarbonyl" as used herein refers to —C(O)NR'R in which R' and R are independently selected from hydrogen or alkyl, preferably lower alkyl; "carboxamide" refers to groups of formula —NR'COR.

As used herein, "diarylaminocarbonyl" refers to —C(O)NRR' in which R and R' are independently selected from aryl, preferably lower aryl, more preferably phenyl.

As used herein, "aralkylaminocarbonyl" refers to —C(O)NRR' in which one of R and R' is aryl, preferably lower aryl, more preferably phenyl, and the other of R and R' is alkyl, preferably lower alkyl.

As used herein, "arylaminocarbonyl" refers to —C(O)NHR in which R is aryl, preferably lower aryl, more preferably phenyl.

As used herein, "alkoxycarbonyl" refers to —C(O)OR in which R is alkyl, preferably lower alkyl.

As used herein, "aryloxycarbonyl" refers to —C(O)OR in which R is aryl, preferably lower aryl, more preferably phenyl.

As used herein, "alkoxy" and "alkylthio" refer to RO— and RS—, in which R is alkyl, preferably lower alkyl.

As used herein, "aryloxy" and "arylthio" refer to RO— and RS—, in which R is aryl, preferably lower aryl, more preferably phenyl.

As used herein, "alkylene" refers to a straight, branched or cyclic, preferably straight or branched, bivalent aliphatic hydrocarbon group, preferably having from 1 to about 20 carbon atoms, more preferably 1 to 12 carbons, even more preferably lower alkylene. The alkylene group is optionally substituted with one or more "alkyl group substituents." There may be optionally inserted along the alkylene group one or more oxygen, sulphur or substituted or unsubstituted nitrogen atoms, where the nitrogen substituent is alkyl as previously described. Exemplary alkylene groups include methylene ($—CH_2—$), ethylene ($—CH_2CH_2—$), propylene ($—(CH_2)_3—$), cyclohexylene ($—C_6H_{10}—$), methylenedioxy ($—O—CH_2—O—$) and ethylenedioxy ($—O—(CH_2)_2—O—$). The term "lower alkylene" refers to alkylene groups having 1 to 6 carbons. Preferred alkylene groups are lower alkylene, with alkylene of 1 to 3 carbon atoms being particularly preferred.

As used herein, "alkenylene" refers to a straight, branched or cyclic, preferably straight or branched, bivalent aliphatic hydrocarbon group, preferably having from 2 to about 20 carbon atoms and at least one double bond, more preferably 1 to 12 carbons, even more preferably lower alkenylene. The alkenylene group is optionally substituted with one or more "alkyl group substituents." There may be optionally inserted along the alkenylene group one or more oxygen, sulphur or substituted or unsubstituted nitrogen atoms, where the nitrogen substituent is alkyl as previously described. Exemplary alkenylene groups include —CH═CH—CH═CH— and $—CH═CH—CH_2—$. The term "lower alkenylene" refers to alkenylene groups having 2 to 6 carbons. Preferred alkenylene groups are lower alkenylene, with alkenylene of 3 to 4 carbon atoms being particularly preferred.

As used herein, "alkynylene" refers to a straight, branched or cyclic, preferably straight or branched, bivalent aliphatic hydrocarbon group, preferably having from 2 to about 20 carbon atoms and at least one triple bond, more preferably 1 to 12 carbons, even more preferably lower alkynylene. The alkynylene group is optionally substituted with one or more "alkyl group substituents." There may be optionally inserted along the alkynylene group one or more oxygen, sulphur or substituted or unsubstituted nitrogen atoms, where the nitrogen substituent is alkyl as previously described. Exemplary alkynylene groups include —C≡C—C≡C—, —C≡C— and $—C≡C—CH_2—$. The term "lower alkynylene" refers to alkynylene groups having 2 to 6 carbons. Preferred alkynylene groups are lower alkynylene, with alkynylene of 3 to 4 carbon atoms being particularly preferred.

As used herein, "alk(en)(yn)ylene" refers to a straight, branched or cyclic, preferably straight or branched, bivalent aliphatic hydrocarbon group, preferably having from 2 to about 20 carbon atoms and at least one triple bond, and at least one double bond; more preferably 1 to 12 carbons, even more preferably lower alk(en)(yn)ylene. The alk(en)(yn)ylene group is optionally substituted with one or more "alkyl group substituents." There may be optionally inserted along the alkynylene group one or more oxygen, sulphur or substituted or unsubstituted nitrogen atoms, where the nitrogen substituent is alkyl as previously described. Exemplary alk(en)(yn)ylene groups include $—C═C—(CH_2)_n—C—C—$, where n is 1 or 2. The term "lower alk(en)(yn)ylene" refers to alk(en)(yn)ylene groups having up to 6 carbons. Preferred alk(en)(yn)ylene groups are lower alk(en)(yn)ylene, with alk(en)(yn)ylene of 4 carbon atoms being particularly preferred.

As used herein, "arylene" refers to a monocyclic or polycyclic, preferably monocyclic, bivalent aromatic group, preferably having from 5 to about 20 carbon atoms and at least one aromatic ring, more preferably 5 to 12 carbons, even more preferably lower arylene. The arylene group is optionally substituted with one or more "alkyl group substituents." There may be optionally inserted around the arylene group one or more oxygen, sulphur or substituted or unsubstituted nitrogen atoms, where the nitrogen substituent is alkyl as previously described. Exemplary arylene groups include 1,2-, 1,3- and 1,4-phenylene. The term "lower arylene" refers to arylene groups having 5 or 6 carbons. Preferred arylene groups are lower arylene.

As used herein, "heteroarylene" refers to a bivalent monocyclic or multicyclic ring system, preferably of about 5 to about 15 members where one or more, more preferably 1 to 3 of the atoms in the ring system is a heteroatom, that is, an element other than carbon, for example, nitrogen, oxygen and sulfur atoms. The heteroarylene group may be optionally substituted with one or more, preferably 1 to 3, aryl group substituents.

As used herein, "alkylidene" refers to a bivalent group, such as ═CR'R", which is attached to one atom of another group, forming a double bond. Exemplary alkylidene groups are methylidene ($═CH_2$) and ethylidene ($═CHCH_3$). As used herein, "aralkylidene" refers to an alkylidene group in which either R' or R" is and aryl group.

As used herein, "amido" refers to the bivalent group —C(O)NH—. "Thioamido" refers to the bivalent group —C(S)NH—. "Oxyamido" refers to the bivalent group —OC(O)NH—. "Thiaamido" refers to the bivalent group —SC(O)NH—. "Dithiaamido" refers to the bivalent group —SC(S)NH—. "Ureido" refers to the bivalent group —HNC(O)NH—. "Thioureido" refers to the bivalent group —HNC(S)NH—.

As used herein, "semicarbazide" refers to —NHC(O)NHNH—. "Carbazate" refers to the bivalent group —OC(O)NHNH—. "Isothiocarbazate" refers to the bivalent group —SC(O)NHNH—. "Thiocarbazate" refers to the bivalent group —OC(S)NHNH—. "Sulfonylhydrazide" refers to the group $—SO_2NHNH—$. "Hydrazide" refers to the bivalent group —C(O)NHNH—. "Azo" refers to the bivalent group —N═N—. "Hydrazinyl" refers to the bivalent group —NH—NH—.

As used herein, the term "amino acid" refers to α-amino acids which are racemic, or of either the D- or L-configuration. The designation "d" preceding an amino acid designation (e.g., dAla, dSer, dVal, etc.) refers to the D-isomer of the amino acid. The designation "dl" preceding an amino acid designation (e.g., dlPip) refers to a mixture of the L- and D-isomers of the amino acid.

As used herein, when any particular group, such as phenyl or pyridyl, is specified, this means that the group is unsubstituted or is substituted. Preferred substituents where not specified are halo, halo lower alkyl, and lower alkyl.

As used herein, the abbreviations for any protective groups, amino acids and other compounds, are, unless indicated otherwise, in accord with their common usage, recognized abbreviations, or the IUPAC-IUB Commission on Biochemical Nomenclature (see, *Biochem.* 1972, 11, 942).

B. Compounds Useful as PAI Antagonists

Compounds and compositions useful as plasminogen activator inhibitor (PAI) antagonists are provided. The compositions contain compounds that are active in assays that measure PAI-1 antagonist activity. The compounds and compositions provided herein are thus useful in treatment, prevention, or amelioration of one or more symptoms of disease states in which PAI, particularly PAI 1, is implicated. In preferred embodiments, the compounds are substituted aryl and heteroaryl ethers and thioethers that possess at least one acidic moiety selected from a carboxylic acid or sulfonic acid group.

In one embodiment, the compounds for use in the compositions and methods provided herein are diaryl and benzyl ethers and thioethers that have the formula:

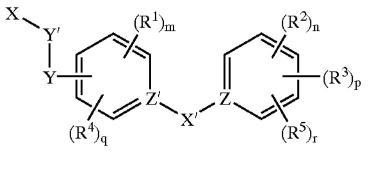

and pharmaceutically acceptable derivatives thereof, where X' is O, S, $(CH_2)_dO$ or $(CH_2)_dS$; d is an integer from 1 to 6; Z and Z' are each carbon;

$R^1$ is alkyl, aryl, alkoxy, haloalkyl, haloalkoxy, halide or pseudohalide, preferably halide, more preferably iodo; m is an integer from 0 to 4; $R^2$, $R^3$, n and p are selected from (i) and (ii) as follows:

(i) $R^2$ is alkyl, aryl, alkoxy, haloalkyl, haloalkoxy, halide or pseudohalide, preferably halide, more preferably iodo; n is an integer from 0 to 5; $R^3$ is hydroxy or alkoxy, preferably OH; p is an integer from 0 to 3; or (ii) n and p are 1; and $R^2$ and $R^3$ together form, with the carbon to which each is attached, an aryl, aromatic ring, heteroaromatic ring, carbocyclic or heterocyclic ring, which is saturated or unsaturated, containing from about 3 to about 16 members, preferably 3 to about 10 members, more preferably 5 to 7 members; in particular, $R^2$ and $R^3$ together form —CH=CH—CH=CH—, —N=CH—CH=CH—, —CH=N—CH=CH—, —CH=CH—O—, —CH=CH—S— or —CH=CH—N($R^{20}$)— where $R^{20}$ is H, alkyl, aryl or aralkyl;

$R^4$ and $R^5$ are each independently selected from $—SO_3^-$, $—NO_2$, alkyl, hydroxy, alkoxy, halide, pseudohalide; preferably $—SO_3^-$, $—NO_2$ and lower alkyl; more preferably $—SO_3^-$, $—NO_2$ and Me; q is an integer from 0 to 1; r is an integer from 0 to 2;

X is H, $C_{1-17}$alkyl-L-, $C_{2-17}$alkenyl-L-, or $C_{2-17}$alkynyl-L-; L is a direct link, amido, carboxy, carbonyl, carbamoyl, sulfonyl, carbamide, ureido, sulfonamide, hydrazinyl, hydrazide, semicarbazide, carbazate, thiocarbazate, isothiocarbazate or sulfonyl hydrazide;

Y' is a direct link; alkylene; a heterocyclylene group; or an acidic group such as a carboxylic acid (—COO—), sulfonic acid (—$S(O)_2O$—), sulfinic acid (—S(O)O—), phosphonic acid (—P(O)(OH)O—), phosphinic acid (—P(OH)O—) or boronicacid (—B(OH)O—); preferably a direct link, $C_{6-10}$alkylene, —$S(O)_2O$—,

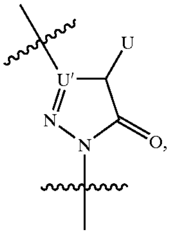

or

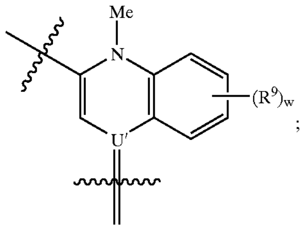

;

where U' is carbon and is attached to X; $R^9$ is $SO_3H$; w is an integer from 0 to 2; U is hydrogen, aryldiazo or heteroaryldiazo, preferably, hydrogen or phenyldiazo, more preferably H or

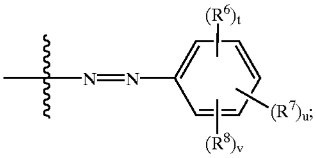

where $R^6$ is hydroxy or alkoxy, preferably OH; t is an integer from 0 to 3;

$R^7$ is alkoxy, preferably $C_{1-3}$alkoxy; u is an integer from 0 to 3; $R^8$ is halide or pseudohalide, preferably halide; v is an integer from 0 to 3;

Y is a direct link, $C_{1-4}$alkyl(W)(carboxy), $C_{2-4}$alkenyl(W)(carboxy), $C_{2-4}$alkynyl(W)(carboxy), $C_{1-4}$alkyl(W)(sulfo), $C_{2-4}$alkenyl(W)(sulfo) or $C_{2-4}$alkynyl(W)(sulfo); where W is H, amino or A-D-E-G, where A is $C_{1-4}$alkylene, $C_{2-4}$alkenylene or $C_{2-4}$alkynylene; D is a direct link, amido, ureido, imino, azido, carbamoyl, thio or thionyl; E is a direct link, $C_{1-3}$alkylene, arylene or heteroarylene; and G is H, amino, nitro, cyano, hydrazinyl, thio or sulfonamido.

In certain embodiments, the compounds for use in the compositions and methods provided herein have formula I:

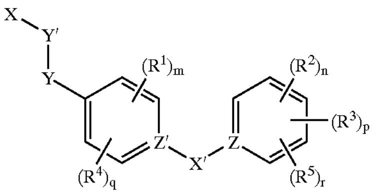

and pharmaceutically acceptable derivatives thereof, where X' is O, S, $(CH_2)_dO$ or $(CH_2)_dS$; d is an integer from 1 to 6; Z and Z' are each carbon;

$R^1$ is alkyl, aryl, alkoxy, haloalkyl, haloalkoxy, halide or pseudohalide, preferably halide, more preferably iodo; m is an integer from 0 to 4; $R^2$, $R^3$, n and p are selected from (i) and (ii) as follows:

(i) $R^2$ is alkyl, aryl, alkoxy, haloalkyl, haloalkoxy, halide or pseudohalide, preferably halide, more preferably iodo; n is an integer from 0 to 5; $R^3$ is hydroxy or alkoxy, preferably OH; p is an integer from 0 to 3; or (ii) n and p are 1; and $R^2$ and $R^3$ together form, with the carbon to which each is attached, an aryl, aromatic ring, heteroaromatic ring, carbocyclic or heterocyclic ring, which is saturated or unsaturated, containing from about 3 to about 16 members, preferably 3 to about 10 members, more preferably 5 to 7 members; in particular, $R^2$ and $R^3$ together form $-CH{=}CH-CH{=}CH-$, $-N{=}CH-CH{=}CH-$, $-CH{=}N-CH{=}CH-$, $-CH{=}CH-O-$, $-CH{=}CH-S-$ or $-CH{=}CH-N(R^{20})-$ where $R^{20}$ is alkyl, aryl or aralkyl;

$R^4$ and $R^5$ are each independently selected from $-SO_3^-$, $-NO_2$, alkyl, hydroxy, alkoxy, halide, pseudohalide; preferably $-SO_3$-, $-NO_2$ and lower alkyl; more preferably $-SO_3^-$, $-NO_2$ and Me; q is an integer from 0 to 1; r is an integer from 0 to 2;

X is H, $C_{1-17}$alkyl-L-, $C_{2-17}$alkenyl-L-, or $C_{2-17}$alkynyl-L-; L is a direct link, amido, carboxy, carbonyl, carbamoyl, sulfonyl, carbamide, ureido, sulfonamide, hydrazinyl, hydrazide, semicarbazide, carbazate, thiocarbazate, isothiocarbazate or sulfonyl hydrazide;

Y' is a direct link; alkylene; a heterocyclylene group; or an acidic group such as a carboxylic acid (—COO—), sulfonic acid ($-S(O)_2O-$), sulfinic acid (—S(O)O—), phosphonic acid (—P(O)(OH)O—), phosphinic acid (—P(OH)O—) or boronic acid (—B(OH)O—); preferably a direct link, $C_{6-10}$alkylene, $-S(O)_2O-$,

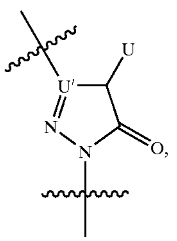
or
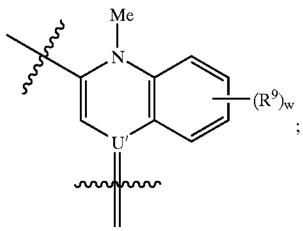
;

where U' is carbon and is attached to X; $R^9$ is $SO_3H$; w is an integer from 0 to 2; U is hydrogen, aryldiazo or heteroaryldiazo, preferably, hydrogen or phenyidiazo, more preferably H or

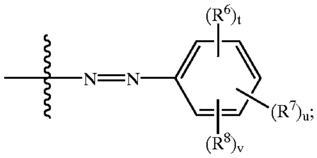
;

where $R^6$ is hydroxy or alkoxy, preferably OH; t is an integer from 0 to 3;

$R^7$ is alkoxy, preferably $C_{1-3}$alkoxy; u is an integer from 0 to 3; $R^8$ is halide or pseudohalide, preferably halide; v is an integer from 0 to 3;

Y is a direct link, $C_{1-14}$alkyl(W)(carboxy), $C_{2-4}$alkenyl(W)(carboxy), $C_{2-4}$alkynyl(W)(carboxy), $C_{1-4}$alkyl(W)(sulfo), $C_{2-4}$alkenyl(W)(sulfo) or $C_{2-4}$alkynyl(W)(sulfo); where W is H, amino or A-D-E-G, where A is $C_{1-4}$alkylene, $C_{2-4}$alkenylene or $C_{2-4}$alkynylene; D is a direct link, amido, ureido, imino, azido, carbamoyl, thio or thionyl; E is a direct link, $C_{1-3}$alkylene, arylene or heteroarylene; and G is H, amino, nitro, cyano, hydrazinyl, thio or sulfonamido.

In certain embodiments herein, the compounds are of formula I with the provisos that (i) if m, n or p are not 0, then q and r are 0; (ii) if q or r are not 0, then m, n and p are 0; (iii) if X is not H, then Y is a direct link; (iv) if Y is not a direct link, then Y' is a direct link; (v) if Y' is not a direct link, then Y is a direct link; (vi) if D is not a direct link, then G is H; (vii) if D is a single bond and G is not H, then E is a single bond; and (viii) if E is not a direct link or $C_{1-3}$alkylene, then G is H.

In other embodiments, the compounds are of formula I with the proviso that X—Y'—Y is not hydrogen.

In other embodiments, the compounds for use in the compositions and methods provided herein do not have thyroxine activity, or do not alter thyroxine secretion.

1. X' is O or S

In one embodiment, the compounds for use in the compositions and methods provided herein are aryl ethers and thioethers that have formula I:

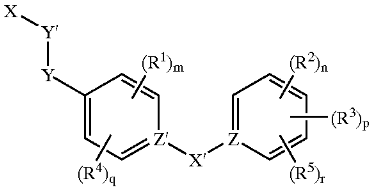

and pharmaceutically acceptable derivatives thereof, wherein X' is O or S; and the remaining variables are as described above.

In certain embodiments, the compounds have formula I, or are pharmaceutically acceptable derivatives thereof, wherein:

X' is O or S;

Z and Z' are each carbon;

$R^1$ is halide or pseudohalide, preferably halide, more preferably I and is preferably ortho to Z';

$R^2$ is halide or pseudohalide, preferably halide, more preferably I and is preferably meta to Z;

m is an integer from 0 to 4, preferably 2;

n is an integer from 0 to 4, preferably 2;

$R^3$ is OH and is preferably para to Z;

p is an integer from 0 to 3, preferably 1;

$R^4$ and $R^5$ are each independently selected from $-SO_3^-$, $-NO_2$ and Me; q is an integer from 0 to 1; r is an integer from 0 to 2;

X is H, $C_{1-17}$alkyl-L-, $C_{2-17}$alkenyl-L-, or $C_{2-17}$alkynyl-L-; L is a direct link, amido, carboxy, carbonyl, carbamoyl, sulfonyl, carbamide, ureido, sulfonamide, hydrazinyl, hydrazide, semicarbazide, carbazate, thiocarbazate, isothiocarbazate or sulfonyl hydrazide;

Y' is a direct link, $C_8$alkylene, $-S(O)_2O-$,

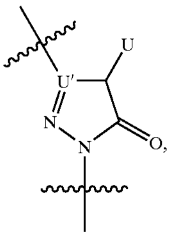
or
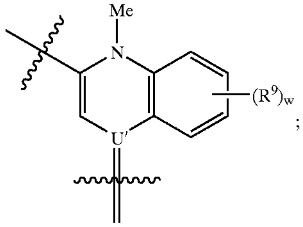
;

where U' is carbon and is attached to X; $R^9$ is $SO_3H$; w is an integer from 0 to 2; U is H or

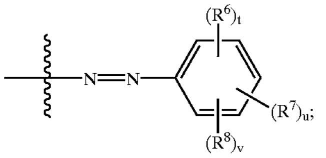

where $R^6$ is OH; t is an integer from 0 to 3; $R^7$ is $C_{1-3}$alkoxy; u is an integer from 0 to 3; $R^8$ is halo; v is an integer from 0 to 3;

Y is a direct link, $C_{1-4}$alkyl(W)(carboxy), $C_{2-4}$alkenyl(W)(carboxy), $C_{2-4}$alkynyl(W)(carboxy), $C_{1-4}$alkyl(W)(sulfo), $C_{2-4}$alkenyl(W)(sulfo) or $C_{2-4}$alkynyl(W)(sulfo); where W is H, amino or A-D-E-G, where A is $C_{1-4}$alkylene, $C_{2-4}$alkenylene or $C_{2-4}$alkynylene; D is a direct link, amido, ureido, imino, azido, carbamoyl, thio or thionyl; E is a direct link, $C_{1-3}$alkylene, arylene or heteroarylene; and G is H, amino, nitro, cyano, hydrazinyl, thio or sulfonamido;

with the provisos that (i) if m, n or p are not 0, then q and r are 0; (ii) if q or r are not 0, then m, n and p are 0; (iii) if X is not H, then Y is a direct link; (iv) if Y is not a direct link, then Y' is a direct link; (v) if Y' is not a direct link, then Y is a direct link; (vi) if D is not a direct link, then G is H; (vii) if D is a single bond and G is not H, then E is a single bond; and (viii) if E is not a direct link or $C_{1-3}$alkylene, then G is H.

a. Compounds Where m, n and p are 0

In a preferred embodiment, the compounds for use in the compositions and methods are of formula I, wherein m, n and p are 0. In this embodiment, the compounds are preferably sulfonic acid derivatives, more preferably arylsulfonic acid derivatives. In particular, the compounds of this embodiment are biphenyl ethers substituted on one of the phenyl rings with a sulfonic acid group or the sulfonic acid group may be linked to a heteroaryl substituent on one of the phenyl rings. Preferred compounds possess a sulfonic acid group, or pharmaceutically acceptable derivative thereof, ortho or para to the oxygen atom of the biphenyl ether moiety.

Compounds of this embodiment possess a $C_{8-17}$alkyl group, generally an n-$C_{10-17}$alkyl group, attached either directly to one of the phenyl rings of the biphenyl ether group or to the biphenyl ether moiety through a sulfonyloxy or heteroaryl substituent. Thus, the compounds of this embodiment are aliphatic arylsulfonates. In this embodiment, Y is preferably a direct link and X—Y' defines a substituent on the Z'-containing ring of the biphenyl ether moiety.

In preferred embodiments, the compounds are of formula I, or pharmaceutically acceptable derivatives thereof, wherein Z and Z' are each carbon; $R^4$ and $R^5$ are each independently selected from —$SO_3^-$, —$NO_2$ and Me; q is 0 or 1; r is an integer from 0 to 2; X is H, $C_{1-17}$alkyl-L-, $C_{2-17}$alkenyl-L-, or $C_{2-17}$alkynyl-L-; L is a direct link, amido, carboxy, carbonyl, carbamoyl, sulfonyl, carbamide, ureido, sulfonamide, hydrazinyl, hydrazide, semicarbazide, carbazate, thiocarbazate, isothiocarbazate or sulfonyl hydrazide; Y' is $C_8$alkylene, —$S(O)_2O$—,

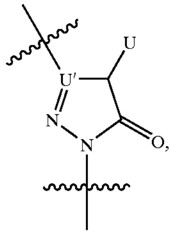

or

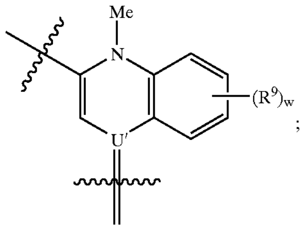

;

where U' is carbon and is attached to X; $R^9$ is $SO_3H$; w is an integer from 0 to 2, preferably 1; U is H or

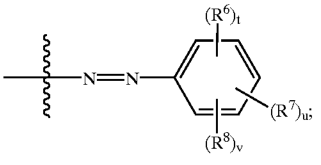

where $R^6$ is OH; t is an integer from 0 to 3, preferably 1; $R^7$ is $C_{1-3}$alkoxy; u is an integer from 0 to 3, preferably 0; $R^8$ is halo, preferably Cl; v is an integer from 0 to 3, preferably 1; and Y is a direct link.

In more preferred embodiments, the compounds are of formula I, or pharmaceutically acceptable derivatives thereof, wherein Z and Z' are each carbon; $R^4$ and $R^5$ are each independently selected from —$SO_3^-$, —$NO_2$ and Me; q is 0 or 1; r is an integer from 0 to 2; X is H or $C_{10-17}$alkyl-L-; L is a direct link, amido, or sulfonyl hydrazide; Y' is $C_8$alkylene, —$S(O)_2O$—,

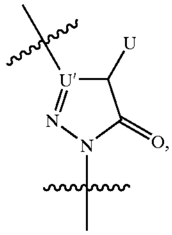

or

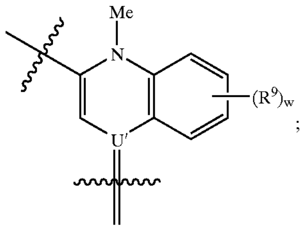

;

where U' is carbon and is attached to X; $R^9$ is $SO_3H$; w is 1; U is H or

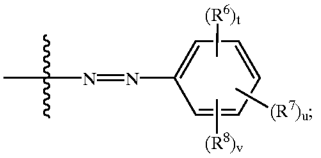

where $R^6$ is OH and is para to the diazo group; t is 1; u is 0; $R^8$ is Cl and is ortho to the diazo group; v is 1; and Y is a direct link.

In the embodiments described in detail above, X is preferably H, n-decyl, n-hexadecyl or n-heptadecyl. In other embodiments, r is 0; $R^4$ is $SO_3H$; and q is 1. In certain embodiments, q is 0; each $R^5$ is independently selected from $SO_3H$, $NO_2$ and Me; and r is 1 or 2.

b. Compounds Where q and r are 0

In another preferred embodiment, the compounds for use in the compositions and methods provided herein are of formula I, wherein q and r are 0. In this embodiment, the compounds are preferably carboxylic acid derivatives, and are substituted with $(CH_2)_bCOOH$ or $(CH_2)_bCH(W)$—(COOH), where b is 1 or 2; and W is as defined above. Preferred substituents are $CH_2COOH$, $(CH_2)_2COOH$ and $CH_2CH(NH_2)COOH$.

Thus, the compounds of this embodiment are thyroxine analogs and derivatives thereof. In these embodiments, Y' is preferably a direct link and X—Y defines the above carboxyl substituents on the Z'-containing ring of the biphenyl ether moiety.

In more preferred embodiments, the compounds have formula I, or are pharmaceutically acceptable derivatives thereof, wherein Z and Z' are each carbon; $R^1$ is I and is ortho to Z'; $R^2$ is I and is meta to Z; m is 1 or 2; n is 0, 1 or 2; $R^3$ is OH and is para to Z; p is 1; X is H; Y' is a direct link; and Y is $C_{1-4}$alkyl(W)(carboxy), $C_{2-4}$alkenyl(W)(carboxy), $C_{2-4}$alkynyl(W)(carboxy), $C_{1-4}$alkyl(W)(sulfo), $C_{2-4}$alkenyl(W)(sulfo) or $C_{2-4}$alkynyl(W)(sulfo); where W is H, amino or A-D-E-G, where A is $C_{1-4}$alkylene, $C_{2-4}$alkenylene or $C_{2-4}$alkynylene; D is a direct link, amido, ureido, imino, azido, carbamoyl, thio or thionyl; E is a direct link, $C_{1-3}$alkylene, arylene or heteroarylene; and G is H, amino, nitro, cyano, hydrazinyl, thio or sulfonamido.

In other more preferred embodiments, the compounds have formula I wherein Z and Z' are each carbon; $R^1$ is I and is ortho to Z'; $R^2$ is I and is meta to Z; m is 1 or 2; n is 0, 1 or 2; $R^3$ is OH and is para to Z; p is 1; X is H; Y' is a direct link; and Y is $(CH_2)_b$(carboxy) or $(CH_2)_bCH(W)$(carboxy), where b is 1 or 2; and W is as defined above.

In certain embodiments, the compounds have formula I with the provisos that (vi) if D is not a direct link, then G is H; (vii) if D is a single bond and G is not H, then E is a single bond; and (viii) if E is not a direct link or $C_{1-3}$alkylene, then G is H. In other embodiments, the compound is not L-thyroxine.

Preferred groups for X—Y are $CH_2COOH$, $(CH_2)_2COOH$ and $CH_2CH(NRR')COOH$, where R and R' are each independently hydrogen or an amino acid blocking or protecting group (see, e.g., Greene, T. W. *Protective Groups in Organic Synthesis* (1981) John Wiley & Sons, New York) including, but not limited to, tert-butoxycarbonyl (BOC), benzyloxycarbonyl (Cbz), 9-fluorenylmethoxycarbonyl (Fmoc), para-toluenesulfonyl (tosyl), 2,2,2-trichloroethoxycarbonyl, 2-trimethylsilylethoxycarbonyl, formyl, acetyl, benzyloxymethyl, benzyloxymethoxycarbonyl, unsubstituted or substituted benzoyl, unsubstituted or substituted benzyl, unsubstituted or substituted triphenylmethyl (trityl), or unsubstituted or substituted benzylidene; or R and R' together form phthaloyl, succinimidyl or maleimidyl. Thus, in particularly preferred embodiments, Z and Z' are each carbon; $R^1$ is I and is ortho to Z'; $R^2$ is I and is meta to Z; m is 1 or 2; n is 0, 1 or 2; $R^3$ is OH and is para to Z; p is 1; Y' is a direct link; and X—Y is $CH_2COOH$, $(CH_2)_2COOH$ or $CH_2CH(NH_2)COOH$.

2. X' is $(CH_2)_dO$ or $(CH_2)_dS$

In another embodiment, the compounds for use in the compositions and methods provided herein are aralkyl aryl, particularly benzyl phenyl, ethers and thioethers that have formula I:

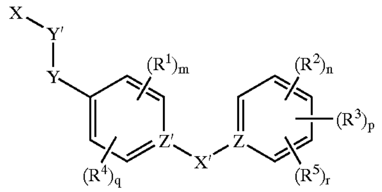

and pharmaceutically acceptable derivatives thereof, wherein:

X' is $(CH_2)_dO$ or $(CH_2)_dS$ where d is an integer from 1 to 6, preferably from 1 to 3, more preferably 1;

Z and Z' are each carbon;

$R^1$ is halide, pseudohalide, alkoxy or alkyl; particularly halide or pseudohalide, preferably halide, more preferably I, and is preferably ortho to Z';

$R^2$ and $R^3$ are selected from (i) or (ii) as follows:

(i) $R^2$ is halide, pseudohalide, alkyl, aryl, heteroaryl, cycloalkyl, alkoxy, aryloxy, heteroaryloxy, cycloalkoxy, haloalkyl or haloalkoxy, preferably halide, more preferably I, and is preferably meta or para to Z; m is an integer from 0 to 4, preferably 2; n is an integer from 0 to 5, preferably 1 or 5, more preferably 1; $R^3$ is OH and is preferably para to Z; p is an integer from 0 to 3, preferably 0 or 1, more preferably 0; or (ii) $R^2$ and $R^3$ together form —CH=CH—CH=CH—, —N=CH—CH=CH— or —CH=N—CH=CH—;

$R^4$ and $R^5$ are each independently selected from —$SO_3^-$, —$NO_2$ and Me; q is an integer from 0 to 1, preferably 0; r is an integer from 0 to 2, preferably 0;

X is H, $C_{1-17}$alkyl-L-, $C_{2-17}$alkenyl-L-, or $C_{2-17}$alkynyl-L-; L is a direct link, amido, carboxy, carbonyl, carbamoyl, sulfonyl, carbamide, ureido, sulfonamide, hydrazinyl, hydrazide, semicarbazide, carbazate, thiocarbazate, isothiocarbazate or sulfonyl hydrazide;

Y' is a direct link, $C_8$alkylene, —$S(O)_2O$—,

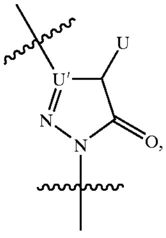

, or

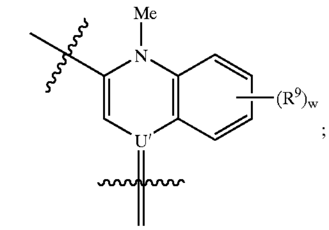

;

where U' is carbon and is attached to X; $R^9$ is $SO_3H$; w is an integer from 0 to 2; U is H or

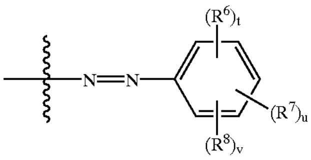

;

where $R^6$ is OH; t is an integer from 0 to 3; $R^7$ is $C_{1-3}$alkoxy; u is an integer from 0 to 3; $R^8$ is halo; v is an integer from 0 to 3;

Y is a direct link, $C_{1-4}$alkyl(W)(carboxy), $C_{2-4}$alkenyl(W)(carboxy), $C_{2-4}$alkynyl(W)(carboxy), $C_{1-4}$alkyl(W)

(sulfo), $C_{2-4}$alkenyl(W)(sulfo) or $C_{2-4}$alkynyl(W)(sulfo); where W is H, amino or A-D-E-G, where A is $C_{1-4}$alkylene, $C_{2-4}$alkenylene or $C_{2-4}$alkynylene; D is a direct link, amido, ureido, imino, azido, carbamoyl, thio or thionyl; E is a direct link, $C_{1-3}$alkylene, arylene or heteroarylene; and G is H, amino, nitro, cyano, hydrazinyl, thio or sulfonamido;

with the provisos that (i) if m, n or p are not 0, then q and r are 0; (ii) if q or r are not 0, then m, n and p are 0; (iii) if X is not H, then Y is a direct link; (iv) if Y is not a direct link, then Y' is a direct link; (v) if Y' is not a direct link, then Y is a direct link; (vi) if D is not a direct link, then G is H; (vii) if D is a single bond and G is not H, then E is a single bond; and (viii) if E is not a direct link or $C_{1-3}$alkylene, then G is H.

In certain embodiments herein, the compound is selected with the proviso that when X' is $CH_2O$, Y—Y'—X is COOH and m, r and q are 0, then at least one of n and p is not 0. In other embodiments, the compound is selected with the proviso that when m, r and q are 0, then at least one of n and p is not 0. In these embodiments, the aryl ring containing Z is substituted with at least one substituent selected from $R^2$ and $R^3$. In other embodiments, the compound is selected with the proviso that it is not 3,5-diiodo-4-(benzyloxy)benzoic acid.

In preferred embodiments, q and r are 0 and the compounds have formula II:

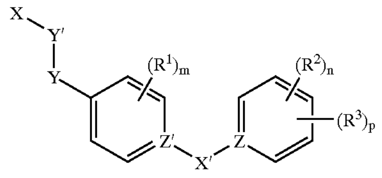

where X', Z, Z', Y, Y', X, $R^1$, $R^2$, $R^3$, m, n and p are as defined above.

In particular, Y' is a direct link, q and r are 0, and the compounds have formula III:

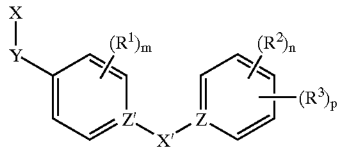

where X', Z, Z', Y, X, $R^1$, $R^2$, $R^3$, m, n and p are as defined above.

In other preferred embodiments, the compounds are of formula III where X' is $(CH_2)_dO$, where d is an integer from 1 to 6, preferably 1 to 3, more preferably 1; and Z, Z', Y, X, $R^1$, $R^2$, $R^3$, m, n and p are as defined above.

In particular, the compounds are of formula Ill, where X' is $CH_2O$. In these embodiments, X—Y is preferably $(CH_2)_aCOOH$ or $(CH_2)_cSO_3H$, more preferably $(CH_2)_aCOOH$, where a is an integer from 0 to 6, preferably 0 to 3, more preferably 0 or 2; and c is an integer from 0 to 4.

Thus, in more preferred embodiments, the compounds are substituted benzyl ethers of para-hydroxy substituted benzoic acids and para-hydroxyphenyl substituted alkanoic acids. In these embodiments, the compounds have formula IV:

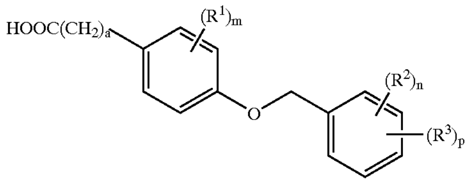

where $R^1$ is halide, pseudohalide, alkoxy or alkyl, particularly halide or pseudohalide, preferably halide, more preferably I; m is an integer from 0 to 4, preferably 2; a is an integer from 0 to 6, preferably from 0 to 3, more preferably 0 or 2; and $R^2$, $R^3$, n and p are selected as in (i) or (ii) as follows:

(i) $R^2$ is halide, pseudohalide, alkyl, aryl, heteroaryl, cycloalkyl, alkoxy, aryloxy, heteroaryloxy, cycloalkoxy, haloalkyl or haloalkoxy, preferably halide, more preferably I; n is an integer from 0 to 5, preferably 1 to 5, more preferably 1 or 5, most preferably 1; and p is 0; or (ii) n and p are 1, and $R^2$ and $R^3$ together form —CH═CH—CH═CH—, —N═CH—CH═CH—, —CH═N—CH═CH—, —CH═CH—O—, —CH═CH—S—, or —CH═CH—N($R^{20}$)—, where $R^{20}$ is alkyl, aryl or aralkyl.

In particularly preferred embodiments, $R^1$ is Cl, Br, or I, preferably I, and is ortho to the oxygen substituent; m is 2; $R^2$, $R^3$, n and p are selected from (i) or (ii) as follows:

(i) $R^2$ is selected from I, Br, $CH_3$, $C(CH_3)_3$, Ph, $OCH_3$, $CF_3$, $OCF_3$ or F; n is 1, or is 1 or 5 when $R^2$ is F; p is 0; or (ii) n and p are 1; and $R^2$ and $R^3$ together form —CH═CH—CH═CH—.

3. Preferred Compounds

Presently preferred compounds for use in the compositions and methods provided herein include:

5-[4,5-dihydro-5-oxo-3-[(1-oxooctadecyl)amino]-1H-pyrazol-1-yl]-2-phenoxybenzensulfonic acid, i.e.,

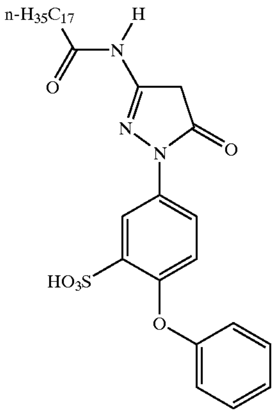

5-{4-[(2-chloro-4-hydroxyphenyl)azo]-3-octadecanamido-5-oxo-pyrazolin-1-yl}-2-phenoxybenzenesulfonic acid, i.e.,

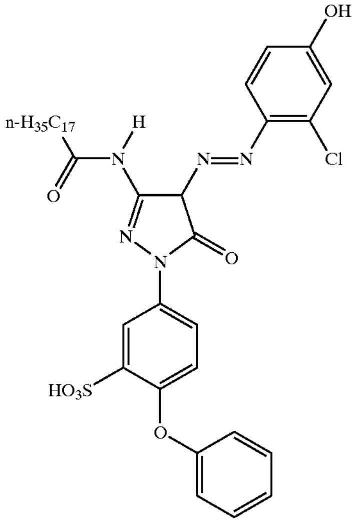

sodium 5-[4,5-dihydro-5-oxo-3-[(1-oxooctadecyl)amino]-1H-pyrazol-1-yl]-2-phenoxybenzensulfonate, i.e.,

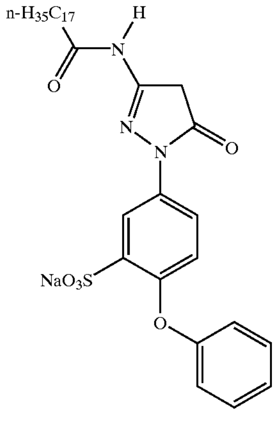

1-(3-sulfo-4-phenoxy)phenyl-3-heptadecylpyrazolin-5-one, i.e.,

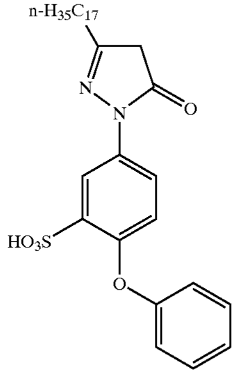

sodium 4-[4-(decyloxysulfonyl)phenyl]oxybenzenesulfonate, i.e.,

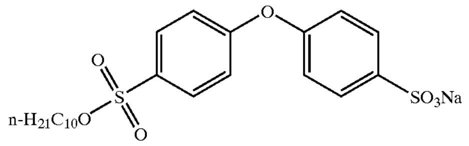

5-nitro-2-(4-(1,1,3,3-tetramethylbutyl)phenoxy)benzenesulfonic acid, i.e.,

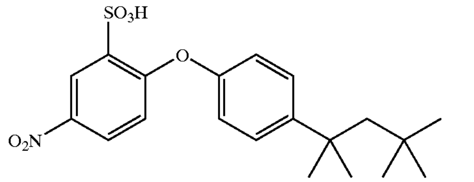

1-hexadecanesulfonic (1-methyl-6-sulfo-(2-(4-tolyloxy)phenyl)-4-quinolylidene)hydrazide, i.e.,

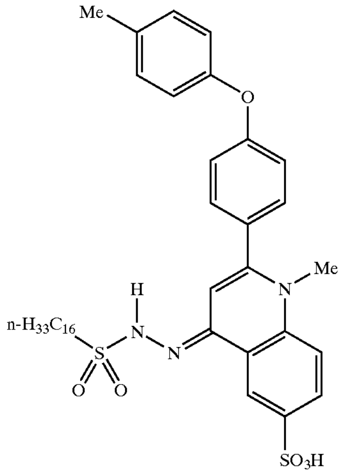

3,3,5,5'-tetraiodothyropropionic acid, i.e.,

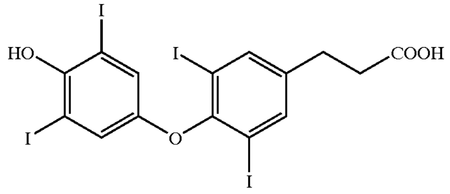

3,3',5-triiodothyroacetic acid, i.e.,

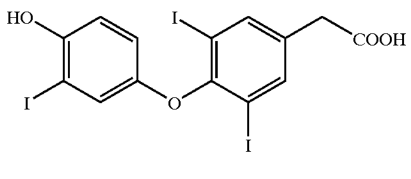

3,3',5,5'-tetraiodothyroacetic acid, i.e.,

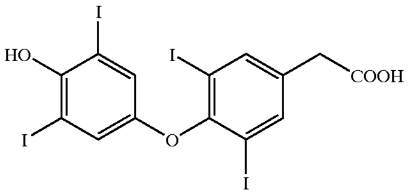

3,3',5-triiodothyropropionic acid, i.e.,

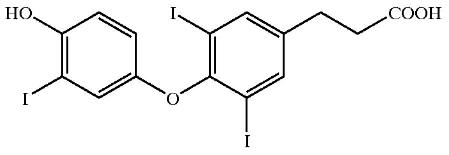

L-3,3',5'-triiodothyronine, i.e.,

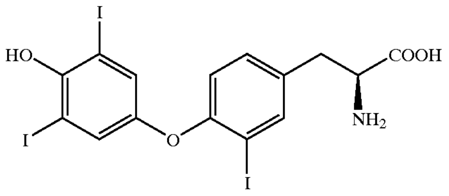

3,5-diiodothyropropionic acid, i.e.,

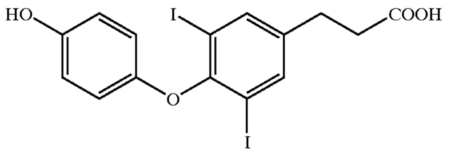

and L-thyroxine, i.e.,

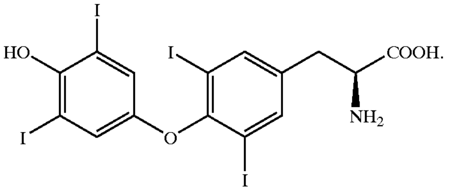

Preferred compounds exemplified herein for use in the compositions and methods provided herein include:

3,5-diiodo-4-(3-bromobenzyloxy)benzoic acid, i.e.,

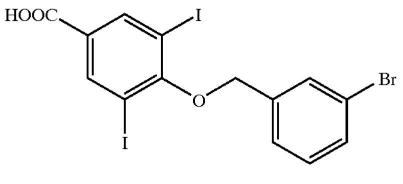

and 3-(3,5-diiodo-4-(3-iodobenzyloxy)phenyl)propionic acid, i.e.,

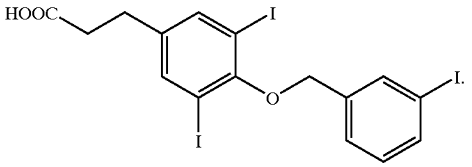

Other preferred compounds for use in the compositions and methods provided herein include 3,5-diiodo-4-(3-iodobenzyloxy)benzoic acid; 3,5-diiodo-4-(4-iodobenzyloxy)benzoic acid; 3,5-diiodo-4-(benzyloxy) benzoic acid; 3,5-diiodo-4-(2-bromobenzyloxy)benzoic acid; 3,5-diiodo-4-(4-bromobenzyloxy)benzoic acid; 3,5-diiodo-4-(2-methylbenzyloxy)benzoic acid; 3,5-diiodo-4-(3-methylbenzyloxy)benzoic acid; 3,5-diiodo-4-(4-methylbenzyloxy)benzoic acid; 3,5-diiodo-4-(4-tert-butylbenzyloxy)benzoic acid; 3,5-diiodo-4-(naphth-2-ylmethoxy)benzoic acid; 3,5-diiodo-4-(biphen-2-yloxy) benzoic acid; 3,5-diiodo-4-(3-methoxybenzyloxy)benzoic acid; 3,5-diiodo-4-(3-trifluoromethylbenzyloxy)benzoic acid; 3,5-diiodo-4-(3-trifluoromethoxybenzyloxy)benzoic acid; 3,5-diiodo-4-(3-fluorobenzyloxy)benzoic acid; 3,5-diiodo-4-(2,3,4,5,6-pentafluorophenylmethoxy)benzoic acid; 3-(3,5-diiodo-4-(4-iodobenzyloxy)phenyl)propionic acid; 3-(3,5-diiodo-4-(benzyloxy)phenyl)propionic acid; 3-(3,5-diiodo-4-(3-bromobenzyloxy)phenyl)propionic acid; 3,5-dibromo-4-(3-iodobenzyloxy)-benzoic acid; 3,5-dichloro-4-(3-iodobenzyloxy)benzoic acid; and 3-(3,5-diiodo-4-(4-bromobenzyloxy)phenyl)propionic acid.

C. Preparation of the Compounds

The preparation of the above compounds is described below. Any such compound or similar compound may be synthesized according to a method discussed in general below or by only minor modification of the methods by selecting appropriate starting materials. Additionally, certain compounds described herein may be obtained from commercial sources known to those of skill in the art (see, e.g., Aldrich Chemical Company, Milwaukee, Wis.; Sigma, St. Louis, Mo.; Fluka Chemical Corp., Milwaukee, Wis.).

Certain compounds, such as biphenyl ether sulfonic acids, provided herein may be prepared by methods well known to those of skill in the art. For example, sulfonation of the biphenyl ether nucleus using, e.g., concentrated sulfuric acid, fuming sulfuric acid, $SO_3$ or $ClSO_3H$ is well known (see, e.g., Nelson, in Olah, "Friedel-Crafts and Related Reactions", vol. 3, pp. 1355–1392, Interscience, New York, (1964) and Gilbert "Sulfonation and Related Reactions", pp 62–83 and 87–124, Interscience, New York (1965)). Sulfonation will occur preferentially at the positions ortho and para to the oxygen atom. Sulfonation of diphenyl ether with $SO_2Cl_2$ provides a bis(sulfonyl chloride). Reaction of this derivative with one equivalent of an alcohol, e.g., decanol, provides a monosulfonic ester-sulfonic acid derivative. Nitration (by treatment with, e.g., concentrated nitric and sulfuric acids, or with a mixture of nitric acid and water, acetic acid or acetic anhydride, see, e.g, Olah and Kuhn, in Olah, "Friedel-Crafts and Related Reactions", vol. 3, pp. 1355–1392, Interscience, New York (1964)) and Friedel-Crafts alkylation (by treatment with, e.g., an alkene and a catalyst such as $AlCl_3$ or a mineral acid (i.e., sulfuric acid), see, e.g., Bonvino et al. (1981) *Tetrahedron* 37:615)) of diaryl ethers are also well known, and also provides ortho and para substitution. Thus, nitration, alkylation and sulfonation of a diaryl ether can be used to prepare certain compounds provided herein.

Alternatively, reaction of a chloro-substituted arylsulfonic acid with an aryloxy anion gives the diaryl ether sulfonic acids provided herein. For example, reaction of 5-nitro-2-chlorobenzenesulfonic acid with sodium phenoxylate affords 4-nitro-2-sulfodiphenyl ether. Other compounds provided herein may be prepared by appropriate choice of starting materials.

Certain of the compounds provided herein 1-aryl-3-amino-5-pyrazolone derivatives. These compounds are well known to those of skill in the art (see, e.g., British Patent Specification 1209945). The compounds may be prepared by reaction of the appropriate arylhydrazine with a compound of formula $H_2NC(O)CH_2COOR$ or RC(O)NHC(O) $CH_2CO_{13}OR$ with loss of ROH and water to provide the desired compounds (see, e.g., March, "Advanced Organic Chemistry", 3rd ed., p. 804, John Wiley & Sons, Inc., New York (1985)). Alternatively, reaction of the arylhydrazine with α-cyanoacetate provides a 1-aryl-3-amino-5-pyrazolone. Acylation of the amino group affords the compounds provided herein.

Other compounds provided herein are 1-aryl-3-amino-4-(aryldiazo)-5-pyazolone derivatives. These compounds are also well known to those of skill in the art (see, e.g., British Patent Specification 1209945). Reaction of the above 1-aryl-3-amino-5-pyrazolone compounds with a diazatized aniline derivative affords the desired 4-aryldiazo derivatives.

Further compounds provided herein include alkylsulfonylhydrazone derivatives of 4-quinolones. These compounds are well known in the art (see, e.g., International Patent Application Publication No. WO 94/07492). Preparation of these compounds may be achieved by reaction of the appropriate quinolone with the corresponding alkylsulfonylhydrazide. The requisite quinolone derivatives may be prepared by standard methods.

Other compounds provided herein may be prepared by the methods described in International Patent Application Publication No. WO 96/11904, Evans et al. ((1998) *Tetrahedron Lett.* 39(19):2937–2940), Salamonczyk et al.((1997) *Tetrahedron Lett.* 38(40):6965–6968, and Bell et al. ((1997) *Can. J. Chem.* 75(6):873–883, or minor modifications of these methods. These references are incorporated by reference, herein in their entirety.

Briefly, iodination of tyrosine with by treatment with, for example, NaI and $NaIO_3$ in acetic acid, followed by $NaHSO_3$ to remove excess $I_2$ provides a tyrosine derivative that is iodinated at one or both of the positions ortho to the hydroxyl group. Protection of the amino functionality by, e.g., acetylation with acetic anhydride, followed by esterification of the carboxyl group with, e.g., ethanol and an acid catalyst, e.g., sulfuric acid, provides an iodinated derivative of N-acetyltyrosine ethyl ester. Oxidative coupling of, this iodinated derivative using air under pressure of 20 atmospheres with $MnSO_4$ and $H_3BO_4$ in ethanol with a piperidine additive affords an N-acetylthyroxine ethyl ester derivative. Hydrolysis of the N-acetyl group and the ethyl ester with HCl and acetic acid provides the desired thyroxine derivative.

Alternatively, the compounds provided herein may be synthesized by copper(II)-promoted coupling of arylboronic acids and phenols. Briefly, an iodinated tyrosine derivative, as described above, may be coupled with an arylboronic acid by reaction with $Cu(OAc)_2$ in the presence of powdered 4 Å molecular sieves at ambient temperature. Addition of an amine base, such as triethylamine, and chromatographic purification provides the desired diaryl ether derivative.

As a further alternative, the thyroxine derivatives provided herein may be synthesized from a para-hydroxybenzyl alcohol, or iodinated derivatives thereof. Reaction of the para-hydroxybenzyl alcohol with $NaBiO_3$ (2 equiv.) in ethyl acetate/acetic acid/water provides the corresponding 4-oxocyclohexadienylidene epoxide (e.g., 1-oxa-spiro[2,5] bicycloocta-4,7-dien-6-one). Reaction of this compound with tyrosine, or an iodinated derivative thereof, in dimethyl formamide at pH=8 in borate buffer affords the desired thyroxine and thyroxine derivatives.

Still other compounds provided herein are benzyl ether derivatives of phenolic carboxylic acids. These compounds may be prepared by reaction of one equivalent of the phenolic carboxylic acid with 2.5 equivalents of the desired benzyl halide and three equivalents of cesium carbonate in dimethylformamide. The resulting benzyl ether-ester is saponified using LiOH in water/tetrahydrofuran to afford the benzyl ether-carboxylic acid derivatives provided herein.

D. Formulation of Pharmaceutical Compositions

The pharmaceutical compositions provided herein contain therapeutically effective amounts of one or more PAI antagonists of formula I that are useful in the prevention, treatment, or amelioration of one or more of the symptoms of thrombotic disorders, including, but not limited to, myocardial infarction, deep vein thrombosis and disseminated intravascular coagulation, and cancer, including, but not limited to, tumors, metastatic solid tumors and breast cancer. The compositions contain one or more substituted biaryl ethers that possess at least one acidic moiety, including, but not limited to, a carboxylic acid, sulfonic acid, sulfinic acid, phosphonic acid, phosphinic acid or boronic acid group.

The compounds are preferably formulated into suitable pharmaceutical preparations such as solutions, suspensions, tablets, dispersible tablets, pills, capsules, powders, sustained release formulations or elixirs, for oral administration or in sterile solutions or suspensions for parenteral administration, as well as transdermal patch preparation and dry powder inhalers. Typically the compounds described above are formulated into pharmaceutical compositions using techniques and procedures well known in the art (see, e.g., Ansel *Introduction to Pharmaceutical Dosage Forms, Fourth Edition* 1985, 126).

In the compositions, effective concentrations of one or more compounds or pharmaceutically acceptable derivatives is (are) mixed with a suitable pharmaceutical carrier or vehicle. The compounds may be derivatized as the corresponding salts, esters, enol ethers or esters, acids, bases, solvates, hydrates or prodrugs prior to formulation, as described above. The concentrations of the compounds in the compositions are effective for delivery of an amount, upon administration, that ameliorates one or more of the symptoms of thrombotic disorders, including, but not limited to, myocardial infarction, deep vein thrombosis and disseminated intravascular coagulation, and cancer, including, but not limited to, tumors, metastatic solid tumors and breast cancer. Typically, the compositions are formulated for single dosage administration. To formulate a composition, the weight fraction of compound is dissolved, suspended, dispersed or otherwise mixed in a selected vehicle at an effective concentration such that the treated condition is relieved or ameliorated. Pharmaceutical carriers or vehicles suitable for administration of the compounds provided herein include any such carriers known to those skilled in the art to be suitable for the particular mode of administration.

In addition, the compounds may be formulated as the sole pharmaceutically active ingredient in the composition or may be combined with other active ingredients. Liposomal suspensions, including tissue-targeted liposomes, particularly tumor-targeted liposomes, may also be suitable as pharmaceutically acceptable carriers. These may be prepared according to methods known to those skilled in the art. For example, liposome formulations may be prepared as described in U.S. Pat. No. 4,522,811.

The active compound is included in the pharmaceutically acceptable carrier in an amount sufficient to exert a therapeutically useful effect in the absence of undesirable side effects on the patient treated. The therapeutically effective concentration may be determined empirically by testing the compounds in known in vitro and in vivo systems (see, e.g., Nilsson (1987) *Fibrinolysis* 1:163–168; U.S. Pat. Nos. 5,750,530, 5,902,812, 5,891,877; Charlton et al. (1996) *Thrombosis and Haemostasis* 75(5):808–815; Charlton et al. (1997) *Fibrinolysis and Proteolysis* 11(1):51–56; Bjorquist et al. (1998) *Biochemistry* 37:1227–1234) and then extrapolated therefrom for dosages for humans.

The concentration of active compound in the pharmaceutical composition will depend on absorption, inactivation and excretion rates of the active compound, the physicochemical characteristics of the compound, the dosage schedule, and amount administered as well as other factors known to those of skill in the art. For example, the amount that is delivered is sufficient to ameliorate one or more of the symptoms of thrombotic disorders, including, but not limited to, myocardial infarction, deep vein thrombosis and disseminated intravascular coagulation, and cancer, including, but not limited to, tumors, metastatic solid tumors and breast cancer.

Typically a therapeutically effective dosage should produce a serum concentration of active ingredient of from about 0.1 ng/ml to about 50–100 $\mu$g/ml. The pharmaceutical compositions typically should provide a dosage of from about 0.001 mg to about 2000 mg of compound per kilogram of body weight per day. Pharmaceutical dosage unit forms are prepared to provide from about 1 mg to about 1000 mg and preferably from about 10 to about 500 mg of the essential active ingredient or a combination of essential ingredients per dosage unit form.

The active ingredient may be administered at once, or may be divided into a number of smaller doses to be administered at intervals of time. It is understood that the precise dosage and duration of treatment is a function of the disease being treated and may be determined empirically using known testing protocols or by extrapolation from in vivo or in vitro test data. It is to be noted that concentrations and dosage values may also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed compositions.

Preferred pharmaceutically acceptable derivatives include acids, bases, enol ethers and esters, salts, esters, hydrates, solvates and prodrug forms. The derivative is selected such that its pharmacokinetic properties are superior to the corresponding neutral compound.

Thus, effective concentrations or amounts of one or more of the compounds described herein or pharmaceutically acceptable derivatives thereof are mixed with a suitable pharmaceutical carrier or vehicle for systemic, topical or local administration to form pharmaceutical compositions. Compounds are included in an amount effective for ameliorating one or more symptoms of, or for treating or preventing thrombotic disorders, including, but not limited to, myocardial infarction, deep vein thrombosis and disseminated intravascular coagulation, and cancer, including, but not limited to, tumors, metastatic solid tumors and breast cancer. The concentration of active compound in the composition will depend on absorption, inactivation, excretion rates of the active compound, the dosage schedule, amount administered, particular formulation as well as other factors known to those of skill in the art.

The compositions are intended to be administered by a suitable route, including orally, parenterally, rectally, topically and locally. For oral administration, capsules and tablets are presently preferred. The compositions are in liquid, semi-liquid or solid form and are formulated in a manner suitable for each route of administration. Preferred modes of administration include parenteral and oral modes of administration. Oral administration is presently most preferred.

Solutions or suspensions used for parenteral, intradermal, subcutaneous, or topical application can include any of the following components: a sterile diluent, such as water for injection, saline solution, fixed oil, polyethylene glycol, glycerine, propylene glycol or other synthetic solvent; antimicrobial agents, such as benzyl alcohol and methyl parabens; antioxidants, such as ascorbic acid and sodium bisulfite; chelating agents, such as ethylenediaminetetraacetic acid (EDTA); buffers, such as acetates, citrates and phosphates; and agents for the adjustment of tonicity such as sodium chloride or dextrose. Parenteral preparations can be enclosed in ampules, disposable syringes or single or multiple dose vials made of glass, plastic or other suitable material.

In instances in which the compounds exhibit insufficient solubility, methods for solubilizing compounds may be used. Such methods are known to those of skill in this art, and include, but are not limited to, using cosolvents, such as dimethylsulfoxide (DMSO), using surfactants, such as TWEEN®, or dissolution in aqueous sodium bicarbonate. Derivatives of the compounds, such as prodrugs of the compounds may also be used in formulating effective pharmaceutical compositions.

Upon mixing or addition of the compound(s), the resulting mixture may be a solution, suspension, emulsion or the like. The form of the resulting mixture depends upon a number of factors, including the intended mode of administration and the solubility of the compound in the selected carrier or vehicle. The effective concentration is sufficient for ameliorating the symptoms of the disease, disorder or condition treated and may be empirically determined.

The pharmaceutical compositions are provided for administration to humans and animals in unit dosage forms, such as tablets, capsules, pills, powders, granules, sterile parenteral solutions or suspensions, and oral solutions or suspensions, and oil-water emulsions containing suitable quantities of the compounds or pharmaceutically acceptable derivatives thereof. The pharmaceutically therapeutically active compounds and derivatives thereof are typically formulated and administered in unit-dosage forms or multiple-dosage forms. Unit-dose forms as used herein refers to physically discrete units suitable for human and animal subjects and packaged individually as is known in the art. Each unit-dose contains a predetermined quantity of the therapeutically active compound sufficient to produce the desired therapeutic effect, in association with the required pharmaceutical carrier, vehicle or diluent. Examples of unit-dose forms include ampoules and syringes and individually packaged tablets or capsules. Unit-dose forms may be administered in fractions or multiples thereof. A multiple-dose form is a plurality of identical unit-dosage forms packaged in a single container to be administered in segregated unit-dose form. Examples of multiple-dose forms include vials, bottles of tablets or capsules or bottles of pints or gallons. Hence, multiple dose form is a multiple of unit-doses which are not segregated in packaging.

The composition can contain along with the active ingredient: a diluent such as lactose, sucrose, dicalcium phosphate, or carboxymethylcellulose; a lubricant, such as magnesium stearate, calcium stearate and talc; and a binder such as starch, natural gums, such as gum acaciagelatin, glucose, molasses, polvinylpyrrolidine, celluloses and derivatives thereof, povidone, crospovidones and other such binders known to those of skill in the art. Liquid pharmaceutically administrable compositions can, for example, be prepared by dissolving, dispersing, or otherwise mixing an active compound as defined above and optional pharmaceutical adjuvants in a carrier, such as, for example, water, saline, aqueous dextrose, glycerol, glycols, ethanol, and the like, to thereby form a solution or suspension. If desired, the pharmaceutical composition to be administered may also contain minor amounts of nontoxic auxiliary substances such as wetting agents, emulsifying agents, or solubilizing agents, pH buffering agents and the like, for example, acetate, sodium citrate, cyclodextrine derivatives, sorbitan monolaurate, triethanolamine sodium acetate, triethanolamine oleate, and other such agents. Actual methods of preparing such dosage forms are known, or will be apparent, to those skilled in this art; for example, see Remington's Pharmaceutical Sciences, Mack Publishing Company, Easton, Pa., 15th Edition, 1975. The composition or formulation to be administered will, in any event, contain a quantity of the active compound in an amount sufficient to alleviate the symptoms of the treated subject.

Dosage forms or compositions containing active ingredient in the range of 0.005% to 100% with the balance made up from non-toxic carrier may be prepared. For oral administration, a pharmaceutically acceptable non-toxic composition is formed by the incorporation of any of the normally employed excipients, such as, for example pharmaceutical grades of mannitol, lactose, starch, magnesium stearate, talcum, cellulose derivatives, sodium crosscarmellose, glucose, sucrose, magnesium carbonate or sodium saccharin. Such compositions include solutions, suspensions, tablets, capsules, powders and sustained release formulations, such as, but not limited to, implants and microencapsulated delivery systems, and biodegradable, biocompatible polymers, such as collagen, ethylene vinyl acetate, polyanhydrides, polyglycolic acid, polyorthoesters, polylactic acid and others. Methods for preparation of these compositions are known to those skilled in the art. The contemplated compositions may contain 0.001%–100% active ingredient, preferably 0.1–8.5%, typically 75–95%.

The active compounds or pharmaceutically acceptable derivatives may be prepared with carriers that protect the compound against rapid elimination from the body, such as time release formulations or coatings.

The compositions may include other active compounds to obtain desired combinations of properties. The compounds of formula I, or pharmaceutically acceptable derivatives thereof as described herein, may also be advantageously administered for therapeutic or prophylactic purposes together with another pharmacological agent known in the general art to be of value in treating one or more of the diseases or medical conditions referred to hereinabove, such as beta-adrenergic blocker (for example atenolol), a calcium channel blocker (for example nifedipine), an angiotensin converting enzyme (ACE) inhibitor (for example lisinopril), a diuretic (for example furosemide or hydrochlorothiazide), an endothelin converting enzyme (ECE) inhibitor (for example phosphoramidon), a neutral endopeptidase (NEP) inhibitor, an HMGCoA reductase inhibitor, a nitric oxide donor, an anti-oxidant, a vasodilator, a dopamine agonist, a neuroprotective agent, a steroid, a beta-agonist, an anti-coagulant, or a thrombotic agent. It is to be understood that such combination therapy constitutes a further aspect of the compositions and methods of treatment provided herein.

1. Compositions for Oral Administration

Oral pharmaceutical dosage forms are either solid, gel or liquid. The solid dosage forms are tablets, capsules, granules, and bulk powders. Types of oral tablets include compressed, chewable lozenges and tablets which may be enteric-coated, sugar-coated or film-coated. Capsules may be hard or soft gelatin capsules, while granules and powders may be provided in non-effervescent or effervescent form with the combination of other ingredients known to those skilled in the art.

In certain embodiments, the formulations are solid dosage forms, preferably capsules or tablets. The tablets, pills, capsules, troches and the like can contain any of the following ingredients, or compounds of a similar nature: a binder; a diluent; a disintegrating agent; a lubricant; a glidant; a sweetening agent; and a flavoring agent.

Examples of binders include microcrystalline cellulose, gum tragacanth, glucose solution, acacia mucilage, gelatin solution, sucrose and starch paste. Lubricants include talc, starch, magnesium or calcium stearate, lycopodium and stearic acid. Diluents include, for example, lactose, sucrose, starch, kaolin, salt, mannitol and dicalcium phosphate. Glidants include, but are not limited to, colloidal silicon dioxide. Disintegrating agents include crosscarmellose sodium, sodium starch glycolate, alginic acid, corn starch, potato starch, bentonite, methylcellulose, agar and carboxymethylcellulose. Coloring agents include, for example, any of the approved certified water soluble FD and C dyes, mixtures thereof; and water insoluble FD and C dyes suspended on alumina hydrate. Sweetening agents include sucrose, lactose, mannitol and artificial sweetening agents such as saccharin, and any number of spray dried flavors. Flavoring agents include natural flavors extracted from plants such as fruits and synthetic blends of compounds which produce a pleasant sensation, such as, but not limited to peppermint and methyl salicylate. Wetting agents include propylene glycol monostearate, sorbitan monooleate, diethylene glycol monolaurate and polyoxyethylene laural ether. Emetic-coatings include fatty acids, fats, waxes, shellac, ammoniated shellac and cellulose acetate phthalates. Film coatings include hydroxyethylcellulose, sodium carboxymethylcellulose, polyethylene glycol 4000 and cellulose acetate phthalate.

If oral administration is desired, the compound could be provided in a composition that protects it from the acidic environment of the stomach. For example, the composition can be formulated in an enteric coating that maintains its integrity in the stomach and releases the active compound in the intestine. The composition may also be formulated in combination with an antacid or other such ingredient.

When the dosage unit form is a capsule, it can contain, in addition to material of the above type, a liquid carrier such as a fatty oil. In addition, dosage unit forms can contain various other materials which modify the physical form of the dosage unit, for example, coatings of sugar and other enteric agents. The compounds can also be administered as a component of an elixir, suspension, syrup, wafer, sprinkle, chewing gum or the like. A syrup may contain, in addition to the active compounds, sucrose as a sweetening agent and certain preservatives, dyes and colorings and flavors.

The active materials can also be mixed with other active materials which do not impair the desired action, or with materials that supplement the desired action, such as antacids, H2 blockers, and diuretics. The active ingredient is a compound or pharmaceutically acceptable derivative thereof as described herein. Higher concentrations, up to about 98% by weight of the active ingredient may be included.

Pharmaceutically acceptable carriers included in tablets are binders, lubricants, diluents, disintegrating agents, coloring agents, flavoring agents, and wetting agents. Enteric-coated tablets, because of the enteric-coating, resist the action of stomach acid and dissolve or disintegrate in the neutral or alkaline intestines. Sugar-coated tablets are compressed tablets to which different layers of pharmaceutically acceptable substances are applied. Film-coated tablets are compressed tablets which have been coated with a polymer or other suitable coating. Multiple compressed tablets:are compressed tablets made by more than one compression cycle utilizing the pharmaceutically acceptable substances previously mentioned. Coloring agents may also be used in the above dosage forms. Flavoring and sweetening agents are used in compressed tablets, sugar-coated, multiple compressed and chewable tablets. Flavoring and sweetening agents are especially useful in the formation of chewable tablets and lozenges.

Liquid oral dosage forms include aqueous solutions, emulsions, suspensions, solutions and/or suspensions reconstituted from non-effervescent granules and effervescent preparations reconstituted from effervescent granules. Aqueous solutions include, for example, elixirs and syrups. Emulsions are either oil-in-water or water-in-oil.

Elixirs are clear, sweetened, hydroalcoholic preparations. Pharmaceutically acceptable carriers used in elixirs include solvents. Syrups are concentrated aqueous solutions of a sugar, for example, sucrose, and may contain a preservative. An emulsion is a two-phase system in which one liquid is dispersed in the form of small globules throughout another liquid. Pharmaceutically acceptable carriers used in emulsions are non-aqueous liquids, emulsifying agents and preservatives. Suspensions use pharmaceutically acceptable suspending agents and preservatives. Pharmaceutically acceptable substances used in non-effervescent granules, to be reconstituted into a liquid oral dosage form, include diluents, sweeteners and wetting agents. Pharmaceutically acceptable substances used in effervescent granules, to be reconstituted into a liquid oral dosage form, include organic acids and a source of carbon dioxide. Coloring and flavoring agents are used in all of the above dosage forms.

Solvents include glycerin, sorbitol, ethyl alcohol and syrup. Examples of preservatives include glycerin, methyl and propylparaben, benzoic add, sodium benzoate and alcohol. Examples of non-aqueous liquids utilized in emulsions include mineral oil and cottonseed oil. Examples of emulsifying agents include gelatin, acacia, tragacanth, bentonite, and surfactants such as polyoxyethylene sorbitan monooleate. Suspending agents include sodium carboxymethylcellulose, pectin, tragacanth, Veegum and acacia. Diluents include lactose and sucrose. Sweetening agents include sucrose, syrups, glycerin and artificial sweetening agents such as saccharin. Wetting agents include propylene glycol monostearate, sorbitan monooleate, diethylene glycol monolaurate and polyoxyethylene lauryl ether. Organic adds include citric and tartaric acid. Sources of carbon dioxide include sodium bicarbonate and sodium carbonate. Coloring agents include any of the approved certified water soluble FD and C dyes, and mixtures thereof. Flavoring agents include natural flavors extracted from plants such fruits, and synthetic blends of compounds which produce a pleasant taste sensation.

For a solid dosage form, the solution or suspension, in for example propylene carbonate, vegetable oils or triglycerides, is preferably. encapsulated in a gelatin capsule. Such solutions, and the preparation and encapsulation thereof, are disclosed in U.S. Pat. Nos. 4,328,245; 4,409,239; and 4,410,545. For a liquid dosage form, the solution, e.g., for example, in a polyethylene glycol, may be diluted with a sufficient quantity of a pharmaceutically acceptable liquid carrier, e.g., water, to be easily measured for administration.

Alternatively, liquid or semi-solid oral formulations may be prepared by dissolving or dispersing the active compound or salt in vegetable oils, glycols, triglycerides, propylene glycol esters (e.g., propylene carbonate) and other such carriers, and encapsulating these solutions or suspensions in hard or soft gelatin capsule shells. Other useful formulations include those set forth in U.S. Pat. Nos. Re 28,819 and 4,358,603.

In all embodiments, tablets and capsules formulations may be coated as known by those of skill in the art in order to modify or sustain dissolution of the active ingredient. Thus, for example, they may be coated with a conventional enterically digestible coating, such as phenylsalicylate, waxes and cellulose acetate phthalate.

2. Injectables, Solutions and Emulsions

Parenteral administration, generally characterized by injection, either subcutaneously, intramuscularly or intravenously is also contemplated herein. Injectables can be prepared in conventional forms, either as liquid solutions or suspensions, solid forms suitable for solution or suspension in liquid prior to injection, or as emulsions. Suitable excipients are, for example, water, saline, dextrose, glycerol or ethanol. In addition, if desired, the pharmaceutical compositions to be administered may also contain minor amounts of non-toxic auxiliary substances such as wetting or emulsifying agents, pH buffering agents, stabilizers, solubility enhancers, and other such agents, such as for example, sodium acetate, sorbitan monolaurate, triethanolamine oleate and cyclodextrins. Implantation of a slow-release or sustained-release system, such that a constant level of dosage is maintained (see, e.g., U.S. Pat. No. 3,710,795) is also contemplated herein. The percentage of active compound contained in such parenteral compositions is highly dependent on the specific nature thereof, as well as the activity of the compound and the needs of the subject.

Parenteral administration of the compositions includes intravenous, subcutaneous and intramuscular administrations. Preparations for parenteral administration include sterile solutions ready for injection, sterile dry soluble products, such as lyophilized powders, ready to be combined with a solvent just prior to use, including hypodermic tablets, sterile suspensions ready for injection, sterile dry insoluble products ready to be combined with a vehicle just prior to use and sterile emulsions. The solutions may be either aqueous or nonaqueous.

If administered intravenously, suitable carriers include physiological saline or phosphate buffered saline (PBS), and solutions containing thickening and solubilizing agents, such as glucose, polyethylene glycol, and polypropylene glycol and mixtures thereof.

Pharmaceutically acceptable carriers used in parenteral preparations include aqueous vehicles, nonaqueous vehicles, antimicrobial agents, isotonic agents, buffers, antioxidants, local anesthetics, suspending and dispersing agents, emulsifying agents, sequestering or chelating agents and other pharmaceutically acceptable substances.

Examples of aqueous vehicles include Sodium Chloride Injection, Ringers Injection, Isotonic Dextrose Injection, Sterile Water Injection, Dextrose and Lactated Ringers Injection. Nonaqueous parenteral vehicles include fixed oils of vegetable origin, cottonseed oil, corn oil, sesame oil and peanut oil. Antimicrobial agents in bacteriostatic or fungistatic concentrations must be added to parenteral preparations packaged in multiple-dose containers which include phenols or cresols, mercurials, benzyl alcohol, chlorobutanol, methyl and propyl p-hydroxybenzoic acid esters, thimerosal, benzalkonium chloride and benzethonium chloride. Isotonic agents include sodium chloride and dextrose. Buffers include phosphate and citrate. Antioxidants include sodium bisulfate. Local anesthetics include procaine hydrochloride. Suspending and dispersing agents include sodium carboxymethylcelluose, hydroxypropyl methylcellulose.and polyvinylpyrrolidone. Emulsifying agents include Polysorbate 80 (TWEEN® 80). A sequestering or chelating agent of metal ions include EDTA. Pharmaceutical carriers also include ethyl alcohol, polyethylene glycol and propylene glycol for water miscible vehicles and sodium hydroxide, hydrochloric acid, citric acid or lactic acid for pH adjustment.

The concentration of the pharmaceutically active compound is adjusted so that an injection provides an effective amount to produce the desired pharmacological effect. The exact dose depends on the age, weight and condition of the patient or animal as is known in the art.

The unit-dose parenteral preparations are packaged in an ampoule, a vial or a syringe with a needle. All preparations for parenteral administration must be sterile, as is known and practiced in the art.

Illustratively, intravenous or intraarterial infusion of a sterile aqueous solution containing an active compound is an effective mode of administration. Another embodiment is a sterile aqueous or oily solution or suspension containing an active material injected as necessary to produce the desired pharmacological effect.

Injectables are designed for local and systemic administration. Typically a therapeutically effective dosage is formulated to contain a concentration of at least about 0.1% w/w up to about 90% w/w or more, preferably more than 1% w/w of the active compound to the treated tissue(s). The active ingredient may be administered at once, or may be divided into a number of smaller doses,to be administered at intervals of time. It is understood that the precise dosage and duration of treatment is a function of the tissue being treated and may be determined empirically using known testing protocols or by extrapolation from in vivo or in vitro test data. It is to be noted that concentrations and dosage values may also vary with the age of the individual treated. It is to be further understood that for any particular subject, specific dosage regimens should be adjusted over time according to the individual need and the professional judgment of the person administering or supervising the administration of the formulations, and that the concentration ranges set forth herein are exemplary only and are not intended to limit the scope or practice of the claimed formulations.

The compound may be suspended in micronized or other suitable form or may be derivatized to produce a more soluble active product or to produce a prodrug. The form of the resulting mixture depends upon a number of factors, including the intended mode of administration and the solubility of the compound in the selected carrier or vehicle. The effective concentration is sufficient for ameliorating the symptoms of the condition and may be empirically determined.

3. Lyophilized Powders

Of interest herein are also lyophilized powders, which can be reconstituted for administration as solutions, emulsions and other mixtures. They may also be reconsitituted and formulated as solids or gels.

The sterile, lyophilized powder is prepared by dissolving a compound of formula I in a suitable solvent. The solvent may contain an excipient which improves the stability or other pharmacological component of the powder or reconstituted solution, prepared from the powder. Excipients that may be used include, but are not limited to, dextrose, sorbital, fructose, corn syrup, xylitol, glycerin, glucose, sucrose or other suitable agent. The solvent may also contain a buffer, such as citrate, sodium or potassium phosphate or other such buffer known to those of skill in the art at, typically, about neutral pH. Subsequent sterile filtration of the solution followed by lyophilization under standard conditions known to those of skill in the art provides the desired formulation. Generally, the resulting solution will be apportioned into vials for lyophilization. Each vial will contain a single dosage (10–1000 mg, preferably 100–500 mg) or multiple dosages of the compound. The lyophilized powder can be stored under appropriate conditions, such as at about 4° C. to room temperature.

Reconstitution of this lyophilized powder with water for injection provides a formulation for use in parenteral administration. For reconstitution, about 1–50 mg, preferably 5–35 mg, more preferably about 9–30 mg of lyophilized powder, is added per mL of sterile water or other suitable carrier. The precise amount depends upon the selected compound. Such amount can be empirically determined.

4. Topical Administration

Topical mixtures are prepared as described for the local and systemic administration. The resulting mixture may be a solution, suspension, emulsions or the like and are formulated as creams, gels, ointments, emulsions, solutions, elixirs, lotions, suspensions, tinctures, pastes, foams, aerosols, irrigations, sprays, suppositories, bandages, dermal patches or any other formulations suitable for topical administration.

The compounds or pharmaceutically acceptable derivatives thereof may be formulated as aerosols for topical application, such as by inhalation (see, e.g., U.S. Pat. Nos. 4,044,126, 4,414,209, and 4,364,923, which describe aerosols for delivery of a steroid useful for treatment inflammatory diseases, particularly asthma). These formulations for administration to the respiratory tract can be in the form of an aerosol or solution for a nebulizer, or as a microfine powder for insufflation, alone or in combination with an inert carrier such as lactose. In such a case, the particles of the formulation will typically have diameters of less than 50 microns, preferably less than 10 microns.

The compounds may be formulated for local or topical application, such as for topical application to the skin and mucous membranes, such as in the eye, in the form of gels, creams, and lotions and for application to the eye or for intracisternal or intraspinal application. Topical administration is contemplated for transdermal delivery and also for administration to the eyes or mucosa, or for inhalation therapies. Nasal solutions of the active compound alone or in combination with other pharmaceutically acceptable excipients can also be administered.

These solutions, particularly those intended for ophthalmic use, may be formulated as 0.01%–10% isotonic solutions, pH about 5–7, with appropriate salts.

5. Compositions for Other Routes of Administration

Other routes of administration, such as topical application, transdermal patches, and rectal administration are also contemplated herein.

For example, pharmaceutical dosage forms for rectal administration are rectal suppositories, capsules and tablets for systemic effect. Rectal suppositories are used herein mean solid bodies for insertion into the rectum which melt or soften at body temperature releasing one or more pharmacologically or therapeutically active ingredients. Pharmaceutically acceptable substances utilized in rectal suppositories are bases or vehicles and agents to raise the melting point. Examples of bases include cocoa butter (theobroma oil), glycerin-gelatin, carbowax (polyoxyethylene glycol) and appropriate mixtures of mono-, di- and triglycerides of fatty acids. Combinations of the various bases may be used. Agents to raise the melting point of suppositories include spermaceti and wax. Rectal suppositories may be prepared either by the compressed method or by molding. The typical weight of a rectal suppository is about 2 to 3 gm.

Tablets and capsules for rectal administration are manufactured using the same pharmaceutically acceptable substance and by the same methods as for formulations for oral administration.

6. Articles of Manufacture

The compounds or pharmaceutically acceptable derivatives may be packaged as articles of manufacture containing packaging material, a compound or pharmaceutically acceptable derivative thereof provided herein, which is effective for antagonizing PAI, particularly PAI-1, or for treatment, prevention or amelioration of one or more symptoms of thrombotic disorders, including, but not limited to, myocardial infarction, deep vein thrombosis and disseminated intravascular coagulation, and cancer, including, but not limited to, tumors, metastatic solid tumors and breast cancer, and a label that indicates that the compound or pharmaceutically acceptable derivative thereof is used for antagonizing PAI, particularly PAI-1, or for treatment, prevention or amelioration of one or more symptoms of thrombotic disorders, including, but not limited to, myocardial infarction, deep vein thrombosis and disseminated intravascular coagulation, and cancer, including, but not limited to, tumors, metastatic solid tumors and breast cancer.

The articles of manufacture provided herein contain packaging materials. Packaging materials for use in packaging pharmaceutical products are well known to those of skill in the art. See, e, U.S. Pat. Nos. 5,323,907, 5,052,558 and 5,033,252. Examples of pharmaceutical packaging materials include, but are not limited to, blister packs, bottles, tubes, inhalers, pumps, bags, vials, containers, syringes, bottles, and any packaging material suitable for a selected formulation and intended mode of administration and treatment. A wide array of formulations of the compounds and compositions provided herein are contemplated as are a variety treatments for any disorder in which PAI, particularly PAI-1, is implicated as a mediator or contributor to the symptoms or cause.

E. Evaluation of the Activity of the Compounds

Standard physiological, pharmacological and biochemical procedures are available for testing the compounds to identify those that possess biological activities that interfere with, antagonize, inhibit, or otherwise modulate the activity of PAI, particularly PAI-1. For example, the properties of a potential inhibitor may be assessed as a function of its ability to antagonize PAI activity including the ability in vitro to antagonize the activity of PAI-1.

Assays that may be used to evaluate PAI-1 activity are well known to those of skill in the art. See, e.g, Madison et al. (1989) *Nature* 339:721–723; Madison et al. (1990) *Proc. Natl. Acad. Sci. USA* 87:3530–3533; Madison et al. (1993) *Science* 262:419–421; U.S. Pat. Nos. 5,750,530, 5,902,812, 5,891,877; Charlton et al. (1996) *Thrombosis and Haemostasis* 75(5):808–815; and Charlton et al. (1997) *Fibrinolysis and Proteolysis* 11 (1):51–56.

Using such assays, the relative abilities of the compounds provided herein to antagonize or otherwise modulate the activity of PAI, particularly PAI-1, have been and can be assessed. Those that possess the desired in vitro properties, such as specific antagonism of PAI-1, are selected. The selected compounds that exhibit desirable activities may be therapeutically useful in the methods described herein and are tested for such uses employing the above-described assays from which the in vivo effectiveness may be evaluated. Compounds that exhibit the in vitro activities that correlate with the in vivo effectiveness will then be formulated in suitable pharmaceutical compositions and used as therapeutics.

. Methods of Use of PAI Antagonists

1. Methods of Treating, Preventing or Ameliorating One or More Symptoms of Thrombotic Disorders PAI, particularly PAI-1, has been implicated in the development and progression of thrombotic disorders, including, but not limited to, myocardial infarction, reocclusion following thrombolytic therapy, deep vein thrombosis and disseminated intravascular coagulation. Methods using therapeutically effective concentrations one or more of the compounds of formula I, or pharmaceutically acceptable derivatives thereof, for treating, preventing or ameliorating one or more symptoms of thrombotic disorders are provided herein. In particular, methods for using the compounds to treat, prevent or ameliorate one or more symptoms of myocardial infarction, reocclusion following thrombolytic therapy, deep vein thrombosis and disseminated intravascular coagulation are provided herein.

Preferably, a medicament containing the compound is administered oral, although administration by other methods, such as, but not limited to, topical, perenteral, intravenously (IV) and local administration may be tolerated in some instances. Generally, the medicament containing the compound is injected into the circulatory system of a subject in order to deliver a dose to the targeted cells. Targeting may be effected by linking the compound to a targeting agent specific for the desired cells, such as, but not limited to, endothelial cells. See, e.g,. U.S. Pat. Nos. 5,456,663, 4,764, 359, 5,543,391, 5,820,879, 5,026,558. Dosages may be determined empirically, but will typically be in the range of about 0.01 mg to about 100 mg of the compound per kilogram of body weight as a daily dosage.

Methods of modulating the activity of PAI, particularly PAI-1, using the compounds and compositions provided herein are also provided. The compounds and compositions provided herein are active in assays that measure the activity of PAI, specifically PAI-1. Preferred are methods of inhibiting the activity of PAI, in particular PAI-1.

Methods of modulating the interaction of PAs, particularly tPA, with PAI, particularly PAI-1, by administering one or more of the compounds provided herein, or pharmaceutically acceptable derivatives thereof, are provided.

2. Methods of Treating, Preventing or Ameliorating One or More Symptoms of Cancer PAI, particularly PAI-1, has been implicated in the growth and metastasis of certain types of cancers, particularly solid tumors. Methods using therapeutically effective concentrations one or more of the compounds of formula I, or pharmaceutically acceptable derivatives thereof, for treating, preventing or ameliorating one or more symptoms of cancer are provided herein. In particular, methods for using the compounds to treat, prevent or ameliorate one or more symptoms of tumors, solid tumors, metastatic solid tumors and breast cancer are provided herein.

Preferably, a medicament containing the compound is administered orally, although administration by other methods, such as, but not limited to, topical, parenteral, intravenously (IV) and local administration may be tolerated in some instances. Generally, the medicament containing the compound is injected into the circulatory system of a subject in order to deliver a dose to the targeted cells. Targeting may be effected by linking the compound to a targeting agent specific for the desired cells, such as, but not limited to, tumor cells. See, e., U.S. Pat. Nos. 5,456,663, 4,764,359, 5,543,391, 5,820,879, 5,026,558. Dosages may be determined empirically, but will typically be in the range of about 0.01 mg to about 100 mg of the compound per kilogram of body weight as a daily dosage.

Methods of modulating the interaction of PAs, particularly uPA, with PAI, particularly PAI-1, by administering one or more of the compounds provided herein, or pharmaceutically acceptable derivatives thereof, are provided.

Methods of attenuating metastasis by administration of one or more of the compounds and compositions provided herein are also provided.

Methods of modulating angiogenesis, preferably inhibiting angiogenesis, by administration of one or more of the compounds and compositions provided herein are provided.

The following examples are included for illustrative purposes only and are not intended to limit the scope of the invention.

EXAMPLE 1

4-(3-Bromobenzyloxy)-3,5-diiodo-benzoic Acid 3-bromobenzyl Ester

A suspension of 3,5-diiodo-4-hydroxybenzoic acid (0.39 g, 1.0 mmol), 3-bromobenzyl bromide (0.62 g, 2.5 mmol), and cesium carbonate (0.98 g, 3.0 mmol) in 10 mL DMF was stirred for 15 hours at room temperature. The mixture was then poured into 1 M HCl (100 mL) and a white precipitate formed. The precipitate was isolated by vacuum filtration and was recrystallized from hot isopropanol/chloroform, yielding the title compound as bright white crystals (610 mg, 84%); $^1H$ NMR ($CDCl_3$) δ 8.48 (s, 2H), 7.80 (br. s, 1H), 7.58–7.49 (m, 4H), 7.38–7.28 (m, 3H), 5.31 (s, 2H), 5.01 (s, 2H).

EXAMPLE 2

3,5-Diiodo-4-(3-bromobenzyloxy)benzoic Acid

A 1.2 M solution of LiOH (0.5 mL, 0.6 mmol) was added to a solution of 4-(3-bromobenzyloxy)-3,5-diiodobenzoic acid 3-bromobenzyl ester (Example 1)(363 mg, 0.5 mmol) in 4 mL THF. The biphasic solution was stirred for 17 hours, after which time the reaction mixture was poured into 1 M HCl (15 mL). The resulting white precipitate was isolated by filtration, rinsed with water, and dried in vacuo, yielding the title compound as a white powder (270 mg, 97%); $^1H$ NMR ($CDCl_3$) δ 8.48 (s, 2H), 7.80 (br. s, 1H), 7.58–7.49 (m, 4H), 7.38–7.28 (m, 3H), 5.31 (s, 2H), 5.01 (s, 2H).

EXAMPLE 3

3-(3,5-Diiodo-4-(3-Iodobenzyloxy)phenyl-propionic Acid 3-Iodobenzyl Ester

A suspension of 3,5-diiodo-4-hydroxyphenypropionic acid (209 mg, 0.5 mmol), 3-iodobenzyl bromide (371 mg, 1.25 mmol), and cesium carbonate (490 mg, 1.5 mmol) in 5 mL DMF was stirred for 15 h at room temperature. After that time, 1 M HCl (15 mL) was added and an oil formed. The oil was extracted with ether and methanol was added. Crystals formed in the solution upon cooling, yielding the title compound as white crystals (390 mg, 92%); $^1H$ NMR ($CDCl_3$) δ 8.00 (S, 1H), 7.71–7.60 (m, 6H), 7.29–7.26 (m, 1H), 7.16 (appar. t, J=7.8 Hz, 1H), 7.11 (appar. t, J=7.8 Hz, 1H), 5.05 (s, 2H), 4.91 (s, 2H), 2.87 (t, J=7.6 Hz, 2H), 2.67 (t, J=7.6 Hz, 2H).

EXAMPLE 4

3-(3,5-Diiodo-4-(3-Iodobenzyloxy)phenyl)propionic Acid

A 1.2 M solution of LiOH (275 μL, 0.33 mmol) was added to a solution of 3-(3,5-diiodo-4-(3-iodobenzyloxy)phenyl) propionic acid 3-iodobenzyl ester (Example 3)(213 mg, 0.25 mmol) in 2 mL THF. The biphasic solution was stirred for 14 hours, then 6 mL 0.5 M HCl was added and an oil formed. Methanol (0.5 mL) was added and the oil formed a solid, which was removed by filtration, yielding the title compound as an off-white powder (150 mg, 95%); $^1H$ NMR (DMSO) δ 12.15 (s, 1H), 7.96 (s, 1H), 7.76–7.75 (m, 3H), 7.62 (d, J=7.6 Hz, 1H), 7.26 (t, J=7.6 Hz, 1H), 4.87 (s, 2H), 2.75 (t, J=7.2 Hz, 2H), 2.54 (t, J=7.4 Hz).

EXAMPLE 5

Other compounds provided herein were prepared by minor modification of the methods of Examples 1–4. Analytical data for these compounds is provided in the following table.

TABLE

| COMPOUND | $^1$H NMR(SOLVENT) | MASS SPECTRUM |
|---|---|---|
| 3,5-diiodo-4-(3-iodo-benzyloxy)-benzoic acid | DMSO: 8.33(s, 2H), 7.98(s, 1H), 7.77(d, J=8.0Hz, 1H), 7.64(d, J=7.6Hz, 1H), 7.28(appar. t, J=7.8Hz, 1H), 4.97(s, 2H) | 718.6 (M + TFA) |
| 3,5-diiodo-4-(4-iodo-benzyloxy)-benzoic acid | DMSO: 8.33(s, 2H), 7.83(d, J=8.4Hz, 2H), 7.42(d, J=8.0Hz, 2 H), 4.95(s, 2H) | 604.2 (M − H), 718.8 (M + TFA) |
| 3,5-diiodo-4-(2-bromo-benzyloxy)-benzoic acid | DMSO: 13.37(br. s, 1H), 8.34(s, 2 H), 7.85(d, J=7.6Hz, 1H), 7.69 (d, J=8.0Hz, 1H), 7.52(appar. t, J=7.6Hz, 1H), 7.35(appar. t, J=7.6Hz, 1H), 5.08(s, 2H) | 556.6 (M − H), 670.6 (M + TFA) |
| 3,5-diiodo-4-(3-bromo-benzyloxy)-benzoic acid | DMSO: 13.39(br. s, 1H). 8.33(s, 2 H), 7.81(s, 1H), 7.63–7.61(m, 2H), 7.44(appar. t, J=7.8Hz, 1H), 5.00(s, 2H) | 556.6 (M − H), 670.6 (M + TFA) |
| 3,5-diiodo-4-(4-bromo-benzyloxy)-benzoic acid | DMSO: 13.39(br. s, 1H), 8.33(s, 2 H), 7.67(d, J=7.6Hz, 2H), 7.57 (d, J=8.0Hz, 2H), 4.98(s, 2H) | 556.8 (M − H), 672.4 (M + TFA) |
| 3,5-diiodo-4-(2-methyl-benzyloxy)-benzoic acid | DMSO: 13.38(br. s, 1H), 8.34(s, 2 H), 7.69(d, J=6.8Hz, 1H), 7.30–7.24(m, 3H), 5.02(s, 2H), 2.45(s, 3H) | 492.8 (M − H), 606.6 (M + TFA) |
| 3,5-diiodo-4-(3-methyl-benzyloxy)-benzoic acid | DMSO: 13.37(br. s, 1H), 8.33(s, 2 H), 7.44–7.43(m, 2H), 7.34(appar. t, J=7.4Hz, 1H), 7.22(d, J=7.6 Hz, 1H), 4.95(s, 2H), 2.36(s, 3H) | 492.6 (M − H), 606.6 (M + TFA) |
| 3,5-diiodo-4-(4-methyl-benzyloxy)-benzoic acid | DMSO: 13.38(br. s, 1H), 8.33(s, 2 H), 7.52(d, J=7.6Hz, 2H), 7.26 (d, J=7.6Hz, 2H), 4.94(s, 2H), 2.35(s, 3H) | 492.6 (M −H) |
| 4-(4-tert-butyl-benzyloxy)-3,5-diiodo-benzoic acid | DMSO: 13.38(br. s, 1H), 8.33(s, 2 H), 7.56(d, J=8.0Hz, 2H), 7.47 (d, J=8.0Hz, 2H), 4.94(s, 2H), 1.31(s, 9H) | — |
| 3,5-diiodo-4-(naphthalen-2-ylmethoxy)-benzoic acid | DMSO: 13.37(br. s, 1H), 8.36(s, 2 H), 8.12(s, 1H), 8.03–7.96(m, 3H), 7.80(d, J=8.4Hz, 1H), 7.59–7.55 (m, 2H), 5.18(s, 2H) | 528.8 (M − H), 642.6 (M + TFA) |
| 4-(biphenyl-2-ylmethoxy)-3,5-diiodo-benzoic acid | DMSO: 13.35(br. s, 1H), 8.26(s, 2 H), 7.93(d, J=8Hz, 1H), 7.52–7.31(m, 8H), 4.99(s, 2H) | 554.6 (M − H), 668.6 (M + TFA) |
| 3,5-diiodo-4-(3-methoxy-benzyloxy)-benzoic acid | DMSO: 13.38(br. s, 1H), 8.33(s, 2 H), 7.37(appar. t, J=7.8Hz, 1H), 7.22(br. s, 1H), 7.17(d, J=7.6 Hz, 1H), 6.99–6.96(m, 1H), 4.96(s, 2H), 3.80(s, 3H) | 508.8 (M − H), 622.6 (M + TFA), 1018.6(2M + H) |
| 3,5-diiodo-4-(3-trifluoromethyl-benzyloxy)-benzoic acid | DMSO: 13.42(br. s, 1H), 8.34(s, 2 H), 7.95–7.92(m, 2H), 7.79(d, J=7.6Hz, 1H), 7.72(appar. t, J=7.6 Hz, 1H), 5.11(s, 2H) | 546.4 (M − H), 660.6 (M + TFA), 1094.6 (2M + H), 1208.6 (2M + TFA) |
| 3,5-diiodo-4-(3-trifluoromethoxy-benzyloxy)-benzoic acid | DMSO: 13.39(br. s, 1H), 8.33(s, 2 H), 7.64–7.59(m, 3H), 7.42–7.40 (m, 1H), 5.05(s, 2H) | — |
| 4-(3-fluoro-benzyloxy)-3,5-diiodo-benzoic acid | DMSO: 13.41(br. s, 1H), 8.33(s, 2 H), 7.54–7.43(m, 3H), 7.27–7.22 (m, 1H), 5.02(s, 2H) | 496.6 (M − H), 610.8 (M + TFA), 994.6 (2M + H) |
| 3,5-diiodo-4-pentafluorophenylmethoxy-benzoic acid | DMSO: 13.42(br. s, 1H), 8.31(s, 2 H), 5.20(s, 2H) | 568.8 (M − H), 682.6 (M + TFA), 1138.4 (2M + H) |
| 3,5-dibromo-4-(3-iodo-benzyloxy)-benzoic acid | DMSO: 13.53(br. s, 1H), 8.14(s, 1 H), 7.93(s, 1H), 7.77(d, J=8.0 Hz, 1H), 7.60(d, J=6.8Hz, 1H), 7.26(t, J=7.8Hz, 1H), 5.04(s, 2 H) | 510.6 (M − H), 624.6 (M + TFA) |
| 3,5-dichloro-4-(3-iodo-benzyloxy)-benzoic acid | DMSO: 13.58(br. s, 1H), 7.97(s, 1 H). 7.91(s, 1H), 7.76(d, J=7.6 Hz, 1H), 7.60(d, J=7.6Hz, 1H), 7.24(t, J=7.8Hz, 1H), 5.09(s, 2 H) | 420.6 (M − H), 471.0 (M + TFA) |

TABLE-continued

| COMPOUND | $^1H$ NMR(SOLVENT) | MASS SPECTRUM |
|---|---|---|
| 3-[3,5-diiodo-4-(4-iodo-benzyloxy)-phenyl]-propionic acid | DMSO: 12.16(s, 1H), 7.82(d, J=7.6Hz, 2H), 7.76(s, 2H), 7.40(d, J=8.0Hz, 2H), 4.86(s, 2H), 2.75 (t, J=7.4Hz, 2H), 2.54(t, J=7.4 Hz, 2H) | 746.8 (M + TFA) |
| 3-(4-benzyloxy-3,5-diiodo-phenyl)-propionic acid | DMSO: 12.15(s, 1H), 7.77(s, 2H), 7.62(d, J=8.0Hz, 2H), 7.47–7.39 (m, 3H), 4.90(s, 2H), 2.75(t, J=7.4Hz, 2H), 2.54(t, J=7.4Hz, 2 H) | 620.8 (M + TFA) |
| 3-[4-(3-bromo-benzyloxy)-3,5-diiodo-phenyl]-propionic acid | DMSO: 12.13(br. s, 1H), 7.79–7.76 (m, 3H), 7.61–7.59(m, 2H), 7.42 (appar. t, J=7.8Hz, 1H), 4.91(s, 2H), 2.75(t, J=7.4Hz, 2H), 2.54 (t, J=7.4Hz, 2H) | 700.8 (M + TFA) |
| 3-[4-(4-bromo-benzyloxy)-3,5-diiodo-phenyl]-propionic acid | DMSO: 12.14(br. s, 1H), 7.76(s, 2 H), 7.65(d, J=8.0Hz, 2H), 7.55 (d, J=8.0Hz, 2H), 4.88(s, 2H), 2.75(t, J=7.4Hz, 2H), 2.54(t, J=7.4Hz, 2H) | 700.8 (M + TFA) |

EXAMPLE 6

Assays for Plasminogen Activator Inhibitor Type-1 Antagonism

Compounds provided herein for use in the compositions and methods can be and have been tested for PAI antagonist activity in any assay known to those of skill in the art. See, e.g., Madison et al. (1989) *Nature* 339:721–723; Madison et al. (1990) *Proc. Natl. Acad. Sci. USA* 87:3530–3533; Madison et al. (1993) *Science* 262:419–421; Charlton et al. (1997) *Fibrinolysis & Proteolysis* 11 (1):51–56; Charlton et al. (1996) *Thrombosis and Haemostasis* 75(5):808–815; and U.S. Pat. Nos. 5,750,530, 5,891,877 and 5,902,812.

Reagents

PAI-1 antagonist assays were performed in a buffer containing Tris, 0.05 mol/L, pH 7.4, 100 mmol/L NaCl, 1 mmol/L EDTA, and 0.01% Tween 80. Human recombinant PAI-1 purified from *E coli.* and human recombinant tPA were diluted into this standard assay buffer at concentrations of approximately 500–600 ng/mL and 100 ng/mL, respectively. PAI-1 antagonists were dissolved first in DMSO at a concentration of approximately 5 mg/mL, and these solutions were then diluted into the standard reaction buffer to achieve a final compound concentration of 1 mg/mL. Native, purified human glu-plasminogen was purchased from Boehringer Mannheim and was supplied as a lyophilized powder, which was first reconstituted in sterile: water to a concentration of 55 μmol/L and then diluted to a concentration of 0.825 μmol/L in standard assay buffer. The chromogenic substrate Spectrozyme PL (H-D-Norleucyl-hexahydrotyrosyl-lysine-p-nitroanilide, American Diagnostica) was prepared as a stock solution with a concentration of 2.5 mmol/L in sterile water. Human fibrin monomer (DESAFIB) was purchased from American Diagnostica and was supplied as a lyophilized powder, which was reconstituted in standard assay buffer at a concentration of 100 μg/mL.

Chromogenic Assay

The chromogenic assay utilized the reagents described above. Fresh reagent solutions were prepared prior to each assay. Assays were performed in individual wells of standard 96 well mocrotiter assay plates. Standard assays were prepared as follows:

Assay #1

The following reagents were combined:

| | |
|---|---|
| Test compound | 5 μL |
| PAI-1 | 10 μL |
| tPA | 10 μL |

The plate was agitated or the individual 25 μL mixtures were pipetted up and down once or twice to assure proper mixing of reagents. The resulting mixture was incubated 15 minutes at room temperature (approximately 21° C.).

The following was added to each reaction:

| | |
|---|---|
| DESAFIB | 25 μL |
| Glu-plasminogen | 25 μL |
| Spectrozyme PL | 25 μL |

The microtiter assay plate was then placed into a Molecular Devices Thermomax or Spectromax Plate Reader, agitated to assure 5 thorough mixing of reagents, and incubated at 37° C. The $OD_{405}$ of each reaction mixture is measured every minute for 1 hour. Control reactions which lack PAI-1; PAI-1 and test compound; t-PA; or t-PA, PAI-1 and test compound were performed in each assay.

Assay #2

Assay #2 was performed exactly as assay #1 except that a 10 minute preincubation of the test compound and PAI-1 was performed at room temperature prior to the addition of t-PA.

Assay #3

Assay #3 was performed exactly as assay #1 except that a wide range of concentrations of each test compound, depending upon the potency of the individual compound, was used in the assay.

Assay #4

Assay #4 was performed exactly as assay #2 except that a wide range of concentrations of each test compound, depending upon the potency of the individual compound, was used in the assay.

Results

Inhibition of PAI-1 by the compounds provided herein resulted in the production of plasmin from plasminogen. The generated plasmin cleaved the chromogenic substrate, Spectrozyme PL, producing pNA (para-nitroaniline). The pNA was detected spectrophotometrically at 405 nm.

The degree of inhibition at various concentrations and/or the $IC_{50}$ value for the compounds provided herein was determined by comparison with control reactions. The $IC_{50}$ for PAI antagonist activity for each of the compounds specifically disclosed herein has been measured. Almost all of the compounds have an $IC_{50}$ of less than 100 $\mu$M. Many of the compounds have an $IC_{50}$ less than about 50 $\mu$M, and some of the compounds have an $IC_{50}$ less than about 10 $\mu$M.

Since modifications will be apparent to those of skill in this art, it is intended that this invention be limited only by the scope of the appended claims.

What is claimed is:

1. A pharmaceutical composition, comprising a compound having the formula:

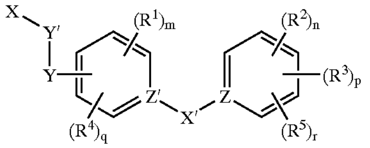

or a pharmaceutically acceptable derivative thereof, in a pharmaceutically acceptable carrier, wherein:

Z and Z' are each carbon;

X' is $(CH_2)_dO$ or $(CH_2)_dS$;

d is an integer from 1 to 6;

$R^1$ is halide or pseudohalide;

m is 2;

$R^2$, $R^3$, n and p are selected from (i) or (ii) as follows:

(i) $R^2$ is alkyl, aryl, alkoxy, haloalkyl, haloalkoxy, halide or pseudohalide; n is an integer from 1 to 5; $R^3$ is hydroxy or alkoxy; p is an integer from 0 to 3; or (ii) n and p are 1; and $R^2$ and $R^3$, together form, with the carbon to which each is attached, an aryl, aromatic ring, heteroaromatic ring, carbocyclic or heterocyclic ring, which is saturated or unsaturated, containing from about 3 to about 16 members;

$R^4$ and $R^5$ are each independently selected from —$SO_3^-$, —$NO_2$, alkyl, hydroxy, alkoxy, halide or pseudohalide;

q is an integer from 0 to 1;

r is an integer from 0 to 2;

X is H, $C_{1-17}$alkyl-L-, $C_{2-17}$alkenyl-L-, or $C_{2-17}$alkynyl-L-;

L is a direct link, amido, carboxy, carbonyl, carbamoyl, sulfonyl, carbamide, ureido, sulfonamide, hydrazinyl, hydrazide, semicarbazide, carbazate, thiocarbazate, isothiocarbazate or sulfonyl hydrazide;

Y' is selected from a direct link, alkylene, a heterocyclylene group, —COO—, —$S(O)_2O$—, —S(O)O—, —P(O)(OH)O—, —P(OH)O— and —B(OH)O—;

Y is a direcalky link, $C_{1-4}$alkyl(W)(carboxy), $C_{2-4}$alkenyl(W)(carboxy), $C_{2-4}$alkynyl(W)(carboxy), $C_{1-4}$alkyl(W)(sulfo), $C_{2-4}$alkenyl(W)(sulfo) or $C_{2-4}$alkynyl(W)(sulfo); where W is H, amino or A-D-E-G, where A is $C_{1-4}$alkylene, $C_{2-4}$alkenylene or $C_{2-4}$alkynylene; D is a direct link, amido, ureido, imino, azido, carbamoyl, thio or thionyl; E is a direct link, $C_{1-3}$alkylene, arylene or heteroarylene; and G is H, amino, nitro, cyano, hydrazinyl, thio or sulfonamido;

with the provisos that (i) if m, n or p are not 0, then q and r are 0; (ii) if q or r are not 0, then m, n and p are 0; (iii) if X is not H, then Y is a direct link; (iv) if Y is not a direct link, then Y' is a direct link; (v) if Y' is not a direct link, then Y is a direct link; (vi) if D is not a direct link, then G is H; (vii) if D is a single bond and G is not H, then E is a single bond; and (viii) if E is not a direct link or $C_{1-3}$alkylene, then G is H.

2. The pharmaceutical composition of claim 1, wherein the compound has formula I:

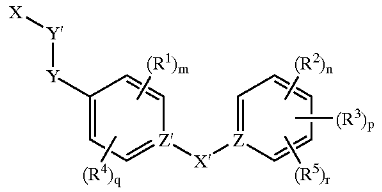

or a pharmaceutically acceptable derivative thereof, wherein:

Z and Z' are each carbon;

X' is $(CH_2)_dO$ or $(CH_2)_dS$;

d is an integer from 1 to 6;

$R^1$ is halide or pseudohalide;

m is 2;

$R^2$, $R^3$, n and p are selected from (i) or (ii) as follows:

(i) $R^2$ is alkyl, aryl, alkoxy, haloalkyl, haloalkoxy, halide or pseudohalide; n is an integer from 1 to 5; $R^3$ is hydroxy or alkoxy; p is an integer from 0 to 3; or (ii) n and p are 1; and $R^2$ and $R^3$, together form, with the carbon to which each is attached, an aryl, aromatic ring, heteroaromatic ring, carbocyclic or heterocyclic ring, which is saturated or unsaturated, containing from about 3 to about 16 members;

$R^4$ and $R^5$ are each independently selected from —$SO_3^-$, —$NO_2$, alkyl, hydroxy, alkoxy, halide or pseudohalide;

q is an integer from 0 to 1;

r is an integer from 0 to 2;

X is H, $C_{1-17}$alkyl-L-, $C_{2-17}$alkenyl-L-, or $C_{2-17}$alkynyl-L-;

L is a direct link, amido, carboxy, carbonyl, carbamoyl, sulfonyl, carbamide, ureido, sulfonamide, hydrazinyl, hydrazide, semicarbazide, carbazate, thiocarbazate, isothiocarbazate or sulfonyl hydrazide;

Y' is selected from a direct link, alkylene, a heterocyclylene group, —COO—, —$S(O)_2O$—, —S(O)O—, —P(O)(OH)O—, —P(OH)O— and —B(OH)O—;

Y is a direct link, $C_{1-4}$alkyl(W)(carboxy), $C_{2-4}$alkenyl(W)(carboxy), $C_{2-4}$alkynyl(W)(carboxy), $C_{1-4}$alkyl(W)(sulfo), $C_{2-4}$alkenyl(W)(sulfo) or $C_{2-4}$alkynyl(W)(sulfo); where W is H, amino or A-D-E-G, where A is $C_{14}$alkylene, $C_{2-4}$alkenylene or $C_{2-4}$alkynylene; D is a direct link, amido, ureido, imino, azido, carbamoyl, thio or thionyl; E is a direct link, $C_{1-3}$alkylene, arylene or heteroarylene; and G is H, amino, nitro, cyano, hydrazinyl, thio or sulfonamido;

with the provisos that (i) if m, n or p are not 0, then q and r are 0; (ii) if q or r are not 0, then m, n and p are 0; (iii) if X is not H, then Y is a direct link; (iv) if Y is not a direct link, then Y' is a direct link; (v) if Y' is not a direct link, then Y is a direct link; (vi) if D is not a direct link, then G is H; (vii) if D is a single bond and G is not H, then E is a single bond; and (viii) if E is not a direct link or $C_{1-3}$alkylene, then G is H.

3. The pharmaceutical composition of claim 2, wherein $R^1$ and $R^2$ are each halide.

4. The pharmaceutical composition of claim 2, wherein $R^1$ and $R^2$ are each iodo.

5. The pharmaceutical composition of claim 2, wherein X' is $(CH_2)_dO$.

6. The pharmaceutical composition of claim wherein the compound is of formula I with the proviso that X—Y'—Y is not hydrogen.

7. The pharmaceutical composition of claim 2, wherein:

Z and Z' are each carbon;

$R^1$ is iodo;

$R^2$ is iodo;

m is 2;

n is 1;

$R^3$ is OH;

p is an integer from 0 to 3;

$R^4$ and $R^5$ are each independently selected from $—SO_3^-$, $—NO_2$ and Me; q is an integer from 0 to 1; r is an integer from 0 to 2;

X is H, $C_{1-17}$alkyl-L-, $C_{2-17}$alkenyl-L-, or $C_{2-17}$alkynyl-L-; L is a direct link, amido, carboxy, carbonyl, carbamoyl, sulfonyl, carbamide, ureido, sulfonamide, hydrazinyl, hydrazide, semicarbazide, carbazate, thiocarbazate, isothiocarbazate or sulfonyl hydrazide;

Y' is a direct link, $C_8$alkylene, $—S(O)_2O—$,

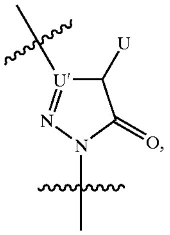

or

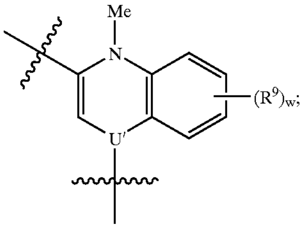

where U' is carbon and is attached to X; $R^9$ is $SO_3H$; w is an integer from 0 to 2; U is H or

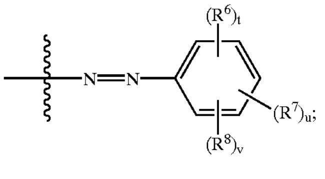

where $R^6$ is OH; t is an integer from 0 to 3; $R^7$ is $C_{1-3}$alkoxy; u is an integer from 0 to 3; $R^8$ is halo; v is an integer from 0 to 3;

Y is a direct link, $C_{1-4}$alkyl(W)(carboxy), $C_{2-4}$alkenyl(W)(carboxy), $C_{2-4}$alkynyl(W)(carboxy), $C_{14}$alkyl(W)(sulfo), $C_{2-4}$alkenyl(W)(sulfo) or $C_{2-4}$alkynyl(W)(sulfo); where W is H, amino or A-D-E-G, where A is $C_{1-4}$alkylene, $C_{2-4}$alkenylene or $C_{2-4}$alkynylene; D is a direct link, amido, ureido, imino, azido, carbamoyl, thio or thionyl; E is a direct link, $C_{1-3}$alkylene, arylene or heteroarylene; and G is H, amino, nitro, cyano, hydrazinyl, thio or sulfonamido;

with the provisos that (i) if m, n or p are not 0, then q and r are 0; (ii) if q or r are not 0, then m, n and p are 0; (iii) if X is not H, then Y is a direct link; (iv) if Y is not a direct link, then Y' is a direct link; (v) if Y' is not a direct link, then Y is a direct link; (vi) if D is not a direct link, then G is H; (vii) if D is a single bond and G is not H, then E is a single bond; and (viii) if E is not a direct link or $C_{1-3}$alkylene, then G is H.

8. The pharmaceutical composition of claim 7, wherein q and r are 0.

9. The pharmaceutical composition of claim 2 that is formulated for single dosage administration.

10. An article of manufacture, comprising packaging material, a compound of formula:

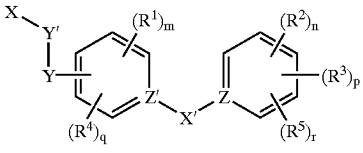

or a pharmaceutically acceptable derivative thereof, wherein:

Z and Z' are each carbon;

X' is $(CH_2)_dO$ or $(CH_2)_dS$;

d is an integer from 1 to 6;

$R^1$ is halide or pseudohalide;

m is 2;

$R^2$, $R^3$, n and p are selected from (i) or (ii) as follows:

(i) $R^2$ is alkyl, aryl, alkoxy, haloalkyl, haloalkoxy, halide or pseudohalide; n is an integer from 1 to 5; $R^3$ is hydroxy or alkoxy; p is an integer from 0 to 3; or (ii) n and p are 1; and $R^2$ and $R^3$, together form, with the carbon to which each is attached, an aryl, aromatic ring, heteroaromatic ring, carbocyclic or heterocyclic ring, which is saturated or unsaturated, containing from about 3 to about 16 members;

$R^4$ and $R^5$ are each independently selected from $—SO_3^-$, $—NO_2$, alkyl, hydroxy, alkoxy, halide or pseudohalide;

q is an integer from 0 to 1;

r is an integer from 0 to 2;

X is H, $C_{1-17}$alkyl-L-, $C_{2-17}$alkenyl-L-, or $C_{2-17}$alkynyl-L-;

L is a direct link, amido, carboxy, carbonyl, carbamoyl, sulfonyl, carbamide, ureido, sulfonamide, hydrazinyl, hydrazide, semicarbazide, carbazate, thiocarbazate, isothiocarbazate or sulfonyl hydrazide;

Y' is selected from a direct link, alkylene, a heterocyclylene group, —COO—, $—S(O)_2O—$, —S(O)O—, —P(O)(OH)O—, —P(OH)O— and —B(OH)O—;

Y is a direct link, $C_{1-4}$alkyl(W)(carboxy), $C_{2-4}$alkenyl(W)(carboxy), $C_{2-4}$alkynyl(W)(carboxy), $C_{1-4}$alkyl(W)(sulfo), $C_{2-4}$alkenyl(W)(sulfo) or $C_{2-4}$alkynyl(W)(sulfo); where W is H, amino or A-D-E-G, where A is $C_{1-4}$alkylene, $C_{2-4}$alkenylene or $C_{2-4}$alkynylene; D is a direct link, amido, ureido, imino, azido, carbamoyl, thio or thionyl; E is a direct link, $C_{1-3}$alkylene, arylene or heteroarylene; and G is H, amino, nitro, cyano, hydrazinyl, thio or sulfonamido;

with the provisos that (i) if m, n or p are not 0, then q and r are 0; (ii) if q or r are not 0, then m, n and p are 0; (iii) if X is not H, then Y is a direct link;

(iv) if Y is not a direct link, then Y' is a direct link; (v) if Y' is not a direct link, then Y is a direct link; (vi) if D is not a direct link, then G is H; (vii) if D is a single bond and G is not H, then E is a single bond; and (viii) if E is not a direct link or $C_{1-3}$alkylene, then G is H;

which is effective for antagonizing PAI or for treatment, prevention or amelioration of one or more symptoms of thrombotic disorders or cancer, and a label that indicates that the compound or pharmaceutically acceptable derivative thereof is used for antagonizing PAI, or for treatment, prevention or amelioration of one or more symptoms of thrombotic disorders or cancer.

11. A method of treating, preventing, or ameliorating one or more symptoms of cancer, comprising administering a compound of formula:

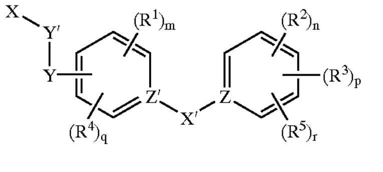

or a pharmaceutically acceptable derivative thereof, wherein:

Z and Z' are each carbon;

X' is $(CH_2)_dO$ or $(CH_2)_dS$;

d is an integer from 1 to 6;

$R^1$ is halide or pseudohalide;

m is 2;

$R^2$, $R^3$, n and p are selected from (i) or (ii) as follows:

(i) $R^2$ is alkyl, aryl, alkoxy, haloalkyl, haloalkoxy, halide or pseudohalide; n is an integer from 1 to 5; $R^3$ is hydroxy or alkoxy; p is an integer from 0 to 3; or (ii) n and p are 1; and $R^2$ and $R^3$, together form, with the carbon to which each is attached, an aryl, aromatic ring, heteroaromatic ring, carbocyclic or heterocyclic ring, which is saturated or unsaturated, containing from about 3 to about 16 members;

$R^4$ and $R^5$ are each independently selected from —$SO_3^-$, —$NO_2$, alkyl, hydroxy, alkoxy, halide or pseudohalide;

q is an integer from 0 to 1;

r is an integer from 0 to 2;

X is H, $C_{1-17}$alkyl-L-, $C_{2-17}$alkenyl-L-, or $C_{2-17}$alkynyl-L-;

L is a direct link, amido, carboxy, carbonyl, carbamoyl, sulfonyl, carbamide, ureido, sulfonamide, hydrazinyl, hydrazide, semicarbazide, carbazate, thiocarbazate, isothiocarbazate or sulfonyl hydrazide;

Y' is selected from a direct link, alkylene, a heterocyclylene group, —COO—, —$S(O)_2O$—, —S(O)O—, —P(O)(OH)O—, —P(OH)O— and —B(OH)O—;

Y is a direct link, $C_{1-4}$alkyl(W)(carboxy), $C_{2-4}$alkenyl(W)(carboxy), $C_{2-4}$alkynyl(W)(carboxy), $C_{1-4}$alkyl(W)(sulfo), $C_{2-4}$alkenyl(W)(sulfo) or $C_{2-4}$alkynyl(W)(sulfo); where W is H, amino or A-D-E-G, where A is $C_{1-4}$alkylene, $C_{2-4}$alkenylene or $C_{2-4}$alkynylene; D is a direct link, amido, ureido, imino, azido, carbamoyl, thio or thionyl; E is a direct link, $Cl_{13}$alkylene, arylene or heteroarylene; and G is H, amino, nitro, cyano, hydrazinyl, thio or sulfonamido;

with the provisos that (i) if m, n or p are not 0, then q and r are 0; (ii) if q or r are not 0, then m, n and p are 0; (iii) if X is not H, then Y is a direct link; (iv) if Y is not a direct link, then Y' is a direct link; (v) if Y' is not a direct link, then Y is a direct link; (vi) if D is not a direct link, then G is H; (vii) if D is a single bond and G is not H, then E is a single bond; and (viii) if E is not a direct link or $C_{1-3}$alkylene, then G is H.

12. The method of claim 11, wherein the cancer is selected from the group consisting of tumors, solid tumors, metastatic solid tumors and breast cancer.

13. A method of modulating the activity of a plasminogen activator inhibitor (PAI), comprising contacting the PAI with a compound of formula $Ar^1$—X'—$Ar^2$, or pharmaceutically acceptable derivatives thereof, wherein:

X' is O, S, $(CH_2)_dO$ or $(CH_2)_dS$ where d is an integer from 1 to 6;

$Ar^1$ and $Ar^2$ are each independently selected from monocyclic or fused bicyclic aryl and heteroaryl, and are substituted with at least one acidic group selected from a carboxylic acid, sulfonic acid, sulfinic acid, phosphonic acid, phosphinic acid or boronic acid group;

and may be further substituted with one or more substituents independently selected from halide, pseudohalide, nitro, hydroxy, alkoxy, aryl, heteroaryl, heterocyclyl, alkyl or cycloalkyl; wherein the aryl, heteroaryl, heterocyclyl and cycloalkyl substituents may be further substituted with $C_{1-20}$alkyl-L-, $C_{2-20}$alkenyl-L-, or $C_{2-20}$alkynyl-L-, where L is a direct link, amido, carboxy, carbonyl, carbamoyl, sulfonyl, carbamide, ureido, sulfonamide, hydrazinyl, hydrazide, semicarbazide, carbazate, thiocarbazate, isothiocarbazate or sulfonyl hydrazide.

14. The method of claim 13, wherein the compound has the formula:

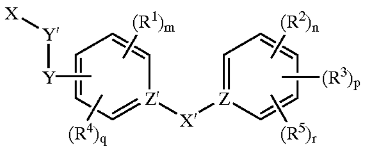

or a pharmaceutically acceptable derivative thereof, wherein:

Z and Z' are each carbon;

X' is O, S, $(CH_2)_dO$ or $(CH_2)_dS$;

d is an integer from 1 to 6;

$R^1$ is alkyl, aryl, alkoxy, haloalkyl, haloalkoxy, halide or pseudohalide;

m is an integer from 0 to 4;

$R^2$, $R^3$, n and p are selected from (i) or (ii) as follows:

(i) $R^2$ is alkyl, aryl, alkoxy, haloalkyl, haloalkoxy, halide or pseudohalide; n is an integer from 0 to 5; $R^3$ is hydroxy or alkoxy; p is an integer from 0 to 3; or (ii) n and p are 1; and $R^2$ and $R^3$, together form, with the carbon to which each is attached, an aryl, aromatic ring, heteroaromatic ring, carbocyclic or heterocyclic ring, which is saturated or unsaturated, containing from about 3 to about 16 members;

$R^4$ and $R^5$ are each independently selected from —$SO_3^-$, —$NO_2$, alkyl, hydroxy, alkoxy, halide or pseudohalide;

q is an integer from 0 to 1;

r is an integer from 0 to 2;

X is H, $C_{1-17}$alkyl-L-, $C_{2-17}$alkenyl-L-, or $C_{2-17}$alkynyl-L-;

L is a direct link, amido, carboxy, carbonyl, carbamoyl, sulfonyl, carbamide, ureido, sulfonamide, hydrazinyl, hydrazide, semicarbazide, carbazate, thiocarbazate, isothiocarbazate or sulfonyl hydrazide;

Y' is selected from a direct link, alkylene, a heterocyclylene group, —COO—, —$S(O)_2O$—, —S(O)O—, —P(O)(OH)O—, —P(OH)O— and —B(OH)O—;

Y is a direct link, $C_{1-4}$alkyl(W)(carboxy), $C_{2-4}$alkenyl(W)(carboxy), $C_{2-4}$alkynyl(W)(carboxy), $C_{1-4}$alkyl(W)(sulfo), $C_{2-4}$alkenyl(W)(sulfo) or $C_{2-4}$alkynyl(W)(sulfo); where W is H, amino or A-D-E-G, where A is $C_{1-4}$alkylene, $C_{2-4}$alkenylene or $C_{2-4}$alkynylene; D is a direct link, amido, ureido, imino, azido, carbamoyl, thio or thionyl; E is a direct link, $C_{1-3}$alkylene, arylene or heteroarylene; and G is H, amino, nitro, cyano, hydrazinyl, thio or sulfonamido;

with the provisos that (i) if m, n or p are not 0, then q and r are 0; (ii) if q or r are not 0, then m, n and p are 0; (iii) if X is not H, then Y is a direct link; (iv) if Y is not a direct link, then Y' is a direct link; (v) if Y' is not a direct link, then Y is a direct link; (vi) if D is not a direct link, then G is H; (vii) if D is a single bond and G is not H, then E is a single bond; and (viii) if E is not a direct link or $C_{1-3}$alkylene, then G is H.

15. A method of modulating the interaction of a plasminogen activator (PA) with a plasminogen activator inhibitor (PAI), comprising contacting the PAI with a compound of formula $Ar^1$—X'—$Ar^2$, or pharmaceutically acceptable derivatives thereof, wherein:

X' is O, S, $(CH_2)_dO$ or $(CH_2)_dS$ where d is an integer from 1 to 6;

$Ar^1$ and $Ar^2$ are each independently selected from monocyclic or fused bicyclic aryl and heteroaryl, and are substituted with at least one acidic group selected from a carboxylic acid, sulfonic acid, sulfinic acid, phosphonic acid, phosphinic acid or boronic acid group;

and may be further substituted with one or more substituents independently selected from halide, pseudohalide, nitro, hydroxy, alkoxy, aryl, heteroaryl, heterocyclyl, alkyl or cycloalkyl; wherein the aryl, heteroaryl, heterocyclyl and cycloalkyl substituents may be further substituted with $C_{1-20}$alkyl-L-, $C_{2-20}$alkenyl-L-, or $C_{2-20}$alkynyl-L-, where L is a direct link, amido, carboxy, carbonyl, carbamoyl, sulfonyl, carbamide, ureido, sulfonamide, hydrazinyl, hydrazide, semicarbazide, carbazate, thiocarbazate, isothiocarbazate or sulfonyl hydrazide;

wherein the contacting is effected simultaneously with, prior to, or subsequent to contacting the PA with the PAI.

16. The method of claim 13, wherein the compound has the formula:

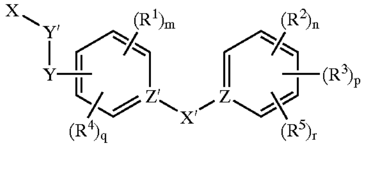

or a pharmaceutically acceptable derivative thereof, wherein:

Z and Z' are each carbon;

X' is O, S, $(CH_2)_dO$ or $(CH_2)_dS$;

d is an integer from 1 to 6;

$R^1$ is alkyl, aryl, alkoxy, haloalkyl, haloalkoxy, halide or pseudohalide;

m is an integer from 0 to 4;

$R^2$, $R^3$, n and p are selected from (i) or (ii) as follows:

(i) $R^2$ is alkyl, aryl, alkoxy, haloalkyl, haloalkoxy, halide or pseudohalide; n is an integer from 0 to 5; $R^3$ is hydroxy or alkoxy; p is an integer from 0 to 3; or (ii) n and p are 1; and $R^2$ and $R^3$, together form, with the carbon to which each is attached, an aryl, aromatic ring, heteroaromatic ring, carbocyclic or heterocyclic ring, which is saturated or unsaturated, containing from about 3 to about 16 members;

$R^4$ and $R^5$ are each independently selected from —$SO_3^-$, —$NO_2$, alkyl, hydroxy, alkoxy, halide or pseudohalide;

q is an integer from 0 to 1;

r is an integer from 0 to 2;

X is H, $C_{1-17}$alkyl-L-, $C_{2-17}$alkenyl-L-, or $C_{2-17}$alkynyl-L-;

L is a direct link, amido, carboxy, carbonyl, carbamoyl, sulfonyl, carbamide, ureido, sulfonamide, hydrazinyl, hydrazide, semicarbazide, carbazate, thiocarbazate, isothiocarbazate or sulfonyl hydrazide;

Y' is selected from a direct link, alkylene, a heterocyclylene group, —COO—, —$S(O)_2O$—, —S(O)O—, —P(O)(OH)O—, —P(OH)O— and —B(OH)O—;

Y is a direct link, $C_{1-4}$alkyl(W)(carboxy), $C_{2-4}$alkenyl(W)(carboxy), $C_{2-4}$alkynyl(W)(carboxy), $C_{1-4}$alkyl(W)(sulfo), $C_{2-4}$alkenyl(W)(sulfo) or $C_{2-4}$alkynyl(W)(sulfo); where W is H, amino or A-D-E-G, where A is $C_{1-4}$alkylene, $C_{2-4}$alkenylene or $C_{2-4}$alkynylene; D is a direct link, amido, ureido, imino, azido, carbamoyl, thio or thionyl; E is a direct link, $C_{1-3}$alkylene, arylene or heteroarylene; and G is H, amino, nitro, cyano, hydrazinyl, thio or sulfonamido;

with the provisos that (i) if m, n or p are not 0, then q and r are 0; (ii) if q or r are not 0, then m, n and p are 0; (iii) if X is not H, then Y is a direct link; (iv) if Y is not a direct link, then Y' is a direct link; (v) if Y' is not a direct link, then Y is a direct link; (vi) if D is not a direct link, then G is H; (vii) if D is a single bond and G is not H, then E is a single bond; and (viii) if E is not a direct link or $C_{1-3}$alkylene, then G is H.

17. A method of attenuating metastasis, comprising administrating to a patient suffering from a metastatic disorder a compound of formula $Ar^1$—X'—$Ar^2$, or pharmaceutically acceptable derivatives thereof, wherein:

X' is O, S, $(CH_2)_dO$ or $(CH_2)_dS$ where d is an integer from 1 to 6;

$Ar^1$ and $Ar^2$ are each independently selected from monocyclic or fused bicyclic aryl and heteroaryl, and are substituted with at least one acidic group selected from a carboxylic acid, sulfonic acid, sulfinic acid, phosphonic acid, phosphinic acid or boronic acid group;

and may be further substituted with one or more substituents independently selected from halide, pseudohalide, nitro, hydroxy, alkoxy, aryl, heteroaryl, heterocyclyl, alkyl or cycloalkyl; wherein the aryl, heteroaryl, heterocyclyl and cycloalkyl substituents may be further substituted with $C_{1-20}$alkyl-L-, $C_{2-20}$alkenyl-L-, or $C_{2-20}$alkynyl-L-, where L is a direct link, amido, carboxy, carbonyl, carbamoyl, sulfonyl, carbamide, ureido, sulfonamide, hydrazinyl, hydrazide, semicarbazide, carbazate, thiocarbazate, isothiocarbazate or sulfonyl hydrazide.

18. The method of claim 17, wherein the compound has the formula:

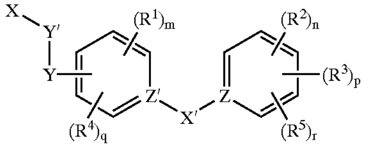

or a pharmaceutically acceptable derivative thereof, wherein:

Z and Z' are each carbon;

X' is O, S, $(CH_2)_dO$ or $(CH_2)_dS$;

d is an integer from 1 to 6;

$R^1$ is alkyl, aryl, alkoxy, haloalkyl, haloalkoxy, halide or pseudohalide;

m is an integer from 0 to 4;

$R^2$, $R^3$, n and p are selected from (i) or (ii) as follows:

(i) $R^2$ is alkyl, aryl, alkoxy, haloalkyl, haloalkoxy, halide or pseudohalide; n is an integer from 0 to 5; $R^3$ is hydroxy or alkoxy; p is an integer from 0 to 3; or (ii) n and p are 1; and $R^2$ and $R^3$, together form, with the carbon to which each is attached, an aryl, aromatic ring, heteroaromatic ring, carbocyclic or heterocyclic ring, which is saturated or unsaturated, containing from about 3 to about 16 members;

$R^4$ and $R^5$ are each independently selected from —$SO_3^-$, —$NO_2$, alkyl, hydroxy, alkoxy, halide or pseudohalide;

q is an integer from 0 to 1;

r is an integer from 0 to 2;

X is H, $C_{1-17}$alkyl-L-, $C_{2-17}$alkenyl-L-, or $C_{2-17}$alkynyl-L-;

L is a direct link, amido, carboxy, carbonyl, carbamoyl, sulfonyl, carbamide, ureido, sulfonamide, hydrazinyl, hydrazide, semicarbazide, carbazate, thiocarbazate, isothiocarbazate or sulfonyl hydrazide;

Y' is selected from a direct link, alkylene, a heterocyclylene group, —Coo—, —$S(O)_2O$—, —S(O)O—, —P(O)(OH)O—, —P(OH)O— and —B(OH)O—;

Y is a direct link, $C_{1-4}$alkyl(W)(carboxy), $C_{2-4}$alkenyl(W)(carboxy), $C_{2-4}$alkynyl(W)(carboxy), $C_{1-4}$alkyl(W)(sulfo), $C_{2-4}$alkenyl(W)(sulfo) or $C_{2-4}$alkynyl(W)(sulfo); where W is H, amino or A-D-E-G, where A is $C_{1-4}$alkylene, $C_{2-4}$alkenylene or $C_{2-4}$alkynylene; D is a direct link, amido, ureido, imino, azido, carbamoyl, thio or thionyl; E is a direct link, $C_{1-3}$alkylene, arylene or heteroarylene; and G is H, amino, nitro, cyano, hydrazinyl, thio or sulfonamido;

with the provisos that (i) if m, n or p are not 0, then q and r are 0; (ii) if q or r are not 0, then m, n and p are 0; (iii) if X is not H, then Y is a direct link; (iv) if Y is not a direct link, then Y' is a direct link; (v) if Y' is not a direct link, then Y is a direct link; (vi) if D is not a direct link, then G is H; (vii) if D is a single bond and G is not H, then E is a single bond; and (viii) if E is not a direct link or $C_{1-3}$alkylene, then G is H.

19. A method of treating, preventing or ameliorating one or more symptoms of a thrombotic disorder or haemostatic disorder, comprising administrating a compound of formula $Ar'$—$X'$—$Ar^2$, or pharmaceutically acceptable derivatives thereof, wherein:

X' is O, S, $(CH_2)_dO$ or $(CH_2)_dS$ where d is an integer from 1 to 6;

$Ar^1$ and $Ar^2$ are each independently selected from monocyclic or fused bicyclic aryl and heteroaryl, and are substituted with at least one acidic group selected from a carboxylic acid, sulfonic acid, sulfinic acid, phosphonic acid, phosphinic acid or boronic acid group;

and may be further substituted with one or more substituents independently selected from halide, pseudohalide, nitro, hydroxy, alkoxy, aryl, heteroaryl, heterocyclyl, alkyl or cycloalkyl; wherein the aryl, heteroaryl, heterocyclyl and cycloalkyl substituents may be further substituted with $C_{1-20}$alkyl-L-, $C_{2-20}$alkenyl-L-, or $C_{2-20}$alkynyl-L-, where L is a direct link, amido, carboxy, carbonyl, carbamoyl, sulfonyl, carbamide, ureido, sulfonamide, hydrazinyl, hydrazide, semicarbazide, carbazate, thiocarbazate, isothiocarbazate or sulfonyl hydrazide.

20. The method of claim 19, wherein the compound has the formula:

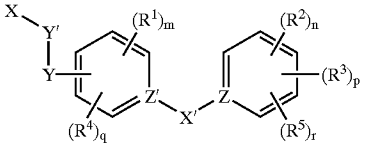

or a pharmaceutically acceptable derivative thereof, wherein:

Z and Z' are each carbon;

X' is O, S, $(CH_2)_dO$ or $(CH_2)_dS$;

d is an integer from 1 to 6;

$R^1$ is alkyl, aryl, alkoxy, haloalkyl, haloalkoxy, halide or pseudohalide;

m is an integer from 0 to 4;

$R^2$, $R^3$, n and p are selected from (i) or (ii) as follows:

(i) $R^2$ is alkyl, aryl, alkoxy, haloalkyl, haloalkoxy, halide or pseudohalide; n is an integer from 0 to 5; $R^3$ is hydroxy or alkoxy; p is an integer from 0 to 3; or (ii) n and p are 1; and $R^2$ and $R^3$, together form, with the carbon to which each is attached, an aryl, aromatic ring, heteroaromatic ring, carbocyclic or heterocyclic ring, which is saturated or unsaturated, containing from about 3 to about 16 members;

$R^4$ and $R^5$ are each independently selected from —$SO_3^-$, —$NO_2$, alkyl, hydroxy, alkoxy, halide or pseudohalide;

q is an integer from 0 to 1;

r is an integer from 0 to 2;

X is H, $C_{1-17}$alkyl-L-, $C_{2-17}$alkenyl-L-, or $C_{2-17}$alkynyl-L-;

L is a direct link, amido, carboxy, carbonyl, carbamoyl, sulfonyl, carbamide, ureido, sulfonamide, hydrazinyl, hydrazide, semicarbazide, carbazate, thiocarbazate, isothiocarbazate or sulfonyl hydrazide;

Y' is selected from a direct link, alkylene, a heterocyclylene group, —COO—, —$S(O)_2O$—, —S(O)O—, —P(O)(OH)O—, —P(OH)O— and —B(OH)O—;

Y is a direct link, $C_{1-4}$alkyl(W)(carboxy), $C_{2-4}$alkenyl(W)(carboxy), $C_{2-4}$alkynyl(W)(carboxy), $C_{1-4}$alkyl(W)(sulfo), $C_{2-4}$alkenyl(W)(sulfo) or $C_{2-4}$alkynyl(W)

(sulfo); where W is H, amino or A-D-E-G, where A is $C_{1-4}$alkylene, $C_{2-4}$alkenylene or $C_{2-4}$alkynylene; D is a direct link, amido, ureido, imino, azido, carbamoyl, thio or thionyl; E is a direct link, $C_{1-3}$alkylene, arylene or heteroarylene; and G is H, amino, nitro, cyano, hydrazinyl, thio or sulfonamido;

with the provisos that (i) if m, n or p are not 0, then q and r are 0; (ii) if q or r are not 0, then m, n and p are 0; (iii) if X is not H, then Y is a direct link; (iv) if Y is not a direct link, then Y' is a direct link; (v) if Y' is not a direct link, then Y is a direct link; (vi) if D is not a direct link, then G is H; (vii) if D is a single bond and G is not H, then E is a single bond; and (viii) if E is not a direct link or $C_{1-3}$alkylene, then G is H.

21. The method of claim 19, wherein the thrombotic disorder or haemostatic disorder is selected from myocardial infarction, reocclusion following thrombolytic therapy, deep vein thrombosis, or disseminated intravascular coagulation.

22. The method of claim 19, further comprising administration of tissue plasminogen activator (tPA), wherein the tPA is administered prior to, concurrently with, or subsequent to administration of the compound.

23. A method of antagonizing a plasminogen activator inhibitor PAI), comprising contacting the PAI with a compound of formula $Ar^1$—X'—$r^2$, or pharmaceutically acceptable derivatives thereof, wherein:

X' is O, S, $(CH_2)_dO$ or $(CH_2)_dS$ where d is an integer from 1 to 6;

$Ar^1$ and $Ar^2$ are each independently selected from monocyclic or fused bicyclic aryl and heteroaryl, and are substituted with at least one acidic group selected from a carboxylic acid, sulfonic acid, sulfinic acid, phosphonic acid, phosphinic acid or boronic acid group;

and may be further substituted with one or more substituents independently selected from halide, pseudohalide, nitro, hydroxy, alkoxy, aryl, heteroaryl, heterocyclyl, alkyl or cycloalkyl; wherein the aryl, heteroaryl, heterocyclyl and cycloalkyl substituents may be further substituted with $C_{1-20}$alkyl-L-, $C_{2-20}$alkenyl-L-, or $C_{2-20}$alkynyl-L-, where L is a direct link, amido, carboxy, carbonyl, carbamoyl, sulfonyl, carbamide, ureido, sulfonamide, hydrazinyl, hydrazide, semicarbazide, carbazate, thiocarbazate, isothiocarbazate or sulfonyl hydrazide.

24. The method of claim 23, wherein the compound has the formula:

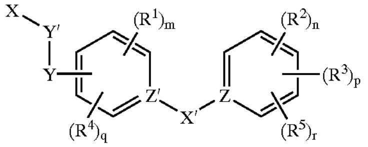

or a pharmaceutically acceptable derivative thereof, wherein:

Z and Z' are each carbon;

X' is O, S, $(CH_2)_dO$ or $(CH_2)_dS$;

d is an integer from 1 to 6;

$R^1$ is alkyl, aryl, alkoxy, haloalkyl, haloalkoxy, halide or pseudohalide;

m is an integer from 0 to 4;

$R^2$, $R^3$, n and p are selected from (i) or (ii) as follows:

(i) $R^2$ is alkyl, aryl, alkoxy, haloalkyl, haloalkoxy, halide or pseudohalide; n is an integer from Q to 5; $R^3$ is hydroxy or alkoxy; p is an integer from 0 to 3; or (ii) n and p are 1; and $R^2$ and $R^3$, together form, with the carbon to which each is attached, an aryl, aromatic ring, heteroaromatic ring, carbocyclic or heterocyclic ring, which is saturated or unsaturated, containing from about 3 to about 16 members;

$R^4$ and $R^5$ are each independently selected from —$SO_3^-$, —$NO_2$, alkyl, hydroxy, alkoxy, halide or pseudohalide;

q is an integer from 0 to 1;

r is an integer from 0 to 2;

X is H, $C_{1-17}$alkyl-L-, $C_{2-17}$alkenyl-L-, or $C_{2-17}$alkynyl-L-;

L is a direct link, amido, carboxy, carbonyl, carbamoyl, sulfonyl, carbamide, ureido, sulfonamide, hydrazinyl, hydrazide, semicarbazide, carbazate, thiocarbazate, isothiocarbazate or sulfonyl hydrazide;

Y' is selected from a direct link, alkylene, a heterocyclylene group, —COO—, —$S(O)_2O$—, —S(O)O—, —P(O)(OH)O—, —P(OH)O— and —B(OH)O—;

Y is a direct link, $C_{1-4}$alkyl(W)(carboxy), $C_{2-4}$alkenyl(W)(carboxy), $C_{2-4}$alkynyl(W)(carboxy), $C_{1-14}$alkyl(W)(sulfo), $C_{2-4}$alkenyl(W)(sulfo) or $C_{2-4}$alkynyl(W)(sulfo); where W is H, amino or A-D-E-G, where A is $C_{1-4}$alkylene, $C_{2-4}$alkenylene or $C_{2-4}$alkynylene; D is a direct link, amido, ureido, imino, azido, carbamoyl, thio or thionyl; E is a direct link, $C_{1-3}$alkylene, arylene or heteroarylene; and G is H, amino, nitro, cyano, hydrazinyl, thio or sulfonamido;

with the provisos that (i) if m, n or p are not 0, then q and r are 0; (ii) if q or r are not 0, then m, n and p are 0; (iii) if X is not H, then Y is a direct link; (iv) if Y is not a direct link, then Y' is a direct link; (v) if Y' is not a direct link, then Y is a direct link; (vi) if D is not a direct link, then G is H; (vii) if D is a single bond and G is not H, then E is a single bond; and (viii) if E is not a direct link or $C_{1-3}$alkylene, then G is H.

25. A method of modulating angiogenesis, comprising administering a compound of formula Ar'—X'—$Ar^2$, or pharmaceutically acceptable derivatives thereof, wherein:

X' is O, S, $(CH_2)_dO$ or $(CH_2)_dS$ where d is an integer from 1 to 6;

$Ar^1$ and $Ar^2$ are each independently selected from monocyclic or fused bicyclic aryl and heteroaryl, and are substituted with at least one acidic group selected from a carboxylic acid, sulfonic acid, sulfinic acid, phosphonic acid, phosphinic acid or boronic acid group;

and may be further substituted with one or more substituents independently selected from halide, pseudohalide, nitro, hydroxy, alkoxy, aryl, heteroaryl, heterocyclyl, alkyl or cycloalkyl; wherein the aryl, heteroaryl, heterocyclyl and cycloalkyl substituents may be further substituted with $C_{1-20}$alkyl-L-, $C_{2-20}$alkenyl-L-, or $C_{2-20}$alkynyl-L-, where L is a direct link, amido, carboxy, carbonyl, carbamoyl, sulfonyl, carbamide, ureido, sulfonamide, hydrazinyl, hydrazide, semicarbazide, carbazate, thiocarbazate, isothiocarbazate or sulfonyl hydrazide.

26. The method of claim 25, wherein the compound has the formula:

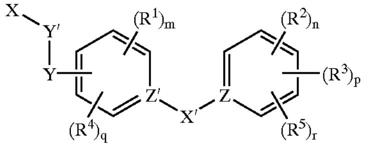

or a pharmaceutically acceptable derivative thereof, wherein:

Z and Z' are each carbon;

X' is O, S, $(CH_2)_dO$ or $(CH_2)_dS$;

d is an integer from 1 to 6;

$R^1$ is alkyl, aryl, alkoxy, haloalkyl, haloalkoxy, halide or pseudohalide;

m is an integer from 0 to 4;

$R^2$, $R^3$, n and p are selected from (i) or (ii) as follows:

(i) $R^2$ is alkyl, aryl, alkoxy, haloalkyl, haloalkoxy, halide or pseudohalide; n is an integer from 0 to 5; $R^3$ is hydroxy or alkoxy; p is an integer from 0 to 3; or (ii) n and p are 1; and $R^2$ and $R^3$, together form, with the carbon to which each is attached, an aryl, aromatic ring, heteroaromatic ring, carbocyclic or heterocyclic ring, which is saturated or unsaturated, containing from about 3 to about 16 members;

$R^4$ and $R^5$ are each independently selected from —$SO_3^-$, —$NO_2$, alkyl, hydroxy, alkoxy, halide or pseudohalide;

q is an integer from 0 to 1;

r is an integer from 0 to 2;

X is H, $C_{1-17}$alkyl-L-, $C_{2-17}$alkenyl-L-, or $C_{2-17}$alkynyl-L-;

L is a direct link, amido, carboxy, carbonyl, carbamoyl, sulfonyl, carbamide, ureido, sulfonamide, hydrazinyl, hydrazide, semicarbazide, carbazate, thiocarbazate, isothiocarbazate or sulfonyl hydrazide;

Y' is selected from a direct link, alkylene, a heterocyclylene group, —COO—, —$S(O)_2O$—, —S(O)O—, —P(O)(OH)O—, —P(OH)O— and —B(OH)O—;

Y is a direct link, $C_{1-14}$alkyl(W)(carboxy), $C_{2-4}$alkenyl(W)(carboxy), $C_{2-4}$alkynyl(W)(carboxy), $C_{1-4}$alkyl(W)(sulfo), $C_{2-4}$alkenyl(W)(sulfo) or $C_{2-4}$alkynyl(W)(sulfo); where W is H, amino or A-D-E-G, where A is $C_{1-4}$alkylene, $C_{2-4}$alkenylene or $C_{2-4}$alkynylene; D is a direct link, amido, ureido, imino, azido, carbamoyl, thio or thionyl; E is a direct link, $C_{1-3}$alkylene, arylene or heteroarylene; and G is H, amino, nitro, cyano, hydrazinyl, thio or sulfonamido;

with the provisos that (i) if m, n or p are not 0, then q and r are 0; (ii) if q or r are not 0, then m, n and p are 0; (iii) if X is not H, then Y is a direct link; (iv) if Y is not a direct link, then Y' is a direct link; (v) if Y' is not a direct link, then Y is a direct link; (vi) if D is not a direct link, then G is H; (vii) if D is a single bond and G is not H, then E is a single bond; and (viii) if E is not a direct link or $C_{1-3}$alkylene, then G is H.

27. A compound that has the formula:

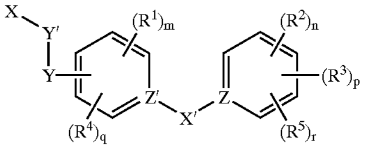

and pharmaceutically acceptable derivatives thereof, wherein:

X' is $(CH_2)_dO$ or $(CH_2)_dS$;

d is an integer from 1 to 6;

Z and Z' are each carbon;

$R^1$ is Br or I;

m is 2;

$R^2$, $R^3$, n and p are selected from (i) or (ii) as follows:

(i) $R^2$ is halide, pseudohalide, alkyl, aryl, heteroaryl, cycloalkyl, alkoxy, aryloxy, heteroaryloxy, cycloalkoxy, haloalkyl or haloalkoxy; n is an integer from 1 to 5; $R^3$ is OH or alkoxy; p is an integer from 0 to 3; or (ii) n and p are 1; and $R^2$ and $R^3$ together form, with the carbon to which each is attached, an aryl, aromatic ring, heteroaromatic ring, carbocyclic or heterocyclic ring, which is saturated or unsaturated, containing from about 3 to about 16 members;

$R^4$ and $R^5$ are each independently selected from —$SO_3^-$, —$NO_2$, alkyl, hydroxy, alkoxy, halide or pseudohalide; q is an integer from 0 to 1; r is an integer from 0 to 2;

X is H, $C_{1-17}$alkyl-L-, $C_{2-17}$alkenyl-L-, or $C_{2-17}$alkynyl-L-; L is a direct link, amido, carboxy, carbonyl, carbamoyl, sulfonyl, carbamide, ureido, sulfonamide, hydrazinyl, hydrazide, semicarbazide, carbazate, thiocarbazate, isothiocarbazate or sulfonyl hydrazide;

Y' is selected from a direct link, alkylene, a heterocyclylene group, —COO—, —$S(O)_2O$—, —S(O)O—, —P(O)(OH)O—, —P(OH)O— and —B(OH)O—;

Y is a direct link, $C_{1-4}$alkyl(W)(carboxy), $C_{2-4}$alkenyl(W)(carboxy), $C_{2-4}$alkynyl(W)(carboxy), $C_{1-4}$alkyl(W)(sulfo), $C_{2-4}$alkenyl(W)(sulfo) or $C_{2-4}$alkynyl(W)(sulfo); where W is H, amino or A-D-E-G, where A is $C_{1-4}$alkylene, $C_{2-4}$alkenylene or $C_{2-4}$alkynylene; D is a direct link, amido, ureido, imino, azido, carbamoyl, thio or thionyl; E is a direct link, $C_{1-3}$alkylene, arylene or heteroarylene; and G is H, amino, nitro, cyano, hydrazinyl, thio or sulfonamido;

with the provisos that (i) if m, n or p are not 0, then q and r are 0; (ii) if q or r are not 0, then m, n and p are 0; (iii) if X is not H, then Y is a direct link; (iv) if Y is not a direct link, then Y' is a direct link; (v) if Y' is not a direct link, then Y is a direct link; (vi) if D is not a direct link, then G is H; (vii) if D is a single bond and G is not H, then E is a single bond; (viii) if E is not a direct link or $C_{1-3}$alkylene, then G is H.

28. The compound of claim 27, that has formula I:

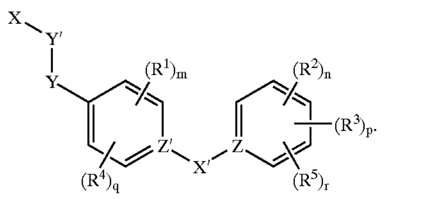

29. The compound of claim 28, wherein X' is $(CH_2)_dO$.

30. The compound of claim 28, wherein X' is $CH_2O$.

31. The compound of claim 28, wherein:

$R^2$, $R^3$, n and p are selected from (i) or (ii) as follows:

(i) $R^2$ is halide, pseudohalide, alkyl, aryl, heteroaryl, cycloalkyl, alkoxy, aryloxy, heteroaryloxy, cycloalkoxy, haloalkyl or haloalkoxy; n is an integer from 1 to 5; $R^3$ is OH or alkoxy; p is an integer from 0 to 3; or (ii) n and p are 1; and $R^2$ and $R^3$ together form —CH=CH—CH=CH—, —CH=N—CH=CH— or —N=CH—CH=CH—;

$R^4$ and $R^5$ are each independently selected from $—SO_3^-$, $—NO_2$ and Me; and Y' is a direct link, $C_8$alkylene, $—S(O)_2O—$,

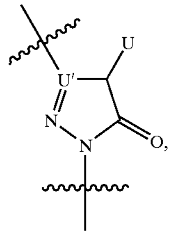

or

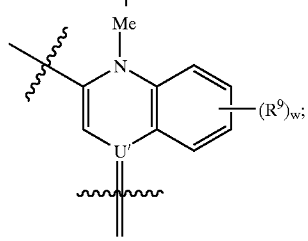

where U' is carbon and is attached to X; $R^9$ is $SO_3H$; w is an integer from 0 to 2; U is H or

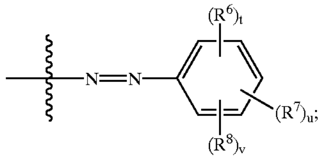

where $R^6$ is OH; t is an integer from 0 to 3; $R^7$ is $C_{1-3}$alkoxy; u is an integer from 0 to 3; $R^8$ is halo; and v is an integer from 0 to 3.

32. The compound of claim 28, wherein q and r are 0 and the compound has formula II:

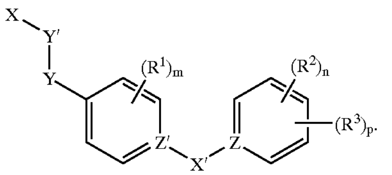

33. The compound of claim 28, wherein Y' is a direct link, q and r are 0, and the compound has formula III:

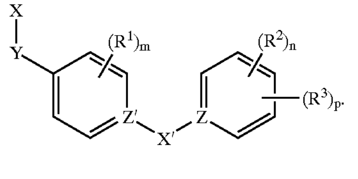

34. The compound of claim 33, wherein X' is $(CH_2)_dO$, where d is an integer from 1 to 6.

35. The compound of claim 33, wherein X' is $CH_2O$.

36. The compound of claim 33, wherein X—Y is $(CH_2)_aCOOH$ or $(CH_2)_cSO_3H$, where a is an integer from 0 to 6 and c is an integer from 0 to 4.

37. The compound of claim 33, wherein X—Y is $(CH_2)_8COOH$, where a is an integer from 0 to 6.

38. The compound of claim 33, wherein a is 0 or 2.

39. The compound of claim 37 that has formula IV:

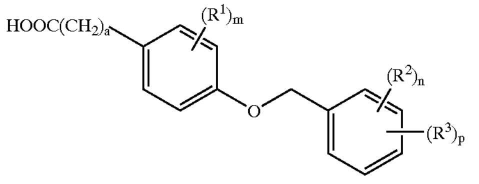

wherein:

$R^1$ is Br or I;

m is 2;

a is an integer from 0 to 6; and $R^2$, $R^3$, n and p are selected as in (i) or (ii) as follows:

(i) $R^2$ is halide, pseudohalide, alkyl, aryl, heteroaryl, cycloalkyl, alkoxy, aryloxy, heteroaryloxy, cycloalkoxy, haloalkyl or haloalkoxy; n is an integer from 1 to 5; and p is 0; or (ii) n and p are 1, and $R^2$ and $R^3$ together form, with the carbon to which each is attached, an aryl, aromatic ring, heteroaromatic ring, carbocyclic or heterocyclic ring, which is saturated or unsaturated, containing from about 3 to about 16 members.

40. The compound of claim 39, wherein $R^1$ is Br or I; and $R^2$, $R^3$, n and p are selected as in (i) or (ii) as follows:

(i) $R^2$ is halide, pseudohalide, alkyl, aryl, heteroaryl, cycloalkyl, alkoxy, aryloxy, heteroaryloxy, cycloalkoxy, haloalkyl or haloalkoxy; n is an integer from 1 to 5; and p is 0; or (ii) n and p are 1, and $R^2$ and $R^3$ together form —CH=CH—CH=CH—, —CH=N—CH=CH— or —N=CH—CH=CH—.

41. The compound of claim 39, wherein $R^1$ is Br or I; m is 2; and $R^2$, $R^3$, n and p are selected from (i) or (ii) as follows:

(i) $R^2$ is selected from 1, Br, $CH_3$, $C(CH_3)_3$, Ph, $OCH_3$, $CF_3$, $OCF_3$ or F; n is 1, or is 1 or 5 when $R^2$ is F; p is 0; or (ii) n and p are 1; and $R^2$ and $R^3$ together form —CH=CH—CH=CH—.

42. The compound of claim 41, wherein $R^1$ is I.

43. The compound of claim 41, wherein a is 0 or 2.

44. The compound of claim 28, selected from the group consisting of 3,5-diiodo-4-(3-bromobenzyloxy)benzoic acid, 3-(3,5-diiodo-4-(3-iodobenzyloxy)phenyl)propionic acid, 3,5-diiodo-4-(3-iodobenzyloxy)-benzoic acid; 3,5-diiodo-4-(4-iodobenzyloxy)benzoic acid; 3,5-diiodo-4-(2-bromobenzyloxy)benzoic acid; 3,5-diiodo-4-(4-bromobenzyloxy)benzoic acid; 3,5-diiodo-4-(2-methylbenzyloxy)benzoic acid; 3,5-diiodo-4-(3-methylbenzyloxy)benzoic acid; 3,5-diiodo-4-(4-methylbenzyloxy)benzoic acid; 3,5-diiodo-4-(4-tert-butylbenzyloxy)benzoic acid; 3,5-diiodo-4-(naphth-2-ylmethoxy)benzoic acid; 3,5-diiodo-4-(biphen-2-ylmethoxy)-benzoic acid; 3,5-diiodo-4-(3-methoxybenzyloxy)benzoic acid; 3,5-diiodo-4-(3-trifluoromethylbenzyloxy)benzoic acid; 3,5-diiodo-4-(3-trifluoromethoxybenzyloxy)benzoic acid; 3,5-diiodo-4-(3-fluorobenzyloxy)benzoic acid; 3,5-diiodo-4-(2,3,4,5,6-pentafluorophenylmethoxy)benzoic acid; 3-(3,5-diiodo-4-(4-iodobenzyloxy)phenyl)propionic acid; 3-(3,5-diiodo-4-(benzyloxy)phenyl)propionic acid; 3-(3,5-diiodo-4-(3-bromobenzyloxy)-phenyl)propionic acid; 3,5-dibromo-4-(3-iodobenzyloxy)benzoic acid; 3,5-dichloro-4-(3-iodobenzyloxy)benzoic acid; and 3-(3,5-diiodo-4-(4-bromobenzyloxy)phenyl)propionic acid.

45. A pharmaceutical composition, comprising the compound of claim 27, or a pharmaceutically acceptable derivative thereof, in a pharmaceutically acceptable carrier.

46. The pharmaceutical composition of claim 45 that is formulated for single dosage administration.

47. An article of manufacture, comprising packaging material, a compound of claim 27, or a pharmaceutically acceptable derivative thereof, which is effective for antagonizing PAI or for treatment, prevention or amelioration of one or more symptoms of thrombotic disorders or cancer, and a label that indicates that the compound or pharmaceutically acceptable derivative thereof is used for antagonizing PAI, or for treatment, prevention or amelioration of one or more symptoms of thrombotic disorders or cancer.

48. A method for treating, preventing, or ameliorating one or more symptoms of cancer, comprising administering a compound of claim 27 or a pharmaceutically acceptable derivative thereof.

49. The method of claim 48, wherein the cancer is selected from the group consisting of tumors, solid tumors, metastatic solid tumors and breast cancer.

50. A method of modulating the activity of a plasminogen activator inhibitor (PAI), comprising contacting the PAI with a compound of claim 27, or pharmaceutically acceptable derivatives thereof.

51. A method of modulating the interaction of a plasminogen activator (PA) with a plasminogen activator inhibitor (PAI), comprising contacting the PAI with a compound of claim 27, or pharmaceutically acceptable derivatives thereof, wherein the contacting is effected simultaneously with, prior to, or subsequent to contacting the PA with the PAI.

52. A method of attenuating metastasis, comprising administrating to a patient suffering from a metastatic disorder a compound of claim 27, or a pharmaceutically acceptable derivative thereof.

53. A method of treating, preventing or ameliorating one or more symptoms of a thrombotic disorder or haemostatic disorder, comprising administrating a compound of claim 27, or pharmaceutically acceptable derivatives thereof.

54. The method of claim 53, wherein the thrombotic disorder or haemostatic disorder is selected from myocardial infarction, reocclusion following thrombolytic therapy, deep vein thrombosis, or disseminated intravascular coagulation.

55. The method of claim 53, further comprising administration of tissue plasminogen activator (tPA), wherein the tPA is administered prior to, concurrently with, or subsequent to administration of the compound.

56. A method of antagonizing a plasminogen activator inhibitor (PAI), comprising contacting the PAI with a compound of claim 27, or pharmaceutically acceptable derivatives thereof.

57. A method of modulating angiogenesis, comprising administering a compound of claim 27, or pharmaceutically acceptable derivatives thereof.

58. The compound of claim 28 that is 3,5-diiodo-4-(3-iodobenzyloxy)benzoic acid, or a pharmaceutically acceptable derivative thereof.

59. A pharmaceutical composition, comprising the compound of claim 58, or a pharmaceutically acceptable derivative thereof, in a pharmaceutically acceptable carrier.

60. The pharmaceutical composition of claim 59 that is formulated for single dosage administration.

61. An article of manufacture, comprising packaging material, the compound of claim 58, or a pharmaceutically acceptable derivative thereof, which is effective for antagonizing PAI or for treatment, prevention or amelioration of one or more symptoms of thrombotic disorders or cancer, and a label that indicates that the compound or pharmaceutically acceptable derivative thereof is used for antagonizing PAI, or for treatment, prevention or amelioration of one or more symptoms of thrombotic disorders or cancer.

62. A method for treating, preventing, or ameliorating one or more symptoms of cancer, comprising administering the compound of claim 58 or a pharmaceutically acceptable derivative thereof.

63. The method of claim 62, wherein the cancer is selected from the group consisting of tumors, solid tumors, metastatic solid tumors and breast cancer.

64. A method of modulating the activity of a plasminogen activator inhibitor (PAI), comprising contacting the PAI with the compound of claim 58, or pharmaceutically acceptable derivatives thereof.

65. A method of modulating the interaction of a plasminogen activator (PA) with a plasminogen activator inhibitor (PAI), comprising contacting the PAI with the compound of claim 58, or pharmaceutically acceptable derivatives thereof, wherein the contacting is effected simultaneously with, prior to, or subsequent to contacting the PA with the PAI.

66. A method of attenuating metastasis, comprising administrating to a patient suffering from a metastatic disorder the compound of claim 58, or a pharmaceutically acceptable derivative thereof.

67. A method of treating, preventing or ameliorating one or more symptoms of a thrombotic disorder or haemostatic disorder, comprising administrating the compound of claim 58, or pharmaceutically acceptable derivatives thereof.

68. The method of claim 67, wherein the thrombotic disorder or haemostatic disorder is selected from myocardial infarction, reocclusion following thrombolytic therapy, deep vein thrombosis, or disseminated intravascular coagulation.

69. The method of claim 67, further comprising administration of tissue plasminogen activator (tPA), wherein the tPA is administered prior to, concurrently with, or subsequent to administration of the compound.

70. A method of antagonizing a plasminogen activator inhibitor (PAI), comprising contacting the PAI with the compound of claim 58, or pharmaceutically acceptable derivatives thereof.

71. A method of modulating angiogenesis, comprising administering the compound of claim 58, or pharmaceutically acceptable derivatives thereof.

* * * * *

UNITED STATES PATENT AND TRADEMARK OFFICE

CERTIFICATE OF CORRECTION

PATENT NO. : 6,638,977 B1
DATED : October 28, 2003
INVENTOR(S) : Madison et al.

It is certified that error appears in the above-identified patent and that said Letters Patent is hereby corrected as shown below:

Column 43,
Line 20, replace claim 1, with the following:

1. A pharmaceutical composition, comprising a compound having the formula:

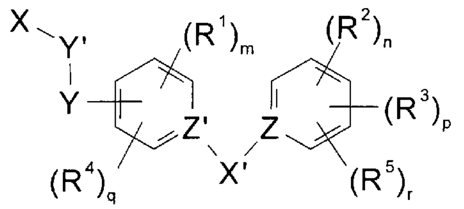

or a pharmaceutically acceptable derivative thereof, in a pharmaceutically acceptable carrier, wherein:

Z and Z' are each carbon;

X' is $(CH_2)_dO$ or $(CH_2)_dS$;

d is an integer from 1 to 6;

$R^1$ is halide or pseudohalide;

m is 2;

$R^2$, $R^3$, n and p are selected from (i) or (ii) as follows:

(i) $R^2$ is alkyl, aryl, alkoxy, haloalkyl, haloalkoxy, halide or pseudohalide; n is an integer from 1 to 5; $R^3$ is hydroxy or alkoxy; p is an integer from 0 to 3; or (ii) n and p are 1; and $R^2$ and $R^3$, together form, with the carbon to which each is attached, an aryl, aromatic ring, heteroaromatic ring, carbocyclic or heterocyclic ring, which is saturated or unsaturated, containing from about 3 to about 16 members;

$R^4$ and $R^5$ are each independently selected from $-SO_3^-$, $-NO_2$, alkyl, hydroxy, alkoxy, halide or pseudohalide;

q is an integer from 0 to 1;

r is an integer from 0 to 2;

X is H, $C_{1-17}$alkyl-L-, $C_{2-17}$alkenyl-L-, or $C_{2-17}$alkynyl-L-;

L is a direct link, amido, carboxy, carbonyl, carbamoyl, sulfonyl, carbamide, ureido, sulfonamide, hydrazinyl, hydrazide, semicarbazide, carbazate, thiocarbazate, isothiocarbazate or sulfonyl hydrazide;

Y' is selected from a direct link, alkylene, a heterocyclylene group, -COO-, -$S(O)_2O$-, -S(O)O-, -P(O)(OH)O-, -P(OH)O- and -B(OH)O-;

Y is a direct link, $C_{1-4}$alkyl(W)(carboxy), $C_{2-4}$alkenyl(W)(carboxy), $C_{2-4}$alkynyl(W)(carboxy), $C_{1-4}$alkyl(W)(sulfo), $C_{2-4}$alkenyl(W)(sulfo) or $C_{2-4}$alkynyl(W)(sulfo); where W is H, amino or A-D-E-G, where A is $C_{1-4}$alkylene, $C_{2-4}$alkenylene or $C_{2-4}$alkynylene; D is a direct link, amido, ureido, imino, azido, carbamoyl, thio or thionyl; E is a direct link, $C_{1-3}$alkylene, arylene or heteroarylene; and G is H, amino, nitro, cyano, hydrazinyl, thio or sulfonamido;

with the provisos that (i) if m, n or p are not 0, then q and r are 0; (ii) if q or r are not 0, then m, n and p are 0; (iii) if X is not H, then Y is a direct link; (iv) if Y is not a direct link, then Y' is a direct link; (v) if Y' is not a direct link, then Y is a direct link; (vi) if D is not a direct link, then G is H; (vii) if D is a single bond and G is not H, then E is a single bond; and (viii) if E is not a direct link or $C_{1-3}$alkylene, then G is H.

UNITED STATES PATENT AND TRADEMARK OFFICE
CERTIFICATE OF CORRECTION

PATENT NO. : 6,638,977 B1
DATED : October 28, 2003
INVENTOR(S) : Madison et al.

It is certified that error appears in the above-identified patent and that said Letters Patent is hereby corrected as shown below:

Column 44,
Line 12, replace claim 2, with the following:

2. The pharmaceutical composition of claim 1, wherein the compound has formula I:

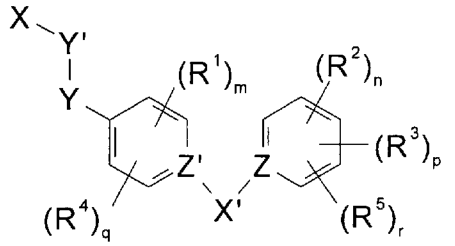

or a pharmaceutically acceptable derivative thereof, wherein:
Z and Z′ are each carbon;
X′ is $(CH_2)_dO$ or $(CH_2)_dS$;
d is an integer from 1 to 6;
$R^1$ is halide or pseudohalide;
m is 2;
$R^2$, $R^3$, n and p are selected from (i) or (ii) as follows:
(i) $R^2$ is alkyl, aryl, alkoxy, haloalkyl, haloalkoxy, halide or pseudohalide; n is an integer from 1 to 5; $R^3$ is hydroxy or alkoxy; p is an integer from 0 to 3; or
(ii) n and p are 1; and $R^2$ and $R^3$, together form, with the carbon to which each is attached, an aryl, aromatic ring, heteroaromatic ring, carbocyclic or heterocyclic ring, which is saturated or unsaturated, containing from about 3 to about 16 members;
$R^4$ and $R^5$ are each independently selected from $-SO_3^-$, $-NO_2$, alkyl, hydroxy, alkoxy, halide or pseudohalide;
q is an integer from 0 to 1;
r is an integer from 0 to 2;

X is H, $C_{1-17}$alkyl-L-, $C_{2-17}$alkenyl-L-, or $C_{2-17}$alkynyl-L-;
L is a direct link, amido, carboxy, carbonyl, carbamoyl, sulfonyl, carbamide, ureido, sulfonamide, hydrazinyl, hydrazide, semicarbazide, carbazate, thiocarbazate, isothiocarbazate or sulfonyl hydrazide;
Y′ is selected from a direct link, alkylene, a heterocyclylene group, -COO-, -$S(O)_2O$-, -S(O)O-, -P(O)(OH)O-, -P(OH)O- and -B(OH)O-;
Y is a direct link, $C_{1-4}$alkyl(W)(carboxy), $C_{2-4}$alkenyl(W)(carboxy), $C_{2-4}$alkynyl(W)(carboxy), $C_{1-4}$alkyl(W)(sulfo), $C_{2-4}$alkenyl(W)(sulfo) or $C_{2-4}$alkynyl(W)(sulfo); where W is H, amino or A-D-E-G, where A is $C_{1-4}$alkylene, $C_{2-4}$alkenylene or $C_{2-4}$alkynylene; D is a direct link, amido, ureido, imino, azido, carbamoyl, thio or thionyl; E is a direct link, $C_{1-3}$alkylene, arylene or heteroarylene; and G is H, amino, nitro, cyano, hydrazinyl, thio or sulfonamido;
with the provisos that (i) if m, n or p are not 0, then q and r are 0; (ii) if q or r are not 0, then m, n and p are 0; (iii) if X is not H, then Y is a direct link; (iv) if Y is not a direct link, then Y′ is a direct link; (v) if Y′ is not a direct link, then Y is a direct link; (vi) if D is not a direct link, then G is H; (vii) if D is a single bond and G is not H, then E is a single bond; and (viii) if E is not a direct link or $C_{1-3}$alkylene, then G is H.

UNITED STATES PATENT AND TRADEMARK OFFICE

CERTIFICATE OF CORRECTION

PATENT NO. : 6,638,977 B1 
DATED : October 28, 2003
INVENTOR(S) : Madison et al.

It is certified that error appears in the above-identified patent and that said Letters Patent is hereby corrected as shown below:

Column 45,
Line 11, replace claims 6 and 7, with the following:

6. The pharmaceutical composition of claim 2, wherein the compound is of formula I with the proviso that X-Y'-Y is not hydrogen.

7. The pharmaceutical composition of claim 2, wherein:
Z and Z' are each carbon;
$R^1$ is iodo;
$R^2$ is iodo;
m is 2;
n is 1;
$R^3$ is OH;
p is an integer from 0 to 3;
$R^4$ and $R^5$ are each independently selected from $-SO_3^-$, $-NO_2$ and Me; q is an integer from 0 to 1; r is an integer from 0 to 2;

---

X is H, $C_{1-17}$alkyl-L-, $C_{2-17}$alkenyl-L-, or $C_{2-17}$alkynyl-L-; L is a direct link, amido, carboxy, carbonyl, carbamoyl, sulfonyl, carbamide, ureido, sulfonamide, hydrazinyl, hydrazide, semicarbazide, carbazate, thiocarbazate, isothiocarbazate or sulfonyl hydrazide;
Y' is a direct link, $C_8$alkylene, $-S(O)_2O-$,

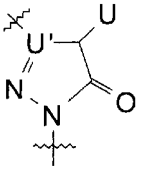 , or 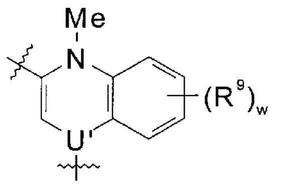 ;

where U' is carbon and is attached to X; $R^9$ is $SO_3H$; w is an integer from 0 to 2; U is H or

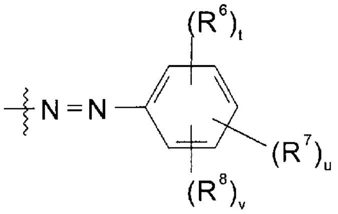 ;

--- where $R^6$ is OH; t is an integer from 0 to 3; $R^7$ is $C_{1-3}$alkoxy; u is an integer from 0 to 3; $R^8$ is halo; v is an integer from 0 to 3;
Y is a direct link, $C_{1-4}$alkyl(W)(carboxy), $C_{2-4}$alkenyl(W)(carboxy), $C_{2-4}$alkynyl(W)(carboxy), $C_{1-4}$alkyl(W)(sulfo), $C_{2-4}$alkenyl(W)(sulfo) or $C_{2-4}$alkynyl(W)(sulfo); where W is H, amino or A-D-E-G, where A is $C_{1-4}$alkylene, $C_{2-4}$alkenylene or $C_{2-4}$alkynylene; D is a direct link, amido, ureido, imino, azido, carbamoyl, thio or thionyl; E is a direct link, $C_{1-3}$alkylene, arylene or heteroarylene; and G is H, amino, nitro, cyano, hydrazinyl, thio or sulfonamido;
with the provisos that (i) if m, n or p are not 0, then q and r are 0; (ii) if q or r are not 0, then m, n and p are 0; (iii) if X is not H, then Y is a direct link; (iv) if Y is not a direct link, then Y' is a direct link; (v) if Y' is not a direct link, then Y is a direct link; (vi) if D is not a direct link, then G is H; (vii) if D is a single bond and G is not H, then E is a single bond; and (viii) if E is not a direct link or $C_{1-3}$alkylene, then G is H.

UNITED STATES PATENT AND TRADEMARK OFFICE
CERTIFICATE OF CORRECTION

PATENT NO. : 6,638,977 B1
DATED : October 28, 2003
INVENTOR(S) : Madison et al.

It is certified that error appears in the above-identified patent and that said Letters Patent is hereby corrected as shown below:

Column 47,
Line 19, replace claim 11, with the following

11. A method of treating, preventing, or ameliorating one or more symptoms of cancer, comprising administering a compound of formula:

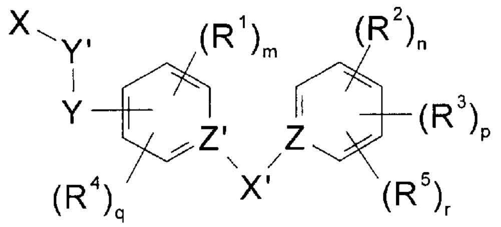

or a pharmaceutically acceptable derivative thereof, wherein:

Z and Z′ are each carbon;

X′ is $(CH_2)_dO$ or $(CH_2)_dS$;

d is an integer from 1 to 6;

$R^1$ is halide or pseudohalide;

m is 2;

$R^2$, $R^3$, n and p are selected from (i) or (ii) as follows:

(i) $R^2$ is alkyl, aryl, alkoxy, haloalkyl, haloalkoxy, halide or pseudohalide; n is an integer from 1 to 5; $R^3$ is hydroxy or alkoxy; p is an integer from 0 to 3; or (ii) n and p are 1; and $R^2$ and $R^3$, together form, with the carbon to which each is attached, an aryl, aromatic ring, heteroaromatic ring, carbocyclic or heterocyclic ring, which is saturated or unsaturated, containing from about 3 to about 16 members;

$R^4$ and $R^5$ are each independently selected from $-SO_3^-$, $-NO_2$, alkyl, hydroxy, alkoxy, halide or pseudohalide;

q is an integer from 0 to 1;

r is an integer from 0 to 2;

X is H, $C_{1-17}$alkyl-L-, $C_{2-17}$alkenyl-L-, or $C_{2-17}$alkynyl-L-;

L is a direct link, amido, carboxy, carbonyl, carbamoyl, sulfonyl, carbamide, ureido, sulfonamide, hydrazinyl, hydrazide, semicarbazide, carbazate, thiocarbazate, isothiocarbazate or sulfonyl hydrazide;

Y′ is selected from a direct link, alkylene, a heterocyclylene group, -COO-, -$S(O)_2O$-, -S(O)O-, -P(O)(OH)O-, -P(OH)O- and -B(OH)O-;

Y is a direct link, $C_{1-4}$alkyl(W)(carboxy), $C_{2-4}$alkenyl(W)(carboxy), $C_{2-4}$alkynyl(W)(carboxy), $C_{1-4}$alkyl(W)(sulfo), $C_{2-4}$alkenyl(W)(sulfo) or $C_{2-4}$alkynyl(W)(sulfo); where W is H, amino or A-D-E-G, where A is $C_{1-4}$alkylene, $C_{2-4}$alkenylene or $C_{2-4}$alkynylene; D is a direct link, amido, ureido, imino, azido, carbamoyl, thio or thionyl; E is a direct link, $C_{1-3}$alkylene, arylene or heteroarylene; and G is H, amino, nitro, cyano, hydrazinyl, thio or sulfonamido;

with the provisos that (i) if m, n or p are not 0, then q and r are 0; (ii) if q or r are not 0, then m, n and p are 0; (iii) if X is not H, then Y is a direct link; (iv) if Y is not a direct link, then Y′ is a direct link; (v) if Y′ is not a direct link, then Y is a direct link; (vi) if D is not a direct link, then G is H; (vii) if D is a single bond and G is not H, then E is a single bond; and (viii) if E is not a direct link or $C_{1-3}$alkylene, then G is H.

CERTIFICATE OF CORRECTION

PATENT NO. : 6,638,977 B1
DATED : October 28, 2003
INVENTOR(S) : Madison et al.

It is certified that error appears in the above-identified patent and that said Letters Patent is hereby corrected as shown below:

Column 49,
Line 56, replace claim 16, with the following:

16. The method of claim 15, wherein the compound has the formula:

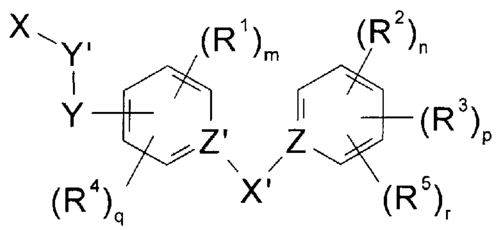

or a pharmaceutically acceptable derivative thereof, wherein:

Z and Z′ are each carbon;

X′ is O, S, $(CH_2)_dO$ or $(CH_2)_dS$;

d is an integer from 1 to 6;

$R^1$ is alkyl, aryl, alkoxy, haloalkyl, haloalkoxy, halide or pseudohalide;

m is an integer from 0 to 4;

---

$R^2$, $R^3$, n and p are selected from (i) or (ii) as follows:

(i) $R^2$ is alkyl, aryl, alkoxy, haloalkyl, haloalkoxy, halide or pseudohalide; n is an integer from 0 to 5; $R^3$ is hydroxy or alkoxy; p is an integer from 0 to 3; or (ii) n and p are 1; and $R^2$ and $R^3$, together form, with the carbon to which each is attached, an aryl, aromatic ring, heteroaromatic ring, carbocyclic or heterocyclic ring, which is saturated or unsaturated, containing from about 3 to about 16 members;

$R^4$ and $R^5$ are each independently selected from $-SO_3^-$, $-NO_2$, alkyl, hydroxy, alkoxy, halide or pseudohalide;

q is an integer from 0 to 1;

r is an integer from 0 to 2;

X is H, $C_{1-17}$alkyl-L-, $C_{2-17}$alkenyl-L-, or $C_{2-17}$alkynyl-L-;

L is a direct link, amido, carboxy, carbonyl, carbamoyl, sulfonyl, carbamide, ureido, sulfonamide, hydrazinyl, hydrazide, semicarbazide, carbazate, thiocarbazate, isothiocarbazate or sulfonyl hydrazide;

Y′ is selected from a direct link, alkylene, a heterocyclylene group, -COO-, -$S(O)_2O$-, -S(O)O-, -P(O)(OH)O-, -P(OH)O- and -B(OH)O-;

Y is a direct link, $C_{1-4}$alkyl(W)(carboxy), $C_{2-4}$alkenyl(W)(carboxy), $C_{2-4}$alkynyl(W)(carboxy), $C_{1-4}$alkyl(W)(sulfo), $C_{2-4}$alkenyl(W)(sulfo) or $C_{2-4}$alkynyl(W)(sulfo); where W is H, amino or A-D-E-G, where A is $C_{1-4}$alkylene, $C_{2-4}$alkenylene or $C_{2-4}$alkynylene; D is a direct link, amido, ureido, imino, azido, carbamoyl, thio or thionyl; E is a direct link, $C_{1-3}$alkylene, arylene or heteroarylene; and G is H, amino, nitro, cyano, hydrazinyl, thio or sulfonamido;

with the provisos that (i) if m, n or p are not 0, then q and r are 0; (ii) if q or r are not 0, then m, n and p are 0; (iii) if X is not H, then Y is a direct link; (iv) if Y is not a direct link, then Y′ is a direct link; (v) if Y′ is not a direct link, then Y is a direct link; (vi) if D is not a direct link, then G is H; (vii) if D is a single bond and G is not H, then E is a single bond; and (viii) if E is not a direct link or $C_{1-3}$alkylene, then G is H.

UNITED STATES PATENT AND TRADEMARK OFFICE
CERTIFICATE OF CORRECTION

PATENT NO. : 6,638,977 B1 
DATED : October 28, 2003
INVENTOR(S) : Madison et al.

It is certified that error appears in the above-identified patent and that said Letters Patent is hereby corrected as shown below:

Column 15,
Line 5, replace claim 18, with the following

18. The method of claim 17, wherein the compound has the formula:

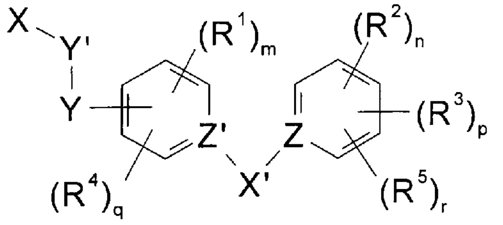

or a pharmaceutically acceptable derivative thereof, wherein:
Z and Z' are each carbon;
X' is O, S, $(CH_2)_dO$ or $(CH_2)_dS$;
d is an integer from 1 to 6;
$R^1$ is alkyl, aryl, alkoxy, haloalkyl, haloalkoxy, halide or pseudohalide;
m is an integer from 0 to 4;
$R^2$, $R^3$, n and p are selected from (i) or (ii) as follows:
(i) $R^2$ is alkyl, aryl, alkoxy, haloalkyl, haloalkoxy, halide or pseudohalide; n is an integer from 0 to 5; $R^3$ is hydroxy or alkoxy; p is an integer from 0 to 3; or
(ii) n and p are 1; and $R^2$ and $R^3$, together form, with the carbon to which each is attached, an aryl, aromatic ring, heteroaromatic ring, carbocyclic or heterocyclic ring, which is saturated or unsaturated, containing from about 3 to about 16 members;

$R^4$ and $R^5$ are each independently selected from $-SO_3^-$, $-NO_2$, alkyl, hydroxy, alkoxy, halide or pseudohalide;
q is an integer from 0 to 1;
r is an integer from 0 to 2;
X is H, $C_{1-17}$alkyl-L-, $C_{2-17}$alkenyl-L-, or $C_{2-17}$alkynyl-L-;
L is a direct link, amido, carboxy, carbonyl, carbamoyl, sulfonyl, carbamide, ureido, sulfonamide, hydrazinyl, hydrazide, semicarbazide, carbazate, thiocarbazate, isothiocarbazate or sulfonyl hydrazide;
Y' is selected from a direct link, alkylene, a heterocyclylene group, -COO-, -$S(O)_2O$-, -S(O)O-, -P(O)(OH)O-, -P(OH)O- and -B(OH)O-;
Y is a direct link, $C_{1-4}$alkyl(W)(carboxy), $C_{2-4}$alkenyl(W)(carboxy), $C_{2-4}$alkynyl(W)(carboxy), $C_{1-4}$alkyl(W)(sulfo), $C_{2-4}$alkenyl(W)(sulfo) or $C_{2-4}$alkynyl(W)(sulfo); where W is H, amino or A-D-E-G, where A is $C_{1-4}$alkylene, $C_{2-4}$alkenylene or $C_{2-4}$alkynylene; D is a direct link, amido, ureido, imino, azido, carbamoyl, thio or thionyl; E is a direct link, $C_{1-3}$alkylene, arylene or heteroarylene; and G is H, amino, nitro, cyano, hydrazinyl, thio or sulfonamido;
with the provisos that (i) if m, n or p are not 0, then q and r are 0; (ii) if q or r are not 0, then m, n and p are 0; (iii) if X is not H, then Y is a direct link; (iv) if Y is not a direct link, then Y' is a direct link; (v) if Y' is not a direct link, then Y is a direct link; (vi) if D is not a direct link, then G is H; (vii) if D is a single bond and G is not H, then E is a single bond; and (viii) if E is not a direct link or $C_{1-3}$alkylene, then G is H.

UNITED STATES PATENT AND TRADEMARK OFFICE
CERTIFICATE OF CORRECTION

PATENT NO. : 6,638,977 B1
DATED : October 28, 2003
INVENTOR(S) : Madison et al.

It is certified that error appears in the above-identified patent and that said Letters Patent is hereby corrected as shown below:

Column 51,
Line 65, replace claim 19, with the following:

19. A method of treating, preventing or ameliorating one or more symptoms of a thrombotic disorder or haemostatic disorder, comprising administrating a compound of formula $Ar^1$-X'-$Ar^2$, or pharmaceutically acceptable derivatives thereof, wherein:

X' is O, S, $(CH_2)_dO$ or $(CH_2)_dS$ where d is an integer from 1 to 6;

$Ar^1$ and $Ar^2$ are each independently selected from monocyclic or fused bicyclic aryl and heteroaryl, and are substituted with at least one acidic group selected from a carboxylic acid, sulfonic acid, sulfinic acid, phosphonic acid, phosphinic acid or boronic acid group;

and may be further substituted with one or more substituents independently selected from halide, pseudohalide, nitro, hydroxy, alkoxy, aryl, heteroaryl, heterocyclyl, alkyl or cycloalkyl; wherein the aryl, heteroaryl, heterocyclyl and cycloalkyl substituents may be further substituted with $C_{1-20}$alkyl-L-, $C_{2-20}$alkenyl-L-, or $C_{2-20}$alkynyl-L-, where L is a direct link, amido, carboxy, carbonyl, carbamoyl, sulfonyl, carbamide, ureido, sulfonamide, hydrazinyl, hydrazide, semicarbazide, carbazate, thiocarbazate, isothiocarbazate or sulfonyl hydrazide.

---

Column 53,
Line 22, replace claims 23, 24 and 25, with the following:

23. A method of antagonizing a plasminogen activator inhibitor (PAI), comprising contacting the PAI with a compound of formula $Ar^1$-X'-$Ar^2$, or pharmaceutically acceptable derivatives thereof, wherein:

X' is O, S, $(CH_2)_dO$ or $(CH_2)_dS$ where d is an integer from 1 to 6;

$Ar^1$ and $Ar^2$ are each independently selected from monocyclic or fused bicyclic aryl and heteroaryl, and are substituted with at least one acidic group selected from a carboxylic acid, sulfonic acid, sulfinic acid, phosphonic acid, phosphinic acid or boronic acid group;

---

UNITED STATES PATENT AND TRADEMARK OFFICE
CERTIFICATE OF CORRECTION

PATENT NO. : 6,638,977 B1
DATED : October 28, 2003
INVENTOR(S) : Madison et al.

It is certified that error appears in the above-identified patent and that said Letters Patent is hereby corrected as shown below:

Column 53 (cont'd), (ii) n and p are 1; and $R^2$ and $R^3$, together form, with the carbon to which each is attached, an aryl, aromatic ring, heteroaromatic ring, carbocyclic or heterocyclic ring, which is saturated or unsaturated, containing from about 3 to about 16 members;

$R^4$ and $R^5$ are each independently selected from $-SO_3^-$, $-NO_2$, alkyl, hydroxy, alkoxy, halide or pseudohalide;

q is an integer from 0 to 1;

r is an integer from 0 to 2;

X is H, $C_{1-17}$alkyl-L-, $C_{2-17}$alkenyl-L-, or $C_{2-17}$alkynyl-L-;

L is a direct link, amido, carboxy, carbonyl, carbamoyl, sulfonyl, carbamide, ureido, sulfonamide, hydrazinyl, hydrazide, semicarbazide, carbazate, thiocarbazate, isothiocarbazate or sulfonyl hydrazide;

Y' is selected from a direct link, alkylene, a heterocyclylene group, -COO-, -$S(O)_2O$-, -S(O)O-, -P(O)(OH)O-, -P(OH)O- and -B(OH)O-;

Y is a direct link, $C_{1-4}$alkyl(W)(carboxy), $C_{2-4}$alkenyl(W)(carboxy), $C_{2-4}$alkynyl(W)(carboxy), $C_{1-4}$alkyl(W)(sulfo), $C_{2-4}$alkenyl(W)(sulfo) or $C_{2-4}$alkynyl(W)(sulfo); where W is H, amino or A-D-E-G, where A is $C_{1-4}$alkylene, $C_{2-4}$alkenylene or $C_{2-4}$alkynylene; D is a direct link, amido, ureido, imino, azido, carbamoyl, thio or thionyl; E is a direct link, $C_{1-3}$alkylene, arylene or heteroarylene; and G is H, amino, nitro, cyano, hydrazinyl, thio or sulfonamido;

with the provisos that (i) if m, n or p are not 0, then q and r are 0; (ii) if q or r are not 0, then m, n and p are 0; (iii) if X is not H, then Y is a direct link; (iv) if Y is not a direct link, then Y' is a direct link; (v) if Y' is not a direct link, then Y is a direct link; (vi) if D is not a direct link, then G is H; (vii) if D is a single bond and G is not H, then E is a single bond; and (viii) if E is not a direct link or $C_{1-3}$alkylene, then G is H.

--- and may be further substituted with one or more substituents independently selected from halide, pseudohalide, nitro, hydroxy, alkoxy, aryl, heteroaryl, heterocyclyl, alkyl or cycloalkyl; wherein the aryl, heteroaryl, heterocyclyl and cycloalkyl substituents may be further substituted with $C_{1-20}$alkyl-L-, $C_{2-20}$alkenyl-L-, or $C_{2-20}$alkynyl-L-, where L is a direct link, amido, carboxy, carbonyl, carbamoyl, sulfonyl, carbamide, ureido, sulfonamide, hydrazinyl, hydrazide, semicarbazide, carbazate, thiocarbazate, isothiocarbazate or sulfonyl hydrazide.

24. The method of claim 23, wherein the compound has the formula:

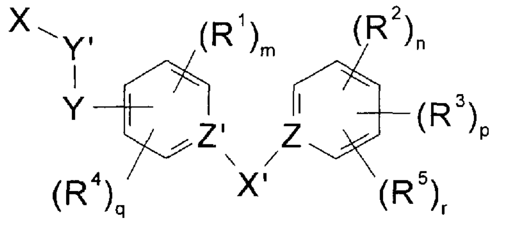

---

UNITED STATES PATENT AND TRADEMARK OFFICE
CERTIFICATE OF CORRECTION

PATENT NO. : 6,638,977 B1
DATED : October 28, 2003
INVENTOR(S) : Madison et al.

It is certified that error appears in the above-identified patent and that said Letters Patent is hereby corrected as shown below:

Column 53 (cont'd), or a pharmaceutically acceptable derivative thereof, wherein:

Z and Z' are each carbon;

X' is O, S, $(CH_2)_dO$ or $(CH_2)_dS$;

d is an integer from 1 to 6;

$R^1$ is alkyl, aryl, alkoxy, haloalkyl, haloalkoxy, halide or pseudohalide;

m is an integer from 0 to 4;

$R^2$, $R^3$, n and p are selected from (i) or (ii) as follows:

(i) $R^2$ is alkyl, aryl, alkoxy, haloalkyl, haloalkoxy, halide or pseudohalide; n is an integer from 0 to 5; $R^3$ is hydroxy or alkoxy; p is an integer from 0 to 3; or

---

25. A method of modulating angiogenesis, comprising administering a compound of formula $Ar^1$-X'-$Ar^2$, or pharmaceutically acceptable derivatives thereof, wherein:

X' is O, S, $(CH_2)_dO$ or $(CH_2)_dS$ where d is an integer from 1 to 6;

$Ar^1$ and $Ar^2$ are each independently selected from monocyclic or fused bicyclic aryl and heteroaryl, and are substituted with at least one acidic group selected from a carboxylic acid, sulfonic acid, sulfinic acid, phosphonic acid, phosphinic acid or boronic acid group;

and may be further substituted with one or more substituents independently selected from halide, pseudohalide, nitro, hydroxy, alkoxy, aryl, heteroaryl, heterocyclyl, alkyl or cycloalkyl; wherein the aryl, heteroaryl, heterocyclyl and cycloalkyl substituents may be further substituted with $C_{1-20}$alkyl-L-, $C_{2-20}$alkenyl-L-, or $C_{2-20}$alkynyl-L-, where L is a direct link, amido, carboxy, carbonyl, carbamoyl, sulfonyl, carbamide, ureido, sulfonamide, hydrazinyl, hydrazide, semicarbazide, carbazate, thiocarbazate, isothiocarbazate or sulfonyl hydrazide.

---

Column 58,

Line 26, replace claim 37, with the following:

37. The compound of claim 33, wherein X-Y is $(CH_2)_aCOOH$, where a is an integer from 0 to 6.

---

Line 28, replace claim 38, with the following:

38. The compound of claim 37, wherein a is 0 or 2.

Line 62, replace claim 41, with the following:

41. The compound of claim 39, wherein $R^1$ is Br or I; m is 2; and $R^2$, $R^3$, n and p are selected from (i) or (ii) as follows:

(i) $R^2$ is selected from I, Br, $CH_3$, $C(CH_3)_3$, Ph, $OCH_3$, $CF_3$, $OCF_3$ or F; n is 1, or is 1 or 5 when $R^2$ is F; p is 0; or (ii) n and p are 1; and $R^2$ and $R^3$ together form -CH=CH-CH=CH-.

---

UNITED STATES PATENT AND TRADEMARK OFFICE

CERTIFICATE OF CORRECTION

PATENT NO. : 6,638,977 B1
DATED : October 28, 2003
INVENTOR(S) : Madison et al.

It is certified that error appears in the above-identified patent and that said Letters Patent is hereby corrected as shown below:

Column 59,
Line 4, replace claim 43, with the following:
43. The compound of claim 42, wherein a is 0 or 2.

Signed and Sealed this

Thirty-first Day of August, 2004

JON W. DUDAS
*Director of the United States Patent and Trademark Office*